(12) United States Patent
Haarer et al.

(10) Patent No.: US 12,064,344 B2
(45) Date of Patent: Aug. 20, 2024

(54) TELESCOPING PROSTHETIC VALVE AND DELIVERY SYSTEM

(71) Applicant: Edwards Lifesciences Corporation, Irvine, CA (US)

(72) Inventors: Joshua C. Haarer, Flagstaff, AZ (US); Cody L. Hartman, Flagstaff, AZ (US); Roy Manygoats, Jr., Flagstaff, AZ (US); Ryan S. Titone, Flagstaff, AZ (US); Eric M. Tittelbaugh, Flagstaff, AZ (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 255 days.

(21) Appl. No.: 17/383,569

(22) Filed: Jul. 23, 2021

(65) Prior Publication Data
US 2021/0346156 A1  Nov. 11, 2021

Related U.S. Application Data

(63) Continuation of application No. 16/129,779, filed on Sep. 12, 2018, now Pat. No. 11,090,153.

(Continued)

(51) Int. Cl.
*A61F 2/24* (2006.01)
*A61F 2/82* (2013.01)

(52) U.S. Cl.
CPC .......... *A61F 2/2418* (2013.01); *A61F 2/2436* (2013.01); *A61F 2/246* (2013.01); *A61F 2/2433* (2013.01); *A61F 2/2439* (2013.01); *A61F 2/2454* (2013.01); *A61F 2002/825* (2013.01); *A61F 2210/0014* (2013.01); *A61F 2220/0016* (2013.01); *A61F 2220/0025* (2013.01);

(Continued)

(58) Field of Classification Search
CPC ........ A61F 2/24; A61F 2/2403; A61F 2/2406; A61F 2/2409; A61F 2/2412; A61F 2/2418; A61F 2/2421; A61F 2/2424; A61F 2/2427; A61F 2/243; A61F 2/2433; A61F 2/2436; A61F 2/2439; A61F 2/2442; A61F 2/2445; A61F 2/2448; A61F 2/2451; A61F 2/246; A61F 2/2466; A61F 2/2469; A61F 2/2476; A61F 2250/006; A61F 2250/0063
See application file for complete search history.

(56) References Cited

U.S. PATENT DOCUMENTS

| | | |
|---|---|---|
| 654,799 A | 7/1900 | Levett |
| 3,739,402 A | 6/1973 | Kahn et al. |

(Continued)

FOREIGN PATENT DOCUMENTS

| | | |
|---|---|---|
| AU | 2013363172 A1 | 7/2015 |
| AU | 2017202405 A1 | 4/2017 |

(Continued)

OTHER PUBLICATIONS

Forward citations for E12 obtained from: https://scholar.google.com/scholar?cites=5981833429320176658&assdt=2005&sciodt=0,5&hl=en.

(Continued)

*Primary Examiner* — Diane D Yabut
(74) *Attorney, Agent, or Firm* — Thomas C. Richardson

(57) ABSTRACT

An implantable device is disclosed. The device includes a two or three-piece frame assembly that is configured to be delivered in a series configuration and subsequently nested or telescoped in-situ.

8 Claims, 27 Drawing Sheets

Related U.S. Application Data

(60) Provisional application No. 62/579,762, filed on Oct. 31, 2017, provisional application No. 62/572,281, filed on Oct. 13, 2017.

(52) U.S. Cl.
CPC . *A61F 2220/0075* (2013.01); *A61F 2230/005* (2013.01); *A61F 2230/0052* (2013.01); *A61F 2230/0054* (2013.01); *A61F 2230/0069* (2013.01); *A61F 2250/0039* (2013.01); *A61F 2250/006* (2013.01); *A61F 2250/0063* (2013.01)

(56) References Cited

U.S. PATENT DOCUMENTS

| | | |
|---|---|---|
| 3,953,566 A | 4/1976 | Gore |
| 4,178,639 A | 12/1979 | Bokros |
| 4,187,390 A | 2/1980 | Gore |
| 4,222,126 A | 9/1980 | Boretos et al. |
| 4,265,694 A | 5/1981 | Boretos et al. |
| 4,332,035 A | 6/1982 | Mano |
| 4,340,091 A | 7/1982 | Skelton et al. |
| 4,477,930 A | 10/1984 | Totten et al. |
| 4,556,996 A | 12/1985 | Wallace |
| 4,626,255 A | 12/1986 | Reichart et al. |
| 4,759,759 A | 7/1988 | Walker et al. |
| 4,851,000 A | 7/1989 | Gupta |
| 4,877,661 A | 10/1989 | House et al. |
| 4,955,899 A | 9/1990 | Della et al. |
| 5,026,513 A | 6/1991 | House et al. |
| 5,064,435 A | 11/1991 | Porter |
| 5,071,609 A | 12/1991 | Tu et al. |
| 5,123,918 A | 6/1992 | Perrier et al. |
| 5,163,955 A | 11/1992 | Love et al. |
| 5,415,667 A | 5/1995 | Frater |
| 5,469,868 A | 11/1995 | Reger |
| 5,476,589 A | 12/1995 | Bacino |
| 5,489,297 A | 2/1996 | Duran |
| 5,534,007 A | 7/1996 | St. Germain et al. |
| 5,549,663 A | 8/1996 | Cottone, Jr. |
| 5,554,183 A | 9/1996 | Nazari |
| 5,554,185 A | 9/1996 | Block et al. |
| 5,562,729 A | 10/1996 | Purdy |
| 5,628,791 A | 5/1997 | Bokros et al. |
| 5,673,102 A | 9/1997 | Suzuki et al. |
| 5,708,044 A | 1/1998 | Branca |
| 5,718,973 A | 2/1998 | Lewis et al. |
| 5,749,852 A | 5/1998 | Schwab et al. |
| 5,752,934 A | 5/1998 | Campbell et al. |
| 5,759,192 A | 6/1998 | Saunders |
| 5,769,884 A | 6/1998 | Solovay |
| 5,772,884 A | 6/1998 | Tanaka et al. |
| 5,788,626 A | 8/1998 | Thompson |
| 5,814,405 A | 9/1998 | Branca et al. |
| 5,824,043 A | 10/1998 | Cottone, Jr. |
| 5,843,158 A | 12/1998 | Lenker et al. |
| 5,843,161 A | 12/1998 | Solovay |
| 5,843,171 A | 12/1998 | Campbell et al. |
| 5,853,419 A | 12/1998 | Imran |
| 5,925,061 A | 7/1999 | Ogi et al. |
| 5,928,281 A | 7/1999 | Huynh et al. |
| 5,935,162 A | 8/1999 | Dang |
| 5,935,163 A | 8/1999 | Gabbay |
| 5,944,654 A | 8/1999 | Crawford |
| 5,957,974 A | 9/1999 | Thompson et al. |
| 6,010,529 A | 1/2000 | Herweck et al. |
| 6,013,854 A | 1/2000 | Moriuchi |
| 6,019,785 A | 2/2000 | Strecker |
| 6,042,588 A | 3/2000 | Munsinger et al. |
| 6,042,605 A | 3/2000 | Martin et al. |
| 6,042,606 A | 3/2000 | Frantzen |
| 6,086,612 A | 7/2000 | Jansen |
| 6,110,198 A | 8/2000 | Fogarty et al. |
| 6,117,169 A | 9/2000 | Moe |
| 6,129,758 A | 10/2000 | Love |
| 6,161,399 A | 12/2000 | Jayaraman |
| 6,165,211 A | 12/2000 | Thompson |
| 6,171,335 B1 | 1/2001 | Wheatley et al. |
| 6,174,329 B1 | 1/2001 | Callol et al. |
| 6,174,331 B1 | 1/2001 | Moe et al. |
| 6,190,406 B1 | 2/2001 | Duerig et al. |
| 6,197,143 B1 | 3/2001 | Bodnar |
| 6,217,609 B1 | 4/2001 | Haverkost |
| 6,245,012 B1 | 6/2001 | Kleshinski |
| 6,261,320 B1 | 7/2001 | Tam et al. |
| 6,261,620 B1 | 7/2001 | Leadbeater |
| 6,283,994 B1 | 9/2001 | Moe et al. |
| 6,283,995 B1 | 9/2001 | Moe et al. |
| 6,287,334 B1 | 9/2001 | Moll et al. |
| 6,328,763 B1 | 12/2001 | Love et al. |
| 6,334,873 B1 | 1/2002 | Lane et al. |
| 6,336,937 B1 | 1/2002 | Vonesh et al. |
| 6,352,552 B1 | 3/2002 | Levinson et al. |
| 6,379,382 B1 | 4/2002 | Yang |
| 6,436,132 B1 | 8/2002 | Patel et al. |
| 6,454,798 B1 | 9/2002 | Moe |
| 6,454,799 B1 | 9/2002 | Schreck |
| 6,461,382 B1 | 10/2002 | Cao |
| 6,461,665 B1 | 10/2002 | Scholander |
| 6,482,228 B1 | 11/2002 | Norred |
| 6,488,701 B1 | 12/2002 | Nolting et al. |
| 6,541,589 B1 | 4/2003 | Baillie |
| 6,558,418 B2 | 5/2003 | Carpentier et al. |
| 6,562,069 B2 | 5/2003 | Cai et al. |
| 6,582,464 B2 | 6/2003 | Gabbay |
| 6,613,086 B1 | 9/2003 | Moe et al. |
| 6,620,190 B1 | 9/2003 | Colone |
| 6,626,939 B1 | 9/2003 | Burnside et al. |
| 6,645,244 B2 | 11/2003 | Shu et al. |
| 6,666,885 B2 | 12/2003 | Moe |
| 6,673,102 B1 | 1/2004 | Vonesh et al. |
| 6,673,107 B1 | 1/2004 | Brandt et al. |
| 6,726,715 B2 | 4/2004 | Sutherland |
| 6,730,118 B2 | 5/2004 | Spenser et al. |
| 6,730,120 B2 | 5/2004 | Berg et al. |
| 6,755,856 B2 | 6/2004 | Fierens et al. |
| 6,755,857 B2 | 6/2004 | Peterson et al. |
| 6,758,858 B2 | 7/2004 | McCrea et al. |
| 6,890,350 B1 | 5/2005 | Walak |
| 6,893,460 B2 | 5/2005 | Spenser et al. |
| 6,916,338 B2 | 7/2005 | Speziali |
| 6,936,067 B2 | 8/2005 | Buchanan |
| 6,953,332 B1 | 10/2005 | Kurk et al. |
| 7,022,132 B2 | 4/2006 | Kocur |
| 7,049,380 B1 | 5/2006 | Chang et al. |
| 7,083,642 B2 | 8/2006 | Sirhan et al. |
| 7,105,018 B1 | 9/2006 | Yip et al. |
| 7,137,184 B2 | 11/2006 | Schreck |
| 7,163,556 B2 | 1/2007 | Xie et al. |
| 7,238,200 B2 | 7/2007 | Lee et al. |
| 7,247,167 B2 | 7/2007 | Gabbay |
| 7,306,729 B2 | 12/2007 | Bacino et al. |
| 7,381,218 B2 | 6/2008 | Schreck |
| 7,419,678 B2 | 9/2008 | Falotico |
| 7,462,675 B2 | 12/2008 | Chang et al. |
| 7,510,575 B2 | 3/2009 | Spenser et al. |
| 7,513,909 B2 | 4/2009 | Lane et al. |
| 7,531,611 B2 | 5/2009 | Sabol et al. |
| 7,563,277 B2 | 7/2009 | Case et al. |
| 7,708,775 B2 | 5/2010 | Rowe et al. |
| 7,727,274 B2 | 6/2010 | Zilla et al. |
| 7,758,640 B2 | 7/2010 | Vesely |
| 7,780,725 B2 | 8/2010 | Haug et al. |
| 7,789,908 B2 | 9/2010 | Sowinski et al. |
| 7,803,186 B1 | 9/2010 | Li et al. |
| 7,811,314 B2 | 10/2010 | Fierens et al. |
| 7,815,763 B2 | 10/2010 | Fierens et al. |
| 7,879,085 B2 | 2/2011 | Sowinski et al. |
| 7,887,562 B2 | 2/2011 | Young et al. |
| 7,914,569 B2 | 3/2011 | Nguyen et al. |
| 7,927,364 B2 | 4/2011 | Fierens et al. |
| 7,927,365 B2 | 4/2011 | Fierens et al. |
| 7,935,141 B2 | 5/2011 | Randall et al. |

(56) References Cited

U.S. PATENT DOCUMENTS

| | | |
|---|---|---|
| 7,967,829 B2 | 6/2011 | Gunderson et al. |
| 7,967,853 B2 | 6/2011 | Eidenschink et al. |
| 7,993,394 B2 | 8/2011 | Hariton et al. |
| 8,048,440 B2 | 11/2011 | Chang et al. |
| 8,062,359 B2 | 11/2011 | Marquez et al. |
| 8,092,523 B2 | 1/2012 | Li et al. |
| 8,167,935 B2 | 5/2012 | McGuckin et al. |
| 8,226,710 B2 | 7/2012 | Nguyen et al. |
| 8,246,678 B2 | 8/2012 | Salahieh et al. |
| 8,252,037 B2 | 8/2012 | Styrc et al. |
| 8,303,647 B2 | 11/2012 | Case |
| 8,349,000 B2 | 1/2013 | Schreck |
| 8,409,274 B2 | 4/2013 | Li et al. |
| 8,475,512 B2 | 7/2013 | Hunt |
| 8,545,525 B2 | 10/2013 | Surti et al. |
| 8,568,475 B2 | 10/2013 | Nguyen et al. |
| 8,585,753 B2 | 11/2013 | Scanlon et al. |
| 8,585,757 B2 | 11/2013 | Agathos |
| 8,628,566 B2 | 1/2014 | Eberhardt et al. |
| 8,637,144 B2 | 1/2014 | Ford |
| 8,709,077 B2 | 4/2014 | Schreck |
| 8,722,178 B2 | 5/2014 | Ashmead et al. |
| 8,728,103 B2 | 5/2014 | Surti et al. |
| 8,728,154 B2 | 5/2014 | Alkhatib |
| 8,784,481 B2 | 7/2014 | Alkhatib et al. |
| 8,801,774 B2 | 8/2014 | Silverman |
| 8,808,848 B2 | 8/2014 | Bacino |
| 8,845,709 B2 | 9/2014 | Styrc et al. |
| 8,845,721 B2 | 9/2014 | Braido et al. |
| 8,852,272 B2 | 10/2014 | Gross et al. |
| 8,870,948 B1 | 10/2014 | Erzberger et al. |
| 8,936,634 B2 | 1/2015 | Irwin et al. |
| 8,945,212 B2 | 2/2015 | Bruchman et al. |
| 8,961,599 B2 | 2/2015 | Bruchman et al. |
| 8,992,608 B2 | 3/2015 | Haug et al. |
| 9,039,757 B2 | 5/2015 | McLean et al. |
| 9,101,469 B2 | 8/2015 | Bruchman et al. |
| 9,101,696 B2 | 8/2015 | Leontein et al. |
| 9,107,771 B2 | 8/2015 | Wubbeling et al. |
| 9,125,740 B2 | 9/2015 | Morriss et al. |
| 9,139,669 B2 | 9/2015 | Xu et al. |
| 9,144,492 B2 | 9/2015 | Bruchman et al. |
| 9,168,131 B2 | 10/2015 | Yohanan et al. |
| 9,198,787 B2 | 12/2015 | Kratzberg et al. |
| 9,241,695 B2 | 1/2016 | Peavey et al. |
| 9,259,313 B2 | 2/2016 | Wheatley |
| 9,283,072 B2 | 3/2016 | Bruchman et al. |
| 9,295,552 B2 | 3/2016 | McLean et al. |
| 9,314,355 B2 | 4/2016 | Styrc et al. |
| 9,345,601 B2 | 5/2016 | Jantzen et al. |
| 9,375,308 B2 | 6/2016 | Norris |
| 9,393,110 B2 | 7/2016 | Levi et al. |
| 9,398,952 B2 | 7/2016 | Bruchman et al. |
| 9,399,085 B2 | 7/2016 | Cleek et al. |
| 9,504,565 B2 | 11/2016 | Armstrong |
| 9,554,786 B2 | 1/2017 | Carley et al. |
| 9,554,900 B2 | 1/2017 | Bruchman et al. |
| 9,597,181 B2 | 3/2017 | Christianson et al. |
| 9,629,718 B2 | 4/2017 | Gloss et al. |
| 9,681,948 B2 | 6/2017 | Levi et al. |
| 9,737,398 B2 | 8/2017 | Bruchman et al. |
| 9,737,422 B2 | 8/2017 | Armstrong et al. |
| 9,743,932 B2 | 8/2017 | Amplatz et al. |
| 9,795,496 B2 | 10/2017 | Armstrong et al. |
| 9,801,712 B2 | 10/2017 | Bruchman et al. |
| 9,827,089 B2 | 11/2017 | Bruchman et al. |
| 9,827,094 B2 | 11/2017 | Bennett |
| 9,839,540 B2 | 12/2017 | Armstrong et al. |
| 9,855,141 B2 | 1/2018 | Dienno et al. |
| 9,931,193 B2 | 4/2018 | Cully et al. |
| 9,931,204 B2 | 4/2018 | Rothstein et al. |
| 9,937,037 B2 | 4/2018 | Dienno et al. |
| 9,968,443 B2 | 5/2018 | Bruchman et al. |
| 10,039,638 B2 | 8/2018 | Bruchman et al. |
| 10,166,128 B2 | 1/2019 | Armstrong et al. |
| 10,279,084 B2 | 5/2019 | Goepfrich et al. |
| 10,285,808 B2 | 5/2019 | Bruchman et al. |
| 10,314,697 B2 | 6/2019 | Gassler |
| 10,321,986 B2 | 6/2019 | Bruchman et al. |
| 10,335,298 B2 | 7/2019 | Armstrong et al. |
| 10,342,659 B2 | 7/2019 | Bennett |
| 10,368,984 B2 | 8/2019 | Armstrong |
| 10,376,360 B2 | 8/2019 | Bruchman et al. |
| 10,441,416 B2 | 10/2019 | Oba et al. |
| 10,463,478 B2 | 11/2019 | Bruchman et al. |
| 10,507,124 B2 | 12/2019 | Armstrong et al. |
| 10,639,144 B2 | 5/2020 | Bruchman et al. |
| 10,660,745 B2 | 5/2020 | Bruchman et al. |
| 10,881,507 B2 | 1/2021 | Bruchman et al. |
| 10,980,633 B2 | 4/2021 | Dienno et al. |
| 11,020,221 B2 | 6/2021 | Arcaro et al. |
| 11,039,917 B2 | 6/2021 | Bruchman et al. |
| D926,322 S | 7/2021 | Bennett et al. |
| 11,065,112 B2 | 7/2021 | Gassler |
| 11,090,153 B2 | 8/2021 | Haarer et al. |
| 11,109,963 B2 | 9/2021 | Dienno et al. |
| 11,123,183 B2 | 9/2021 | Bennett et al. |
| 11,439,502 B2 | 9/2022 | Busalacchi et al. |
| 11,471,276 B2 | 10/2022 | Bennett |
| 2001/0053929 A1 | 12/2001 | Vonesh et al. |
| 2002/0045936 A1 | 4/2002 | Moe |
| 2002/0055773 A1 | 5/2002 | Campbell et al. |
| 2002/0076542 A1 | 6/2002 | Kramer et al. |
| 2002/0082687 A1 | 6/2002 | Moe |
| 2002/0133226 A1 | 9/2002 | Marquez et al. |
| 2002/0151953 A1 | 10/2002 | Chobotov et al. |
| 2002/0151956 A1 | 10/2002 | Chobotov et al. |
| 2002/0183840 A1 | 12/2002 | Lapeyre et al. |
| 2002/0198588 A1 | 12/2002 | Armstrong et al. |
| 2002/0198594 A1 | 12/2002 | Schreck |
| 2003/0014105 A1 | 1/2003 | Cao |
| 2003/0027332 A1 | 2/2003 | LaFrance et al. |
| 2003/0055494 A1 | 3/2003 | Bezuidenhout et al. |
| 2003/0055496 A1 | 3/2003 | Cai et al. |
| 2003/0060871 A1 | 3/2003 | Hill et al. |
| 2003/0074052 A1 | 4/2003 | Besselink et al. |
| 2003/0097175 A1 | 5/2003 | O'Connor et al. |
| 2003/0114913 A1 | 6/2003 | Spenser et al. |
| 2003/0125805 A1 | 7/2003 | Johnson et al. |
| 2003/0180488 A1 | 9/2003 | Lim et al. |
| 2003/0209835 A1 | 11/2003 | Chun et al. |
| 2003/0229394 A1 | 12/2003 | Ogle et al. |
| 2004/0024442 A1 | 2/2004 | Sowinski et al. |
| 2004/0024448 A1 | 2/2004 | Chang et al. |
| 2004/0024451 A1 | 2/2004 | Johnson et al. |
| 2004/0026245 A1 | 2/2004 | Agarwal et al. |
| 2004/0039436 A1 | 2/2004 | Spenser et al. |
| 2004/0044400 A1 | 3/2004 | Cheng et al. |
| 2004/0044401 A1 | 3/2004 | Bales et al. |
| 2004/0133266 A1 | 7/2004 | Clerc et al. |
| 2004/0170782 A1 | 9/2004 | Wang et al. |
| 2004/0176839 A1 | 9/2004 | Huynh et al. |
| 2004/0224442 A1 | 11/2004 | Grigg |
| 2004/0243222 A1 | 12/2004 | Osborne et al. |
| 2004/0260277 A1 | 12/2004 | Maguire |
| 2004/0260389 A1 | 12/2004 | Case et al. |
| 2004/0260393 A1 | 12/2004 | Rahdert et al. |
| 2005/0027348 A1 | 2/2005 | Case et al. |
| 2005/0080476 A1 | 4/2005 | Gunderson et al. |
| 2005/0119722 A1 | 6/2005 | Styrc et al. |
| 2005/0137680 A1 | 6/2005 | Ortiz et al. |
| 2005/0137682 A1 | 6/2005 | Justino |
| 2005/0203614 A1 | 9/2005 | Forster et al. |
| 2005/0261765 A1 | 11/2005 | Liddicoat |
| 2005/0283224 A1 | 12/2005 | King |
| 2006/0008497 A1 | 1/2006 | Gabbay |
| 2006/0009835 A1 | 1/2006 | Osborne et al. |
| 2006/0015171 A1 | 1/2006 | Armstrong |
| 2006/0036311 A1 | 2/2006 | Nakayama et al. |
| 2006/0041091 A1 | 2/2006 | Chang et al. |
| 2006/0106337 A1 | 5/2006 | Blankenship |
| 2006/0118236 A1 | 6/2006 | House et al. |
| 2006/0122693 A1 | 6/2006 | Biadillah et al. |
| 2006/0135985 A1 | 6/2006 | Cox et al. |

(56) References Cited

U.S. PATENT DOCUMENTS

| | | |
|---|---|---|
| 2006/0154365 A1 | 7/2006 | Ratcliffe et al. |
| 2006/0161241 A1 | 7/2006 | Barbut et al. |
| 2006/0190070 A1 | 8/2006 | Dieck et al. |
| 2006/0229718 A1 | 10/2006 | Marquez |
| 2006/0229719 A1 | 10/2006 | Marquez et al. |
| 2006/0259133 A1 | 11/2006 | Sowinski et al. |
| 2006/0259136 A1 | 11/2006 | Nguyen et al. |
| 2006/0265053 A1 | 11/2006 | Hunt |
| 2006/0271091 A1 | 11/2006 | Campbell et al. |
| 2006/0276813 A1 | 12/2006 | Greenberg |
| 2006/0276883 A1 | 12/2006 | Greenberg et al. |
| 2006/0276888 A1 | 12/2006 | Lee et al. |
| 2006/0282162 A1 | 12/2006 | Nguyen et al. |
| 2006/0287717 A1 | 12/2006 | Rowe et al. |
| 2006/0287719 A1 | 12/2006 | Rowe et al. |
| 2006/0290027 A1 | 12/2006 | O'Connor et al. |
| 2007/0010876 A1 | 1/2007 | Salahieh et al. |
| 2007/0012624 A1 | 1/2007 | Bacino et al. |
| 2007/0021826 A1 | 1/2007 | Case et al. |
| 2007/0060999 A1 | 3/2007 | Randall et al. |
| 2007/0100435 A1 | 5/2007 | Case et al. |
| 2007/0118210 A1 | 5/2007 | Pinchuk |
| 2007/0129786 A1 | 6/2007 | Beach et al. |
| 2007/0207186 A1 | 9/2007 | Scanlon et al. |
| 2007/0207816 A1 | 9/2007 | Spain, Jr. |
| 2007/0208417 A1 | 9/2007 | Agnew |
| 2007/0208421 A1 | 9/2007 | Quigley |
| 2007/0213800 A1 | 9/2007 | Fierens et al. |
| 2007/0244552 A1 | 10/2007 | Salahieh et al. |
| 2007/0250146 A1 | 10/2007 | Cully et al. |
| 2007/0250153 A1 | 10/2007 | Cully et al. |
| 2007/0254012 A1 | 11/2007 | Ludwig et al. |
| 2008/0009940 A1 | 1/2008 | Cribier |
| 2008/0026190 A1 | 1/2008 | King et al. |
| 2008/0039934 A1 | 2/2008 | Styrc |
| 2008/0051876 A1 | 2/2008 | Ta et al. |
| 2008/0065198 A1 | 3/2008 | Quintessenza |
| 2008/0071369 A1 | 3/2008 | Tuval et al. |
| 2008/0082154 A1 | 4/2008 | Tseng et al. |
| 2008/0097301 A1 | 4/2008 | Alpini et al. |
| 2008/0097401 A1 | 4/2008 | Trapp et al. |
| 2008/0097579 A1 | 4/2008 | Shanley et al. |
| 2008/0097582 A1 | 4/2008 | Shanley et al. |
| 2008/0119943 A1 | 5/2008 | Armstrong et al. |
| 2008/0133004 A1 | 6/2008 | White |
| 2008/0140178 A1 | 6/2008 | Rasmussen et al. |
| 2008/0195199 A1 | 8/2008 | Kheradvar et al. |
| 2008/0208327 A1 | 8/2008 | Rowe |
| 2008/0220041 A1 | 9/2008 | Brito et al. |
| 2008/0228263 A1 | 9/2008 | Ryan |
| 2008/0300678 A1 | 12/2008 | Eidenschink et al. |
| 2008/0319531 A1 | 12/2008 | Doran et al. |
| 2009/0005854 A1 | 1/2009 | Huang et al. |
| 2009/0030499 A1 | 1/2009 | Bebb et al. |
| 2009/0036976 A1 | 2/2009 | Beach et al. |
| 2009/0043373 A1 | 2/2009 | Arnault et al. |
| 2009/0099640 A1 | 4/2009 | Weng |
| 2009/0104247 A1 | 4/2009 | Pacetti |
| 2009/0117334 A1 | 5/2009 | Sogard et al. |
| 2009/0138079 A1 | 5/2009 | Tuval et al. |
| 2009/0157175 A1 | 6/2009 | Benichou |
| 2009/0182413 A1 | 7/2009 | Burkart et al. |
| 2009/0240320 A1 | 9/2009 | Tuval et al. |
| 2009/0264997 A1 | 10/2009 | Salahieh et al. |
| 2009/0276039 A1 | 11/2009 | Meretei |
| 2009/0281609 A1 | 11/2009 | Benichou et al. |
| 2009/0287305 A1 | 11/2009 | Amalaha |
| 2009/0292350 A1 | 11/2009 | Eberhardt et al. |
| 2009/0306762 A1 | 12/2009 | McCullagh et al. |
| 2009/0306766 A1 | 12/2009 | McDermott et al. |
| 2010/0016940 A1 | 1/2010 | Shokoohi et al. |
| 2010/0023114 A1 | 1/2010 | Chambers et al. |
| 2010/0036021 A1 | 2/2010 | Lee et al. |
| 2010/0036484 A1 | 2/2010 | Hariton et al. |
| 2010/0049294 A1 | 2/2010 | Zukowski et al. |
| 2010/0082089 A1 | 4/2010 | Quadri et al. |
| 2010/0082094 A1 | 4/2010 | Quadri et al. |
| 2010/0094394 A1 | 4/2010 | Beach et al. |
| 2010/0094405 A1 | 4/2010 | Cottone |
| 2010/0106240 A1 | 4/2010 | Duggal et al. |
| 2010/0114307 A1 | 5/2010 | Agnew et al. |
| 2010/0131056 A1 | 5/2010 | Lapeyre |
| 2010/0137998 A1 | 6/2010 | Sobrino-Serrano et al. |
| 2010/0145438 A1 | 6/2010 | Barone |
| 2010/0159171 A1 | 6/2010 | Clough |
| 2010/0168839 A1 | 7/2010 | Braido et al. |
| 2010/0185274 A1 | 7/2010 | Moaddeb et al. |
| 2010/0185277 A1 | 7/2010 | Braido et al. |
| 2010/0191320 A1 | 7/2010 | Straubinger et al. |
| 2010/0204781 A1 | 8/2010 | Alkhatib |
| 2010/0204785 A1 | 8/2010 | Alkhatib |
| 2010/0211165 A1 | 8/2010 | Schreck |
| 2010/0217382 A1 | 8/2010 | Chau et al. |
| 2010/0248324 A1 | 9/2010 | Xu et al. |
| 2010/0249923 A1 | 9/2010 | Alkhatib et al. |
| 2010/0256738 A1 | 10/2010 | Berglund |
| 2010/0262231 A1 | 10/2010 | Tuval et al. |
| 2010/0286760 A1 | 11/2010 | Beach et al. |
| 2010/0298931 A1 | 11/2010 | Quadri et al. |
| 2010/0305682 A1 | 12/2010 | Furst |
| 2011/0009953 A1 | 1/2011 | Luk et al. |
| 2011/0040366 A1 | 2/2011 | Goetz et al. |
| 2011/0054515 A1 | 3/2011 | Bridgeman et al. |
| 2011/0064781 A1 | 3/2011 | Cleek et al. |
| 2011/0087318 A1 | 4/2011 | Daugherty et al. |
| 2011/0160836 A1 | 6/2011 | Behan |
| 2011/0172784 A1 | 7/2011 | Richter et al. |
| 2011/0208283 A1 | 8/2011 | Rust |
| 2011/0218619 A1 | 9/2011 | Benichou et al. |
| 2011/0251678 A1 | 10/2011 | Eidenschink et al. |
| 2011/0257739 A1 | 10/2011 | Corbett |
| 2011/0282439 A1 | 11/2011 | Thill et al. |
| 2011/0295363 A1 | 12/2011 | Girard et al. |
| 2012/0035722 A1 | 2/2012 | Tuval |
| 2012/0078357 A1 | 3/2012 | Conklin |
| 2012/0083839 A1 | 4/2012 | Letac et al. |
| 2012/0089223 A1 | 4/2012 | Nguyen et al. |
| 2012/0101567 A1 | 4/2012 | Jansen |
| 2012/0101571 A1 | 4/2012 | Thambar et al. |
| 2012/0116496 A1 | 5/2012 | Chuter et al. |
| 2012/0116498 A1 | 5/2012 | Chuter et al. |
| 2012/0123529 A1 | 5/2012 | Levi et al. |
| 2012/0123530 A1 | 5/2012 | Carpentier et al. |
| 2012/0130468 A1 | 5/2012 | Khosravi et al. |
| 2012/0130471 A1 | 5/2012 | Shoemaker et al. |
| 2012/0185038 A1 | 7/2012 | Fish et al. |
| 2012/0215303 A1 | 8/2012 | Quadri et al. |
| 2012/0253453 A1 | 10/2012 | Bruchman et al. |
| 2012/0277734 A1 | 11/2012 | Goetz et al. |
| 2012/0290082 A1 | 11/2012 | Quint et al. |
| 2012/0323211 A1 | 12/2012 | Ogle et al. |
| 2012/0323315 A1 | 12/2012 | Bruchman et al. |
| 2013/0018456 A1 | 1/2013 | Li et al. |
| 2013/0018458 A1 | 1/2013 | Yohanan et al. |
| 2013/0079700 A1 | 3/2013 | Ballard et al. |
| 2013/0110229 A1 | 5/2013 | Bokeriya et al. |
| 2013/0116655 A1 | 5/2013 | Bacino et al. |
| 2013/0131780 A1 | 5/2013 | Armstrong et al. |
| 2013/0150956 A1 | 6/2013 | Yohanan et al. |
| 2013/0158647 A1 | 6/2013 | Norris et al. |
| 2013/0166021 A1 | 6/2013 | Bruchman et al. |
| 2013/0183515 A1 | 7/2013 | White |
| 2013/0184807 A1 | 7/2013 | Kovach et al. |
| 2013/0197624 A1 | 8/2013 | Armstrong et al. |
| 2013/0204347 A1 | 8/2013 | Armstrong et al. |
| 2013/0204360 A1 | 8/2013 | Gainor |
| 2013/0253466 A1 | 9/2013 | Campbell et al. |
| 2013/0297003 A1 | 11/2013 | Pinchuk |
| 2013/0338755 A1 | 12/2013 | Goetz et al. |
| 2014/0005771 A1 | 1/2014 | Braido et al. |
| 2014/0005773 A1 | 1/2014 | Wheatley |
| 2014/0031924 A1 | 1/2014 | Bruchman et al. |
| 2014/0031927 A1 | 1/2014 | Bruchman et al. |
| 2014/0094898 A1 | 4/2014 | Borck |

(56) References Cited

U.S. PATENT DOCUMENTS

| | | |
|---|---|---|
| 2014/0106951 A1 | 4/2014 | Brandon |
| 2014/0135897 A1 | 5/2014 | Cully et al. |
| 2014/0163671 A1 | 6/2014 | Bruchman et al. |
| 2014/0163673 A1 | 6/2014 | Bruchman et al. |
| 2014/0172066 A1 | 6/2014 | Goepfrich et al. |
| 2014/0172069 A1 | 6/2014 | Roeder et al. |
| 2014/0172077 A1 | 6/2014 | Bruchman et al. |
| 2014/0172078 A1 | 6/2014 | Bruchman et al. |
| 2014/0172079 A1 | 6/2014 | Bruchman et al. |
| 2014/0172082 A1 | 6/2014 | Bruchman et al. |
| 2014/0172083 A1 | 6/2014 | Bruchman et al. |
| 2014/0180400 A1 | 6/2014 | Bruchman et al. |
| 2014/0180402 A1 | 6/2014 | Bruchman et al. |
| 2014/0194968 A1 | 7/2014 | Zukowski |
| 2014/0222140 A1 | 8/2014 | Schreck |
| 2014/0236289 A1 | 8/2014 | Alkhatib |
| 2014/0277413 A1 | 9/2014 | Arnold et al. |
| 2014/0277418 A1 | 9/2014 | Miller |
| 2014/0296969 A1 | 10/2014 | Tegels et al. |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0343670 A1 | 11/2014 | Bakis et al. |
| 2015/0005870 A1 | 1/2015 | Kovach et al. |
| 2015/0018944 A1 | 1/2015 | O'Connell et al. |
| 2015/0088250 A1 | 3/2015 | Zeng et al. |
| 2015/0105856 A1 | 4/2015 | Rowe et al. |
| 2015/0142100 A1 | 5/2015 | Morriss et al. |
| 2015/0157456 A1 | 6/2015 | Armstrong |
| 2015/0157770 A1 | 6/2015 | Cully et al. |
| 2015/0224231 A1 | 8/2015 | Bruchman et al. |
| 2015/0245910 A1 | 9/2015 | Righini et al. |
| 2015/0313871 A1 | 11/2015 | Li et al. |
| 2015/0366663 A1 | 12/2015 | Bruchman et al. |
| 2015/0366664 A1 | 12/2015 | Guttenberg et al. |
| 2016/0001469 A1 | 1/2016 | Baccherei et al. |
| 2016/0015422 A1 | 1/2016 | De Cicco et al. |
| 2016/0074161 A1 | 3/2016 | Bennett |
| 2016/0106537 A1 | 4/2016 | Christianson et al. |
| 2016/0113699 A1 | 4/2016 | Sverdlik et al. |
| 2016/0157998 A1 | 6/2016 | Bruchman et al. |
| 2016/0175095 A1 | 6/2016 | Dienno et al. |
| 2016/0175096 A1 | 6/2016 | Dienno et al. |
| 2016/0206424 A1 | 7/2016 | Al-Jilaihawi et al. |
| 2016/0213465 A1 | 7/2016 | Girard et al. |
| 2016/0235525 A1 | 8/2016 | Rothstein et al. |
| 2016/0250051 A1 | 9/2016 | Lim et al. |
| 2016/0310268 A1 | 10/2016 | Oba et al. |
| 2016/0317299 A1 | 11/2016 | Alkhatib |
| 2017/0027727 A1 | 2/2017 | Wuebbeling et al. |
| 2017/0042674 A1 | 2/2017 | Armstrong |
| 2017/0056169 A1 | 3/2017 | Johnson et al. |
| 2017/0065400 A1 | 3/2017 | Armstrong et al. |
| 2017/0095330 A1 | 4/2017 | Malewicz et al. |
| 2017/0095331 A1 | 4/2017 | Spenser et al. |
| 2017/0100236 A1 | 4/2017 | Robertson et al. |
| 2017/0105854 A1 | 4/2017 | Treacy et al. |
| 2017/0106176 A1 | 4/2017 | Taft et al. |
| 2017/0128199 A1 | 5/2017 | Gurovich et al. |
| 2017/0156859 A1 | 6/2017 | Chang et al. |
| 2017/0165066 A1 | 6/2017 | Rothstein |
| 2017/0165067 A1 | 6/2017 | Barajas-Torres et al. |
| 2017/0216062 A1 | 8/2017 | Armstrong et al. |
| 2017/0224481 A1 | 8/2017 | Spenser et al. |
| 2017/0252153 A1 | 9/2017 | Chau et al. |
| 2017/0348101 A1 | 12/2017 | Vaughn et al. |
| 2018/0021128 A1 | 1/2018 | Bruchman et al. |
| 2018/0021129 A1 | 1/2018 | Peterson et al. |
| 2018/0125646 A1 | 5/2018 | Bruchman et al. |
| 2018/0177583 A1 | 6/2018 | Cully et al. |
| 2018/0221144 A1 | 8/2018 | Bruchman et al. |
| 2018/0271651 A1 | 9/2018 | Christianson et al. |
| 2018/0271653 A1 | 9/2018 | Vidlund et al. |
| 2018/0318070 A1 | 11/2018 | Bruchman et al. |
| 2019/0076245 A1 | 3/2019 | Arcaro et al. |
| 2019/0091014 A1 | 3/2019 | Arcaro et al. |
| 2019/0091015 A1 | 3/2019 | Dienno et al. |
| 2019/0110893 A1 | 4/2019 | Haarer et al. |
| 2019/0125517 A1 | 5/2019 | Cully et al. |
| 2019/0125528 A1 | 5/2019 | Busalacchi et al. |
| 2019/0125530 A1 | 5/2019 | Arcaro et al. |
| 2019/0125531 A1 | 5/2019 | Bennett et al. |
| 2019/0125534 A1 | 5/2019 | Arcaro et al. |
| 2019/0209292 A1 | 7/2019 | Bruchman et al. |
| 2019/0209739 A1 | 7/2019 | Goepfrich et al. |
| 2019/0216592 A1 | 7/2019 | Cully et al. |
| 2019/0247185 A1 | 8/2019 | Gassler |
| 2019/0254815 A1 | 8/2019 | Bruchman et al. |
| 2019/0269505 A1 | 9/2019 | Bruchman et al. |
| 2019/0314154 A1 | 10/2019 | Armstrong |
| 2019/0328525 A1 | 10/2019 | Noe et al. |
| 2019/0374339 A1 | 12/2019 | Bennett |
| 2020/0000578 A1 | 1/2020 | Bruchman et al. |
| 2020/0022828 A1 | 1/2020 | Armstrong et al. |
| 2020/0179663 A1 | 6/2020 | McDaniel et al. |
| 2020/0237497 A1 | 7/2020 | Silverman et al. |
| 2020/0237505 A1 | 7/2020 | Bruchman et al. |
| 2020/0246137 A1 | 8/2020 | Bruchman et al. |
| 2020/0276014 A1 | 9/2020 | Burkart et al. |
| 2020/0323631 A1 | 10/2020 | Chuter et al. |
| 2021/0121289 A1 | 4/2021 | Bruchman et al. |
| 2021/0177589 A1 | 6/2021 | Arcaro et al. |
| 2021/0205074 A1 | 7/2021 | Bruchman et al. |
| 2021/0307905 A1 | 10/2021 | Arcaro et al. |
| 2021/0338422 A1 | 11/2021 | Dienno et al. |
| 2021/0361420 A1 | 11/2021 | Bennett et al. |
| 2021/0393399 A1 | 12/2021 | Arcaro et al. |
| 2022/0000611 A1 | 1/2022 | Arcaro et al. |
| 2022/0023032 A1 | 1/2022 | Bruchman et al. |
| 2022/0183831 A1 | 6/2022 | Burkart et al. |
| 2022/0257369 A1 | 8/2022 | Burkart et al. |
| 2022/0273426 A1 | 9/2022 | Hagaman et al. |
| 2022/0378575 A1 | 12/2022 | Busalacchi et al. |
| 2023/0000623 A1 | 1/2023 | Bennett |

FOREIGN PATENT DOCUMENTS

| | | |
|---|---|---|
| CA | 2297536 A1 | 12/2000 |
| CA | 2462509 A1 | 4/2003 |
| CA | 2849030 A1 | 4/2013 |
| CA | 2878691 A1 | 1/2014 |
| CA | 2964546 A1 | 1/2014 |
| CA | 2960034 A1 | 3/2016 |
| CN | 101057796 A | 10/2007 |
| CN | 101091675 A | 12/2007 |
| CN | 101188985 A | 5/2008 |
| CN | 101374477 A | 2/2009 |
| CN | 101420913 A | 4/2009 |
| CN | 101849863 A | 10/2010 |
| CN | 101902989 A | 12/2010 |
| CN | 101926699 A | 12/2010 |
| CN | 201744060 U | 2/2011 |
| CN | 102015009 A | 4/2011 |
| CN | 102119013 A | 7/2011 |
| CN | 102292053 A | 12/2011 |
| CN | 102438546 A | 5/2012 |
| CN | 102573703 A | 7/2012 |
| CN | 102652694 A | 9/2012 |
| CN | 102724937 A | 10/2012 |
| CN | 102764169 A | 11/2012 |
| CN | 102791223 A | 11/2012 |
| CN | 102883684 A | 1/2013 |
| CN | 103079498 A | 5/2013 |
| CN | 103228232 A | 7/2013 |
| CN | 103237524 A | 8/2013 |
| CN | 103384505 A | 11/2013 |
| CN | 103732183 A | 4/2014 |
| CN | 103781439 A | 5/2014 |
| CN | 103945796 A | 7/2014 |
| CN | 104114127 A | 10/2014 |
| CN | 104487023 A | 4/2015 |
| CN | 104507417 A | 4/2015 |
| CN | 104869948 A | 8/2015 |
| CN | 105007955 A | 10/2015 |

(56) References Cited

FOREIGN PATENT DOCUMENTS

| | | |
|---|---|---|
| CN | 105101911 A | 11/2015 |
| CN | 105263445 A | 1/2016 |
| CN | 105662651 A | 6/2016 |
| CN | 105792780 A | 7/2016 |
| CN | 106668949 A | 5/2017 |
| CN | 106714733 A | 5/2017 |
| CN | 106794065 A | 5/2017 |
| CN | 107106294 A | 8/2017 |
| CN | 107690323 A | 2/2018 |
| CN | 108578016 A | 9/2018 |
| DE | 212013000104 U1 | 11/2014 |
| EP | 0293090 A2 | 11/1988 |
| EP | 0313263 A2 | 4/1989 |
| EP | 0582870 A2 | 2/1994 |
| EP | 0775472 A2 | 5/1997 |
| EP | 0815806 A2 | 1/1998 |
| EP | 0893108 A2 | 1/1999 |
| EP | 1057460 A1 | 12/2000 |
| EP | 1318775 A1 | 6/2003 |
| EP | 1666003 A1 | 6/2006 |
| EP | 1395205 B1 | 7/2008 |
| EP | 1235537 B1 | 12/2008 |
| EP | 2193762 A1 | 6/2010 |
| EP | 2255750 A2 | 12/2010 |
| EP | 2400923 A1 | 1/2012 |
| EP | 2489331 A2 | 8/2012 |
| EP | 2359774 B1 | 1/2013 |
| EP | 2591100 A2 | 5/2013 |
| EP | 2109417 B1 | 11/2013 |
| EP | 3142608 A1 | 3/2017 |
| EP | 3797738 A1 | 3/2021 |
| EP | 2948103 B1 | 12/2022 |
| FR | 2591100 A1 | 6/1987 |
| GB | 2312485 A | 10/1997 |
| GB | 2513194 A | 10/2014 |
| JP | 44-032400 | 12/1969 |
| JP | 1969-032400 B | 12/1969 |
| JP | 02-000645 A | 1/1990 |
| JP | 09-241412 A | 9/1997 |
| JP | 10-507097 A | 7/1998 |
| JP | 11-290448 A | 10/1999 |
| JP | 11-512635 A | 11/1999 |
| JP | 2000-511459 A | 9/2000 |
| JP | 2000-513248 A | 10/2000 |
| JP | 2001-000460 A | 1/2001 |
| JP | 2001-508641 A | 7/2001 |
| JP | 2001-508681 A | 7/2001 |
| JP | 2001-509702 A | 7/2001 |
| JP | 2001-511030 A | 8/2001 |
| JP | 2002-525169 A | 8/2002 |
| JP | 2002-541915 A | 12/2002 |
| JP | 2004-510471 A | 4/2004 |
| JP | 2005-500101 A | 1/2005 |
| JP | 2005-512611 A | 5/2005 |
| JP | 2005-514108 A | 5/2005 |
| JP | 2007-525291 A | 9/2007 |
| JP | 2007-526098 A | 9/2007 |
| JP | 2007-536989 A | 12/2007 |
| JP | 2008-506459 A | 3/2008 |
| JP | 2008-535572 A | 9/2008 |
| JP | 4335487 B2 | 9/2009 |
| JP | 2010-500107 A | 1/2010 |
| JP | 2010-504174 A | 2/2010 |
| JP | 2010-517623 A | 5/2010 |
| JP | 2010-528761 A | 8/2010 |
| JP | 2010-188189 A | 9/2010 |
| JP | 2010-535075 A | 11/2010 |
| JP | 2010-536527 A | 12/2010 |
| JP | 2012-504031 A | 2/2012 |
| JP | 2012-152563 A | 8/2012 |
| JP | 2013-506439 A | 2/2013 |
| JP | 2013-543399 A | 12/2013 |
| JP | 2014-513585 A | 6/2014 |
| JP | 2014-517720 A | 7/2014 |
| JP | 2015-523168 A | 8/2015 |
| JP | 2016-501104 A | 1/2016 |
| JP | 2016-501115 A | 1/2016 |
| JP | 2016-509932 A | 4/2016 |
| JP | 2016-510645 A | 4/2016 |
| JP | 2016-512753 A | 5/2016 |
| JP | 2016-518948 A | 6/2016 |
| JP | 2017-527397 A | 9/2017 |
| JP | 2018-079352 A | 5/2018 |
| JP | 6392778 B2 | 9/2018 |
| JP | 6802300 B2 | 12/2020 |
| RU | 2124986 C1 | 1/1999 |
| RU | 2434604 C1 | 11/2011 |
| WO | 94/13224 A1 | 6/1994 |
| WO | 94/16802 A1 | 8/1994 |
| WO | 95/05555 A1 | 2/1995 |
| WO | 95/09586 A1 | 4/1995 |
| WO | 96/02212 A1 | 2/1996 |
| WO | 96/07370 A1 | 3/1996 |
| WO | 96/40348 A1 | 12/1996 |
| WO | 97/10871 A1 | 3/1997 |
| WO | 99/26558 A1 | 6/1999 |
| WO | 00/18333 A1 | 4/2000 |
| WO | 00/41649 A1 | 7/2000 |
| WO | 00/47271 A1 | 8/2000 |
| WO | 00/62716 A1 | 10/2000 |
| WO | 01/28453 A2 | 4/2001 |
| WO | 01/41679 A1 | 6/2001 |
| WO | 01/64278 A1 | 9/2001 |
| WO | 01/74272 A2 | 10/2001 |
| WO | 02/07795 A2 | 1/2002 |
| WO | 02/24118 A1 | 3/2002 |
| WO | 02/24119 A1 | 3/2002 |
| WO | 02/45933 A2 | 6/2002 |
| WO | 02/47468 A1 | 6/2002 |
| WO | 02/60506 A1 | 8/2002 |
| WO | 2002/100301 A1 | 12/2002 |
| WO | 03/03946 A1 | 1/2003 |
| WO | 03/07795 A2 | 1/2003 |
| WO | 03/47468 A1 | 6/2003 |
| WO | 03/90834 A2 | 11/2003 |
| WO | 2004/000375 A1 | 12/2003 |
| WO | 2005/084595 A1 | 9/2005 |
| WO | 2005/112827 A2 | 12/2005 |
| WO | 2006/019626 A2 | 2/2006 |
| WO | 2006/058322 A2 | 6/2006 |
| WO | 2006/108090 A2 | 10/2006 |
| WO | 2007/016251 A2 | 2/2007 |
| WO | 2008/021002 A1 | 2/2008 |
| WO | 2008/028964 A2 | 3/2008 |
| WO | 2008/036870 A2 | 3/2008 |
| WO | 2008/049045 A2 | 4/2008 |
| WO | 2008/052421 A1 | 5/2008 |
| WO | 2008/091589 A1 | 7/2008 |
| WO | 2008/021006 A3 | 8/2008 |
| WO | 2008/097589 A1 | 8/2008 |
| WO | 2008/097592 A2 | 8/2008 |
| WO | 2008/150529 A1 | 12/2008 |
| WO | 2009/017827 A1 | 2/2009 |
| WO | 2009/029199 A1 | 3/2009 |
| WO | 2009/045332 A2 | 4/2009 |
| WO | 2009/100210 A1 | 8/2009 |
| WO | 2009/108355 A1 | 9/2009 |
| WO | 2010/006783 A1 | 1/2010 |
| WO | 2010/008570 A1 | 1/2010 |
| WO | 2010/030766 A1 | 3/2010 |
| WO | 2010/037141 A1 | 4/2010 |
| WO | 2010/057262 A1 | 5/2010 |
| WO | 2010/086460 A1 | 8/2010 |
| WO | 2010/132707 A1 | 11/2010 |
| WO | 2010/150208 A2 | 12/2010 |
| WO | 2011/098565 A1 | 8/2011 |
| WO | 2011/109450 A1 | 9/2011 |
| WO | 2011/109801 A2 | 9/2011 |
| WO | 2011/112706 A2 | 9/2011 |
| WO | 2012/004460 A2 | 1/2012 |
| WO | 2012/011261 A1 | 1/2012 |
| WO | 2012/040643 A2 | 3/2012 |
| WO | 2012/047644 A1 | 4/2012 |
| WO | 2012/065080 A2 | 5/2012 |

(56) References Cited

FOREIGN PATENT DOCUMENTS

| | | | |
|---|---|---|---|
| WO | 2012/082952 | A2 | 6/2012 |
| WO | 2012/099979 | A1 | 7/2012 |
| WO | 2012/110767 | A2 | 8/2012 |
| WO | 2012/116368 | A2 | 8/2012 |
| WO | 2012/135603 | A2 | 10/2012 |
| WO | 2012/158944 | A1 | 11/2012 |
| WO | 2012/167131 | A1 | 12/2012 |
| WO | 2013/074663 | A2 | 5/2013 |
| WO | 2013/074990 | A1 | 5/2013 |
| WO | 2013/096854 | A2 | 6/2013 |
| WO | 2013/109337 | A1 | 7/2013 |
| WO | 2014/018189 | A2 | 1/2014 |
| WO | 2014/018432 | A2 | 1/2014 |
| WO | 2014/099150 | A1 | 6/2014 |
| WO | 2014/099163 | A1 | 6/2014 |
| WO | 2014/099722 | A1 | 6/2014 |
| WO | 2014/144937 | A2 | 9/2014 |
| WO | 2014/149319 | A1 | 9/2014 |
| WO | 2014/181188 | A2 | 11/2014 |
| WO | 2014210124 | A1 | 12/2014 |
| WO | 2015/045002 | A1 | 4/2015 |
| WO | 2015/085138 | A1 | 6/2015 |
| WO | 2015/171743 | A2 | 11/2015 |
| WO | 2015/173794 | A1 | 11/2015 |
| WO | 2016/028591 | A1 | 2/2016 |
| WO | 2016/044223 | A1 | 3/2016 |
| WO | 2016/100913 | A1 | 6/2016 |
| WO | 2016/172349 | A1 | 10/2016 |
| WO | 2016/186909 | A1 | 11/2016 |
| WO | 2017/038145 | A1 | 3/2017 |
| WO | 2017/096157 | A1 | 6/2017 |
| WO | 2017218375 | A1 | 12/2017 |
| WO | 2018029680 | A1 | 2/2018 |
| WO | 2019/067219 | A1 | 4/2019 |
| WO | 2019/067220 | A1 | 4/2019 |
| WO | 2019/074607 | A1 | 4/2019 |
| WO | 2019/074869 | A1 | 4/2019 |
| WO | 2019/089138 | A1 | 5/2019 |
| WO | 2019/246268 | A1 | 12/2019 |

OTHER PUBLICATIONS

International Preliminary Report on Patentability received for PCT Patent Application No. PCT/US2020/044603, mailed on Feb. 10, 2022, 9 pages.
International Search Report and Written Opinion received for PCT Patent Application No. PCT/US2020/044603, mailed on Oct. 20, 2020, 12 pages.
Google Image Search Results, "S-Shaped", accessed Nov. 1, 2013.
International Preliminary Report on Patentability received for PCT Patent Application No. PCT/US15/50113, mailed on Mar. 30, 2017, 9 pages.
International Preliminary Report on Patentability received for PCT Patent Application No. PCT/US2020/027921, mailed on Oct. 21, 2021, 11 pages.
International Search Report and Written Opinion received for PCT Patent Application No. PCT/US2020/027921, mailed on Jul. 24, 2020, 16 pages.
Nakayama, Yasuhide. Microporous Stent Achieves Brain Aneurysm Occlusion Without Disturbing Branching Flow. NeuroNews Nov. 2012; 8:1-2.
Nishi S, Nakayama Y, Ishibashi-Ueda FI, Okamoto Y, Yoshida M. Development of microporous self-expanding stent grafts for treating cerebral aneurysms: designing micropores to control intimal hyperplasia. J Artif Organs 2011; 14:348-356.
Cardiac Surgery in the Adult, Third Edition, Chapter 2 2008.
Clough, Norman E. Introducing a New Family of Gore ePTFE Fibers (2007), pp. 1-10.
English translation of RU2434604 (C1), filed 30.04.2010, translation powered by EPO and Google, 8 pages.
EPO Form 1002 for EP16196687.4 Filed Dec. 28, 2016.
International Search Report and Written Opinion from PCT/US2018/050768, mailed Dec. 17, 2018, 12 pages.
International Search Report and Written Opinion from PCT/US2018/050786 mailed Dec. 14, 2018, 13 pages.
Mano Thubrikar, "The Aortic Valve", Chapter 1: Geometry of the Aortic Valve, CRC Press, Inc., Informa Healthcare, 2011, 40 pages.
Norman E. Clough. Introducing a New Family of Gore (Trademark) ePTFE Fibers (2007).
Opposition from EP16196687.4, mailed on Dec. 12, 2019, 38 pages.
Opposition from EP17187595.8, filed Sep. 12, 2019, 50 pages.

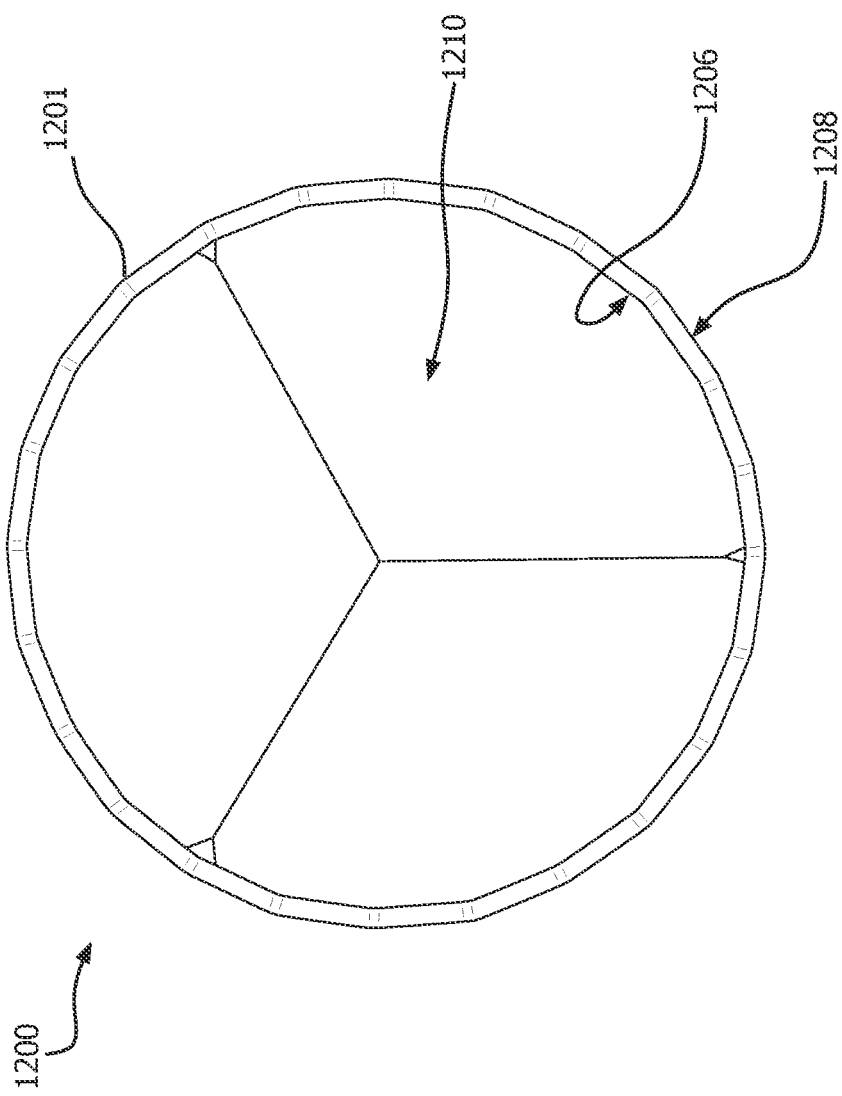

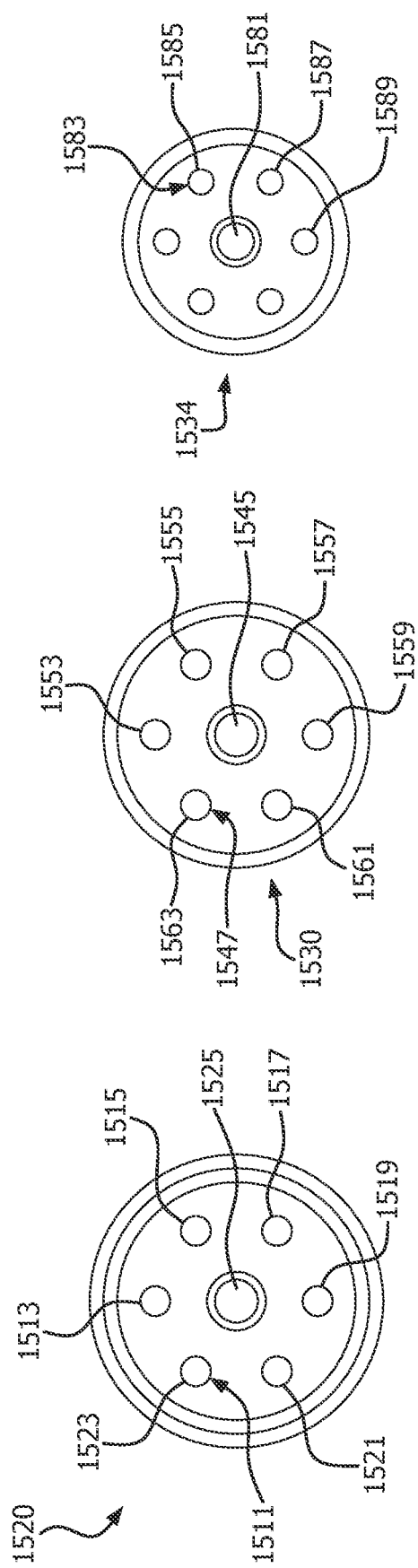
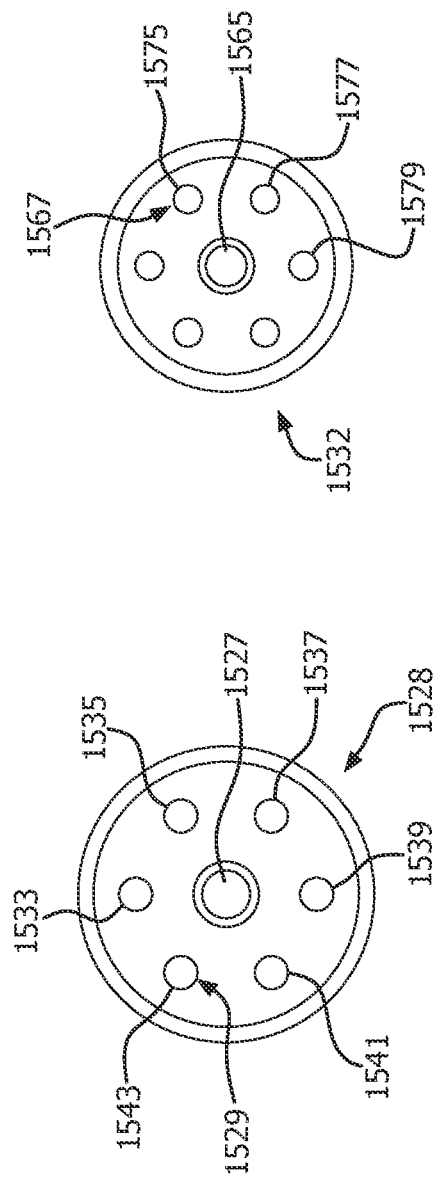

TELESCOPING PROSTHETIC VALVE AND DELIVERY SYSTEM

CROSS-REFERENCE TO RELATED APPLICATION

This application is a continuation of U.S. application Ser. No. 16/129,779, filed Sep. 12, 2018, which claims the benefit of U.S. Provisional Application No. 62/572,281, filed Oct. 13, 2017, and U.S. Provisional Application No. 62/579,762, filed Oct. 31, 2017, all of which are incorporated herein by reference in their entireties for all purposes.

FIELD

The present disclosure relates generally to prosthetic valves and more specifically to flexible leaflet-type prosthetic valve devices, systems and methods.

BACKGROUND

Bioprosthetic valves have been developed that attempt to mimic the function and performance of a native valve. Bioprosthetic valves may be formed from synthetic materials, natural tissue such as biological tissue, or a combination of synthetic materials and natural tissue.

Though many conventional designs require delivery to a target region within a patient's anatomy via open-heart surgical techniques, alternative approaches such as transcatheter techniques offer a number of advantages. Among other examples, a transcatheter prosthetic valve that is delivered endovascularly via a catheter can help to minimize patient trauma as compared with an open-heart, surgical procedure. Open-heart surgery involves extensive trauma to the patient, with attendant morbidity and extended recovery. On the other hand, a valve delivered to the recipient site via a catheter avoids the trauma of open-heart surgery and may be performed on patients too ill or feeble to survive the open-heart surgery.

However, challenges exist with accessing treatment regions within the anatomy, properly positioning the bioprosthesis for deployment, and depending on the particular anatomy being repaired or augmented, modifications of the surrounding anatomy may arise as a consequence of the presence of the bioprosthesis. In some instances, such consequential modifications to the surrounding anatomy may negatively impact a patient's health.

SUMMARY

According to one example, ("Example 1"), a prosthetic valve for replacing a native valve of a patient's anatomy includes an anchor frame subcomponent, a valve frame subcomponent nestable within the anchor frame subcomponent, a tissue retention feature configured to engage tissue associated with the native valve and secure the leaflet of the native valve between the valve frame subcomponent and the anchor frame subcomponent.

According to another example, ("Example 2") further to Example 1, one or more portions of the anchor frame subcomponent and the valve frame subcomponent overlap one another such that an annular space is defined between the overlapping portions of the valve frame subcomponent and the anchor frame subcomponent when the valve frame subcomponent is nested with the anchor frame subcomponent.

According to another example, ("Example 3") further to Example 2, the tissue retention feature is configured to secure the tissue associated with the native valve within the annular space.

According to another example, ("Example 4") further to Example 3, the tissue associated with the native valve includes a leaflet of the native valve.

According to another example, ("Example 5") further to Examples 2-4, a portion of the tissue retention feature extends radially outwardly from the valve frame subcomponent into the annular space defined between the valve frame subcomponent and the anchor frame subcomponent when the valve frame subcomponent is nested with the anchor frame subcomponent.

According to another example, ("Example 6") further to Examples 1-5, the tissue retention feature is integral with the valve frame subcomponent.

According to another example, ("Example 7") further to Examples 1-6, the tissue retention feature is distinct from and coupled to the valve frame subcomponent.

According to another example, ("Example 8") further to Examples 1-7, the prosthetic valve further includes a film disposed about one or more portions of the valve frame subcomponent and the anchor frame subcomponent such that the anchor frame subcomponent is coupled to the valve frame subcomponent at least in part by a contiguous portion of the film.

According to another example, ("Example 9") further to Example 8, a portion of the contiguous portion of the film is contained between the valve frame subcomponent and anchor frame subcomponent when the valve frame subcomponent is nested within the anchor frame subcomponent.

According to another example, ("Example 10") further to Example 9, the tissue retention feature is positioned between the valve frame subcomponent and the film when the valve frame subcomponent is nested with the anchor frame subcomponent.

According to another example, ("Example 11") further to Examples 1-10, the prosthetic valve further includes an interlock configured to maintain a nested position of the valve frame subcomponent within the anchor frame subcomponent.

According to another example, ("Example 12") further to Example 11, the interlock is coupled to the valve frame subcomponent and is configured to engage the anchor frame subcomponent.

According to another example, ("Example 13") further to Examples 11-12, the interlock is a resilient member that is transitionable between a deflected and extended position as the anchor frame subcomponent and the valve frame subcomponent are nested together.

According to another example, ("Example 14") further to Examples 1-13, the prosthetic valve further includes one or more anchors configured for anchoring the prosthetic valve to tissue of the patient's anatomy.

According to another example, ("Example 15") further to Example 14, the anchors are integral with the anchor frame subcomponent.

According to another example, ("Example 16") further to Example 14, the anchors are coupled to the anchor frame subcomponent.

According to another example, ("Example 17") further to Examples 1-16, the prosthetic valve is transitionable between a compressed configuration for transcatheter delivery and an expanded configuration wherein the prosthetic valve is operable to replace a native valve of a patient's anatomy.

According to another example, ("Example 18"), a prosthetic valve transitionable between a delivery configuration and a deployed configuration in-situ includes a valve frame subcomponent comprising a proximal end and a distal end, an anchor frame subcomponent coupled to the valve frame subcomponent, the anchor frame subcomponent comprising a proximal end and a distal end, and a tissue retention feature configured to engage tissue associated with a native valve of a patient's anatomy and secure the tissue of the native valve between the valve frame subcomponent and the anchor frame subcomponent. When situated in the delivery configuration, the valve frame subcomponent and the anchor frame subcomponent are longitudinally offset from one another such that the proximal end of the valve frame subcomponent is situated distal of the distal end of the anchor frame subcomponent. When transitioned to the deployed configuration in-situ, the valve frame subcomponent is nested within an interior region defined by the anchor frame subcomponent.

According to another example, ("Example 19") further to Example 18, the tissue associated with the native valve includes a leaflet of the native valve.

According to another example, ("Example 20") further to Examples 18-19, the proximal end of the valve frame subcomponent is situated proximal of the distal end of the anchor frame subcomponent when the prosthetic is transitioned to the deployed configuration in-situ.

According to another example, ("Example 21") a medical device system includes a catheter, and a prosthetic valve. The prosthetic valve includes a valve frame subcomponent having a proximal end and a distal end, an anchor frame subcomponent coupled to the valve frame subcomponent, the anchor frame subcomponent comprising a proximal end and a distal end, and a tissue retention feature configured to engage tissue associated with a native valve of a patient's anatomy and secure the tissue between the valve frame subcomponent and the anchor frame subcomponent. The prosthetic valve is situated along the catheter in a delivery configuration such that the valve frame subcomponent and the anchor frame subcomponent are longitudinally offset from one another such that the proximal end of the valve frame subcomponent is situated distal of the distal end of the anchor frame subcomponent. The prosthetic valve is transitionable to a deployed configuration in-situ such that the valve frame subcomponent is nested within an interior region defined by the anchor frame subcomponent such that the tissue retention feature secures the leaflet of the native valve between the valve frame subcomponent and the anchor frame subcomponent.

According to another example, ("Example 22") further to Example 21, the tissue associated with the native valve includes a leaflet of the native valve.

According to another example, ("Example 23") a method of augmenting a native valve of a patient's anatomy includes providing a prosthetic valve including an anchor frame subcomponent, a valve frame subcomponent nestable within the anchor frame subcomponent, and a tissue retention feature configured to engage tissue associated with the native valve and secure the tissue between the valve frame subcomponent and the anchor frame subcomponent. The method further includes advancing the prosthetic valve in a delivery configuration to a treatment site within a patient's anatomy, wherein when in the delivery configuration the valve frame subcomponent and the anchor frame subcomponent are longitudinally offset from one another such that a proximal end of the valve frame subcomponent is situated distal of a distal end of the anchor frame subcomponent. The method further includes nesting the valve frame subcomponent within the anchor frame subcomponent by changing a relative position between the valve frame subcomponent and the anchor frame subcomponent such that the tissue retention feature engages the tissue associated with the native valve and secures the tissue between the valve frame subcomponent and the anchor frame subcomponent.

According to another example, ("Example 24") further to Example 23, the tissue associated with the native valve includes a leaflet of the native valve.

According to another example, ("Example 25") further to Examples 23-24, the valve frame subcomponent is nested with the outer fame such that the proximal end of the valve frame subcomponent is situated proximal of the distal end of the anchor frame subcomponent.

According to another example, ("Example 26") further to Examples 23-25, the method further includes deploying the prosthetic valve at the treatment site.

According to another example, ("Example 27") further to Examples 23-26, the valve frame subcomponent is nested within the anchor frame subcomponent after the prosthetic valve is deployed at the treatment site.

According to another example, ("Example 28") further to Examples 23-27, the prosthetic valve is advanced to the treatment site via a catheter.

According to another example, ("Example 29") further to Examples 23-28, nesting the valve frame subcomponent within the anchor frame subcomponent includes drawing the valve frame subcomponent proximally relative to the anchor frame subcomponent.

According to another example, ("Example 30") further to Examples 23-29, the method further includes securing the prosthetic valve to a valve orifice of the native valve such that the prosthetic valve is operable to transition between an open position wherein fluid flow is permitted, and a closed position wherein fluid flow is obstructed.

According to one example, ("Example 1a"), a delivery system for a prosthetic valve includes a support portion configured to support a first frame and a second frame situated in series such that the first frame and the second frame are longitudinally offset from one another. The delivery system further includes a plurality of locking elements including a first locking element and second locking element. The delivery system further includes a first constraining element disposed about the first frame and operable to maintain the first frame in a delivery configuration, wherein the first constraining element is releasably engaged with the first locking element. The delivery system further includes a second constraining element disposed about the second frame and operable to maintain the second frame in a delivery configuration, wherein the second constraining element is releasbly engaged with the second locking element, and wherein the first and second locking elements are operable to independent release the first and second constraining elements.

According to another example, ("Example 2a") further to Example 1a, the delivery system further includes a plurality of guide elements including first guide element and a second guide element, wherein the first constraint extends through a portion of the first guide element and the second constraint extends through the second guide element.

According to another example, ("Example 3a") further to Example 2a, the first locking element extends through the first guide element.

According to another example, ("Example 4a") further to any of Examples 2a and 3a, the anchor frame subcomponent is supported at least, at least in part, by the first guide element, and wherein the valve frame subcomponent is supported, at least in part, by the second guide element.

According to another example, ("Example 5a") further to any of the preceding examples, the first frame and the second frame are longitudinally offset from one another such that a proximal end of the valve frame subcomponent is situated distal of a distal end of the anchor frame subcomponent.

According to another example, ("Example 6a") a method of delivering a prosthetic valve, includes providing a prosthetic valve that includes an anchor frame subcomponent, and a valve frame subcomponent nestable within the anchor frame subcomponent. The method further includes providing a delivery system that includes a first constraint and a second constraint, and a first locking element secured to the first constraint and a second locking element secured to the second constraint, wherein the prosthetic valve is loaded on the delivery system such that the valve frame subcomponent and the anchor frame subcomponent are longitudinally offset from one another. The method further includes releasing the first constraint from the first locking element such that the anchor frame subcomponent expands from a delivery configuration to a deployed configuration, and after the anchor frame subcomponent has expanded, advancing the delivery system relative to the anchor frame subcomponent such that the valve frame subcomponent is advanced relative to the anchor frame subcomponent. The method further includes nesting the valve frame subcomponent within the anchor frame subcomponent, and thereafter, releasing the first constraint from the first locking element such that the valve frame subcomponent expands from a delivery configuration to a deployed configuration.

According to another example, ("Example 7a") further to Example 6, the valve frame subcomponent and the anchor frame subcomponent are longitudinally offset from one another such that a proximal end of the valve frame subcomponent is situated distal of a distal end of the anchor frame subcomponent.

According to another example, ("Example 8a") further to any of Examples 6a and 7a, the first constraint is release from the first locking element by proximally withdrawing the first locking element.

According to another example, (Example 99) further to any of the preceding examples, the prosthetic valve of any one of the preceding examples, further comprises an interstage defining a tube coupling a proximal end of the valve frame subcomponent to a distal end of the anchor frame subcomponent, wherein the interstage is everted when the valve frame subcomponent is transitioned from an un-nested position to a nested position.

According to another example, (Example 99) further to any of the preceding examples, the prosthetic valve of any one of the preceding examples, further comprises an interstage defining a tube coupling a proximal end of the valve frame subcomponent to a distal end of the anchor frame subcomponent, wherein the interstage comprises an inner film layer that defines an inner surface of the interstage and an outer film layer that defines an outer surface of the interstage, the inner film layer and the outer film layer being coupled together at least at the proximal end of the valve frame subcomponent and the distal end of the anchor frame subcomponent, the inner frame film defining at least one inner aperture therethrough adjacent the anchor frame subcomponent and the outer film layer defines at least one outer aperture therethrough adjacent the valve frame subcomponent, the inner film layer and the outer film layer being not coupled at least between one of the inner apertures and one of the outer apertures so as to define a flow space therebetween operable to permit blood flow therethrough when the valve frame subcomponent is not nested in the anchor frame subcomponent, and is operable to restrict flow when the valve frame subcomponent is nested within the anchor frame subcomponent.

According to another example, (Example 99) further to any of the preceding examples, the prosthetic valve of any one of the preceding examples, further comprises interconnecting struts coupling the proximal end of the valve frame subcomponent to the distal end of the anchor frame subcomponent operate to maintain the nested configuration of the anchor frame subcomponent and the valve frame subcomponent.

According to another example, (Example 99) further to any of the preceding examples, the prosthetic valve of any one of the preceding examples, further comprises a continuous sinuous element coupled to the interstage between but not coupled to the proximal end of the valve frame subcomponent to the distal end of the anchor frame subcomponent operate to maintain the nested configuration of the anchor frame subcomponent and the valve frame subcomponent.

According to another example, (Example 99), a prosthetic valve transitionable between a delivery configuration and a deployed configuration in-situ, the prosthetic valve comprises a valve frame subcomponent comprising a proximal end and a distal end, an anchor frame subcomponent comprising a proximal end and a distal end, and an interstage defining a tube coupling the proximal end of the valve frame subcomponent to the distal end of the anchor frame subcomponent, wherein when situated in the delivery configuration, the valve frame subcomponent and the anchor frame subcomponent are longitudinally offset from one another such that the proximal end of the valve frame subcomponent is situated distal of the distal end of the anchor frame subcomponent, wherein when transitioned to the deployed configuration in-situ, the interstage is everted and the valve frame subcomponent is nested within an interior region defined by the anchor frame subcomponent.

According to another example, (Example 99) further to the previous example, the interstage comprises an inner film layer that defines an inner surface of the interstage and an outer film layer that defines an outer surface of the interstage, the inner film layer and the outer film layer being coupled together at least at the proximal end of the valve frame subcomponent and the distal end of the anchor frame subcomponent, the inner frame film defining at least one inner aperture therethrough adjacent the anchor frame subcomponent and the outer film layer defines at least one outer aperture therethrough adjacent the valve frame subcomponent, the inner film layer and the outer film layer being not coupled at least between one of the inner apertures and one of the outer apertures so as to define a flow space therebetween operable to permit blood flow therethrough when the valve frame subcomponent is not nested in the anchor frame subcomponent, and is operable to restrict flow when the valve frame subcomponent is nested within the anchor frame subcomponent.

According to another example, (Example 99) further to any one of examples 99 and 99, further comprising interconnecting struts coupling the proximal end of the valve frame subcomponent to the distal end of the anchor frame subcomponent operate to maintain the nested configuration of the anchor frame subcomponent and the valve frame subcomponent.

According to another example, (Example 99) further to any one of examples 99 and 99, further comprising a continuous sinuous element coupled to the interstage between but not coupled to the proximal end of the valve frame subcomponent to the distal end of the anchor frame subcomponent operate to maintain the nested configuration of the anchor frame subcomponent and the valve frame subcomponent.

According to another example, (Example 99) further to any of the preceding examples, the prosthetic valve of any one of the preceding examples, further comprises a plurality of leaflets coupled to the valve frame subcomponent operable to open to allow forward flow therethrough and to occlude the valve frame subcomponent to prevent retrograde flow, wherein the leaflets comprise a composite material including a porous synthetic fluoropolymer membrane defining pores and an elastomer or elastomeric material filling the pores; and a TFE-PMVE copolymer comprising from about 27 to about 32 weight percent perfluoromethyl vinyl ether and respectively from about 73 to about 68 weight percent tetrafluoroethylene on at least a portion of the composite material.

According to another example, (Example 100) further to any of the preceding examples, the prosthetic valve of any one of the preceding examples, further comprises, wherein the interstage comprises an inner film layer that defines an inner surface of the interstage and an outer film layer that defines an outer surface of the interstage, the inner film layer and the outer film layer being coupled together at least at the proximal end of the valve frame subcomponent and the distal end of the anchor frame subcomponent, the inner frame film defining at least one inner aperture therethrough adjacent the anchor frame subcomponent and the outer film layer defines at least one outer aperture therethrough adjacent the valve frame subcomponent, the inner film layer and the outer film layer being not coupled at least between one of the inner apertures and one of the outer apertures so as to define a flow space therebetween operable to permit blood flow therethrough when the valve frame subcomponent is not nested in the anchor frame subcomponent, and is operable to restrict flow when the valve frame subcomponent is nested within the anchor frame subcomponent.

According to another example, (Example 101) further to any of the preceding examples, the interstage further comprising a nesting retention element operable to maintain the nested configuration of the anchor frame subcomponent and the valve frame subcomponent.

According to another example, (Example 102) further to any of the preceding examples, the interstage further comprising a nesting retention element in the form of interconnecting struts coupling the proximal end of the valve frame to the distal end of the anchor frame operable to maintain the nested configuration of the anchor frame subcomponent and the valve frame subcomponent.

According to another example, (Example 103) further to any of the preceding examples, the interstage further comprising a nesting retention element in the form of a continuous sinuous element coupled to the interstage between but not coupled to the proximal end of the valve frame or the distal end of the anchor frame operable to maintain the nested configuration of the anchor frame subcomponent and the valve frame subcomponent.

According to another example, (Example 104) further to any of the preceding examples, the interstage further comprising a nesting retention element in the form of a plurality of elongated elements coupled to the interstage between but not coupled to the proximal end of the valve frame or the distal end of the anchor frame operable to maintain the nested configuration of the anchor frame subcomponent and the valve frame subcomponent.

According to another example, (Example 105) further to any of the preceding examples, the interstage further comprising a film or fabric comprising elongated stiffening features operable to maintain the nested configuration of the anchor frame subcomponent and the valve frame subcomponent.

According to another example, (Example 106) further to any of the preceding examples, the anchor frame further comprising a plurality of tissue anchoring elements operable to engage tissue.

According to another example, (Example 107) further to any of the preceding examples, the, further comprising a plurality of leaflets coupled to the valve frame operable to open to allow forward flow therethrough and to occlude the valve frame subcomponent to prevent retrograde flow, wherein the leaflets comprise a composite material including a porous synthetic fluoropolymer membrane defining pores and an elastomer or elastomeric material filling the pores, and TFE-PMVE copolymer comprising from about 27 to about 32 weight percent perfluoromethyl vinyl ether and respectively from about 73 to about 68 weight percent tetrafluoroethylene on at least a portion of the composite material.

According to another example, (Example 108) a prosthetic valve transitionable between a delivery configuration and a deployed configuration in-situ, the prosthetic valve comprising: a leaflet frame subcomponent comprising a proximal end and a distal end; an anchor frame subcomponent having a proximal end and a distal end; and interstage coupled to the leaflet frame subcomponent and the anchor frame subcomponent, the anchor frame subcomponent comprising a proximal end and a distal end, wherein when situated in the delivery configuration, the leaflet frame subcomponent and the anchor frame subcomponent are longitudinally offset from one another such that the proximal end of the leaflet frame subcomponent is situated distal of the distal end of the anchor frame subcomponent, and wherein when transitioned to the deployed configuration in-situ, the leaflet frame subcomponent is nested within an interior region defined by the anchor frame subcomponent, wherein when transitioned to the deployed configuration in-situ the proximal end of the leaflet frame subcomponent is situated proximal of the distal end of the anchor frame subcomponent.

While multiple embodiments are disclosed, still other embodiments will become apparent to those skilled in the art from the following detailed description, which shows and describes illustrative examples. Accordingly, the drawings and detailed description are to be regarded as illustrative in nature and not restrictive.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

FIG. 2B is an axial view of a valve frame subcomponent of the medical device of FIG. 2A, according to some embodiments;

FIG. 10 is a sectional view taken along line 10-10 in FIG. 10, according to some embodiments;

FIG. 11 is a sectional view taken along line 11-11 in FIG. 10, according to some embodiments;

FIG. 12 is a sectional view taken along line 12-12 in FIG. 10, according to some embodiments;

FIG. 13 is a sectional view taken along line 13-13 in FIG. 10, according to some embodiments;

FIG. 14 is a sectional view taken along line 14-14 in FIG. 10, according to some embodiments.

DETAILED DESCRIPTION

Figure 1A:
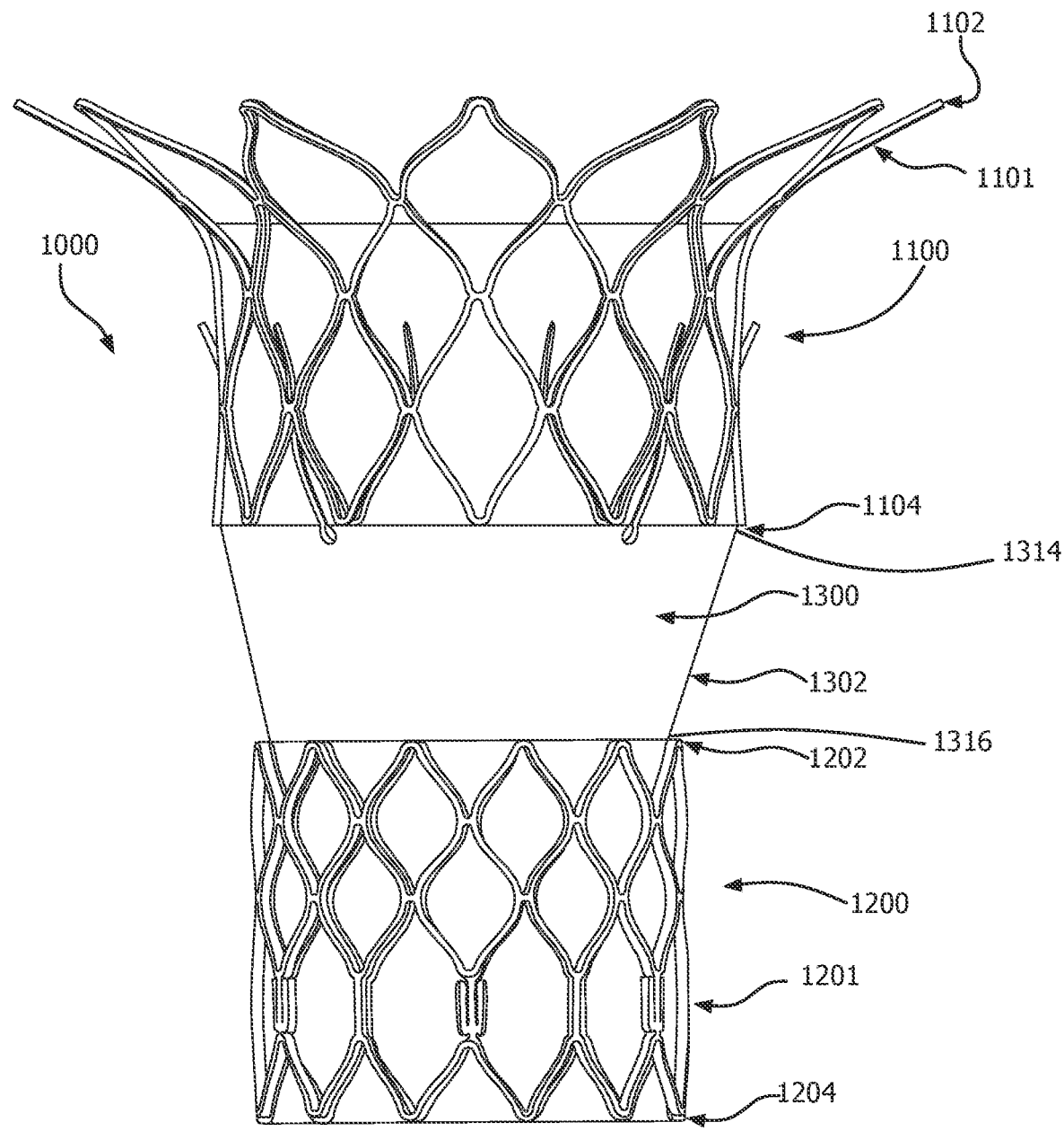
FIG. 1A is a side view a prosthetic valve, according to some embodiments.

The present disclosure relates to prosthetic valves used for cardiac valve replacement or other applications associated with native valve or other valve orifices, and related systems, methods, and apparatuses. In various examples, the prosthetic valve is operable as a one-way prosthetic valve that defines a valve orifice into which leaflets open to permit flow and close so as to block or occlude the valve orifice and partially or entirely prevent flow in response to differential fluid pressure. Examples presented herein provide a prosthetic valve that includes a valve frame subcomponent, an anchor frame subcomponent, and an interstage therebetween. The valve frame subcomponent further includes leaflets that operate as a one-way valve. The anchor frame subcomponent is operable to couple to an implant site. The interstage is operable to permit the translation of the valve frame subcomponent into the anchor frame subcomponent during deployment. Further, in accordance with some embodiments, the interstage is operable to permit perfusion during deployment.

In the instant disclosure, the examples are primarily described in association with surgical or transcatheter cardiac valve applications, although it should be readily appreciated embodiments within the scope of this disclosure can be applied toward any prosthetic valve or mechanism of similar structure and/or function. For example, the prosthetic valve 1000 of FIG. 1 can be applied in non-cardiac applications, such as respiratory or gastrointestinal tract applications. As used herein, "prosthetic valve orifice" refers to a location into which the prosthetic valve may be placed. A prosthetic valve orifice includes a tissue orifice which includes anatomical structures into which a prosthetic valve can be placed. Such anatomical structures include, but are not limited to, a location wherein a cardiac valve may or may not have been surgically removed. Other anatomical structures that can receive a prosthetic valve include, but are not limited to, veins, arteries, ducts and shunts. A prosthetic valve orifice may also refer to a location in a synthetic or biological conduit that may receive a prosthetic valve.

The term "leaflet" as used in the context of prosthetic valves is generally a flexible component operable to move between an open and closed position under the influence of pressure differentials. For example, in operation, the leaflets open when an inflow fluid pressure exceeds an outflow fluid pressure and close when the outflow fluid pressure exceeds the inflow fluid pressure. In a closed position, the leaflet, alone or in combination with one or more other leaflets, operates to substantially restrict or obstruct (or alternatively completely obstruct) retrograde flow through the prosthetic valve. Thus, it will be appreciated that, in some instances, coaptation of adjacent leaflets may operate to completely block the flow of fluid (e.g., blood) through the prosthetic valve, while in other instances coaptation of adjacent leaflets may operate to block less than all of the flow of fluid (e.g., blood) through the prosthetic valve. In some embodiments, the leaflets include a free edge, and the free edges of adjacently situated leaflets coapt under the influence of outflow fluid pressure, thereby closing the valve so as to restrict or obstruct fluid from flowing retrograde through the prosthetic valve.

As will be describe further below, in various examples, the prosthetic valve provides a valve frame subcomponent that essentially floats within an anchor frame subcomponent supported by the interstage and does not directly couple with a prosthetic valve orifice. The anchor frame subcomponent may conform to the shape of the prosthetic valve orifice whereas the valve frame subcomponent does not necessarily conform to the shape of the prosthetic valve orifice. The valve frame subcomponent may remain cylindrical or at a preferred geometrical configuration so as to present the leaflets with a geometrically stable platform ensuring proper leaflet function, including coaptation and opening dynamics.

In various embodiments, the prosthetic valve is configured to stow or capture one or more of the native leaflets of a native valve being replaced by the prosthetic valve. Such a configuration provides for a system that minimizes the consequential occlusive effect of the implanted prosthetic valve on downstream or antegrade anatomy distal to the prosthetic valve, as discussed in greater detail herein.

Although it is appreciated that the examples of the prosthetic valve may be suitable for either surgical or transcatheter applications, examples provided herein are presented as for transcatheter applications to avoid the repetition if surgical examples are also presented. Therefore, the inventive concepts are applicable for both surgical or transcatheter applications and not limited to only transcatheter applications.

Figure 1B:
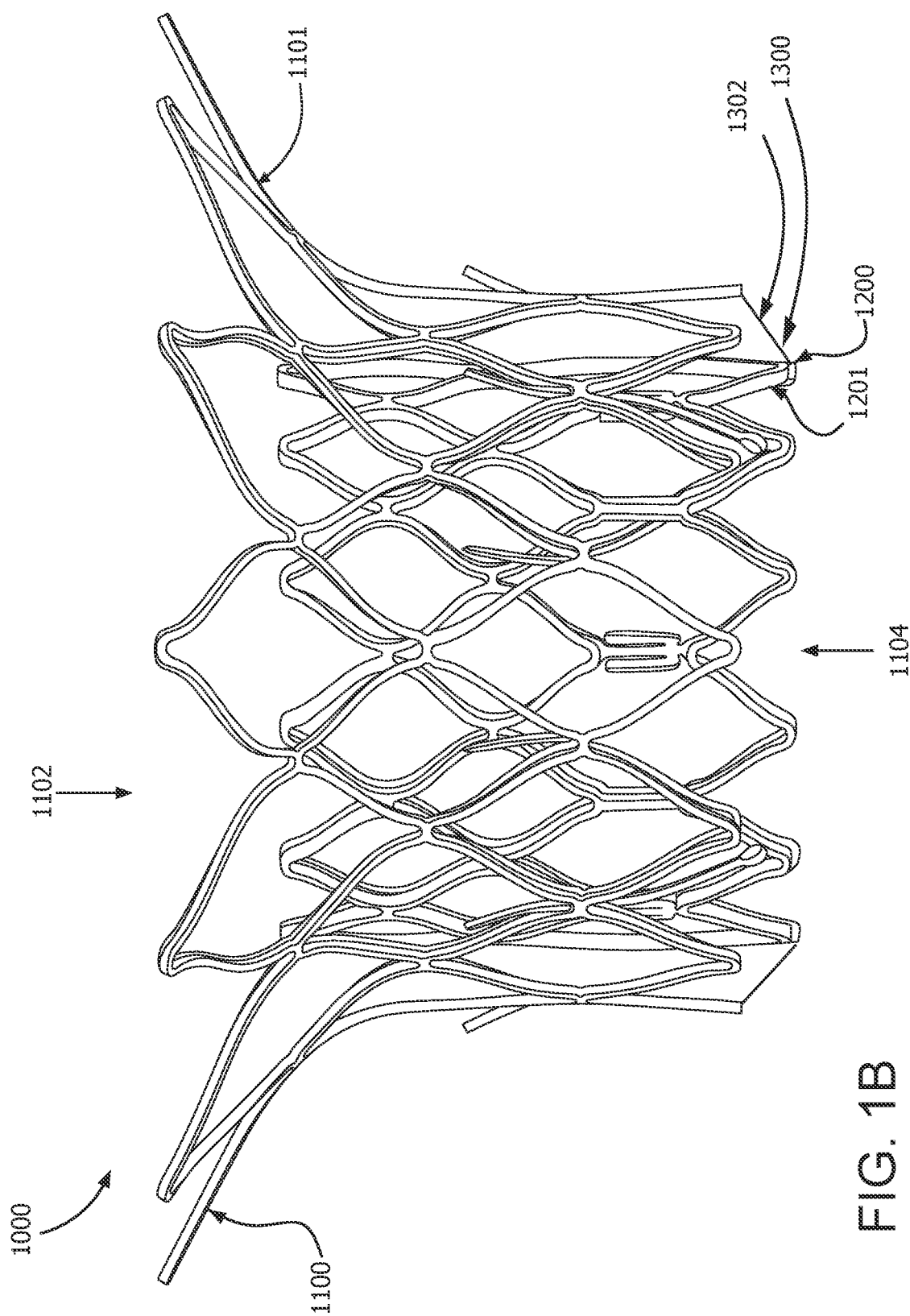
FIG. 1B is a side view of a prosthetic valve, according to some embodiments.

Various embodiments illustrated and described herein are directed to a prosthetic valve that comprises a valve frame subcomponent 1200 and an anchor frame subcomponent 1100 that can be nested in-situ. FIG. 1A is a side view of the prosthetic valve 1000 in the pre-deployed configuration showing a valve frame subcomponent 1200, an anchor frame subcomponent 1100, and an interstage 1302 therebetween in coaxial serial alignment. FIG. 1B is a side view of the prosthetic valve 1000 in the deployed configuration showing the valve frame subcomponent 1200 translated into the anchor frame subcomponent 1100, with the interstage 1302 therebetween in nested alignment.

Valve Frame Subcomponent

The valve frame subcomponent 1200 provides the prosthetic valve 1000 with the functionality of a one-way valve. It is understood and appreciated that one-way valves are well known in the art and may be used herein. It is appreciated that mechanical valves, biological valves, and biological and synthetic leaflet valves may be used as the one-way valve of the valve frame subcomponent 1200. It is also appreciated that, for transcatheter applications, the valve frame subcomponent 1200 is required to have a smaller-diameter compressed configuration and a larger-diameter expanded configuration, and that the one-way valve component must be able to accommodate that functionality.

The valve frame subcomponent 1200 is configured to be received within at least a portion of the anchor frame subcomponent 1100, as will be described in more detail below. It will be appreciated that nonlimiting examples of valve frame subcomponents 1200 can be provided with a diameter (e.g., a diameter of an interior or exterior surface of the valve frame subcomponent 1200) in a range of between twenty (20) millimeters and thirty (30) millimeters, depending on a patient's anatomy.

Figure 2A:
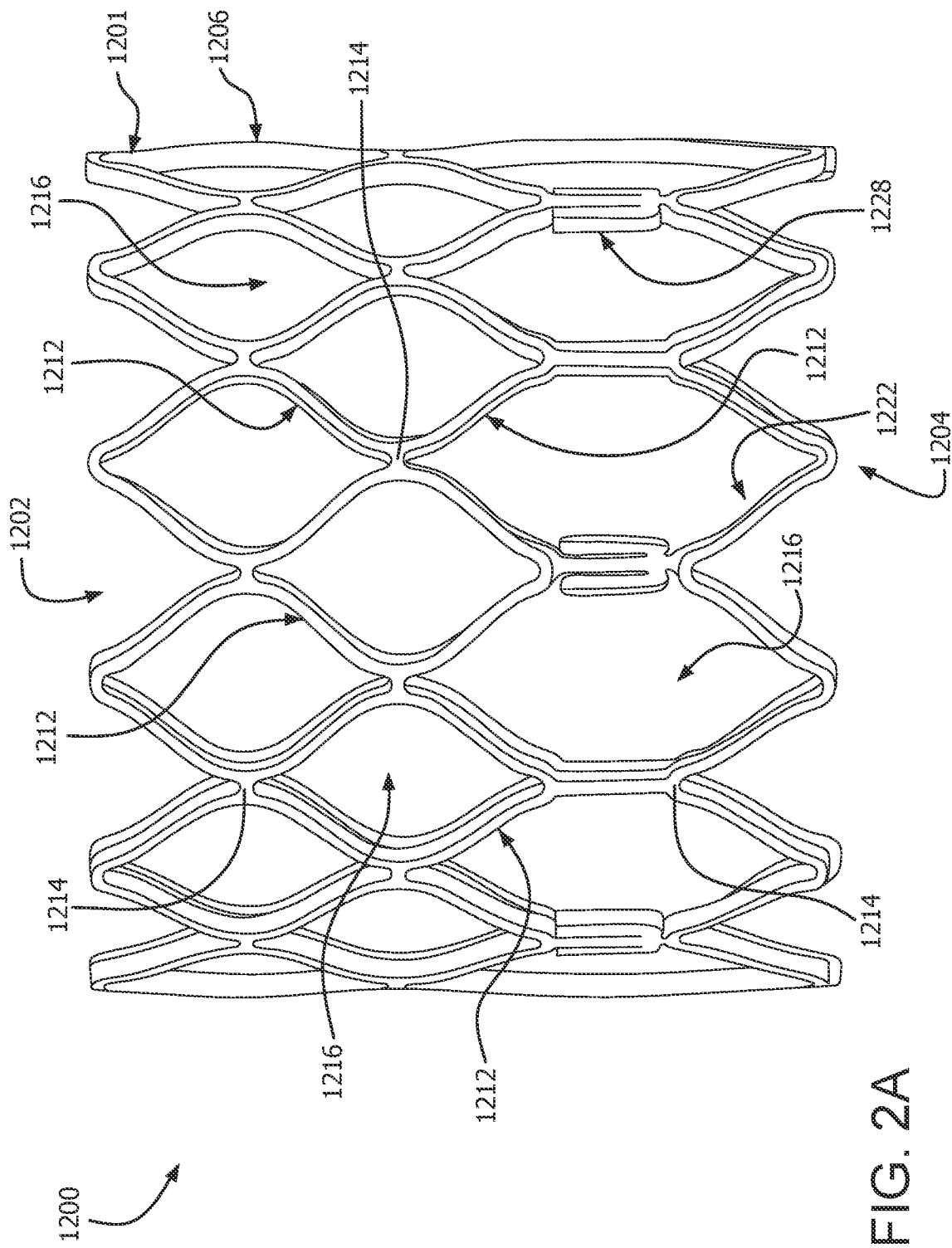
FIG. 2A is a side view of a valve frame subcomponent of a medical device, according to some embodiments.

FIG. 2A is a side view of the valve frame 1201 without leaflets 1210 shown for clarity. FIG. 2B is an axial view of the valve frame 1201 showing the leaflets 1210 therein. The side of the valve frame 1201 may be at least partially covered, such as with a film or fabric, not shown for clarity, suitable for a particular purpose, such as to restrict fluid from passing through the valve frame 1201. For illustrative purposes, the following examples are suitable especially for a transcatheter application, but are also suitable for a surgical application. The valve frame subcomponent 1200 includes a valve frame 1201 and leaflets 1210.

The valve frame 1201 defines a cylindrical or tubular mesh having a framework defining apertures. For example, as shown, the valve frame 1201 includes a plurality of frame members 1212 that are interconnected and arranged in one or more patterns. In various examples, the frame members 1112 are connected to one another at various joints 1214. In some examples, these joints 1214 operate as flex points so as to provide a preferential flexing location for the valve frame subcomponent 1200, such as to flex when compressed to a smaller delivery diameter such as required for transcatheter delivery. In some examples, a flex point or joint 1214 comprises a site on the valve frame 1201 that undergoes a high degree of bending. In some examples, the flex points or joints 1214 may comprise a geometry, structural modification or material modification, among others, that biases the valve frame 1201 to bend at the joint 1214 when compressed or expanded between a larger diameter and a smaller.

In some examples, one or more closed cell apertures or voids 1216 are defined between the joints 1214 and the interconnected frame members 1212 of the valve frame subcomponent 1200. In some examples, these apertures or voids 1216 extend from the exterior surface 1208 to the interior surface 1206 of the valve frame subcomponent 1200. As illustrated in the embodiments of FIGS. 2A and 2B, one or more of the apertures or voids 1216 define a diamond shape when the valve frame subcomponent 1200 is in a deployed configuration. Upon compression to a smaller diameter (e.g., a delivery diameter), one or more of the joints 1214 and the frame members 1212 deform such that the apertures or voids 1216 generally define an elongated diamond shape (e.g., as shown generally in FIG. 4). Upon re-expanding the valve frame subcomponent 1200 to a larger diameter during deployment at a treatment site, the apertures or voids 1216 re-expand to define the generally wider diamond shape.

It should be appreciated that while the frame members 1212 illustrated and described herein are interconnected and define apertures or voids 1216 having generally a diamond shape, the interconnected frame members 1212 may be arranged in a number of alternative patterns without departing from the spirit or scope of the disclosure. That is, a number of alternative patterns are envisioned where the arrangement of frame members 1212 is configured in such a manner as to provide for an valve frame subcomponent 1200 that can be compressed to a smaller diameter for transcatheter delivery and subsequently expanded (or allowed to expand) to a larger diameter at a treatment site during deployment of the prosthetic valve 1000. Accordingly, the disclosure should not be limited to arrangements of the frame members 1212 that define diamond-shaped apertures or voids 1216. For example, a framework of the valve frame subcomponent 1200 can define any number of features, repeatable or otherwise, such as geometric shapes and/or linear or meandering series of sinusoids. Geometric shapes can comprise any shape that facilitates circumferential compressibility and expandability.

In various embodiments, the valve frame subcomponent 1200 may comprise or otherwise be formed from a cut tube, or any other element suitable for the particular purpose of the valve frame subcomponent 1200 as described herein. In some examples, the valve frame subcomponent 1200 may be etched, cut, laser cut, or stamped into a tube or a sheet of material, with the sheet then formed into a substantially cylindrical structure. Alternatively, an elongated material, such as a wire, bendable strip, or a series thereof, can be bent or braided and formed into a substantially cylindrical structure wherein the walls of the cylinder comprise an open framework that is compressible to a smaller diameter in a generally uniform and circumferential manner and expandable to a larger diameter as illustrated and described herein.

The valve frame subcomponent 1200 may comprise, such as, but not limited to, any elastically deformable metallic or polymeric biocompatible material, in accordance with embodiments. The valve frame subcomponent 1200 may comprise a shape-memory material, such as nitinol, a nickel-titanium alloy. Other materials suitable for the valve frame subcomponent 1200 include, but are not limited to, other titanium alloys, stainless steel, cobalt-nickel alloy, polypropylene, acetyl homopolymer, acetyl copolymer, other alloys or polymers, or any other biocompatible material having adequate physical and mechanical properties to function as a valve frame subcomponent 1200 as described herein.

In various examples, as the valve frame subcomponent 1200 is elastically deformable so as to be self-expanding under spring loads, as those of skill will appreciate. In some examples, the valve frame subcomponent 1200 is plastically deformable so as to be mechanically expanded such as with a balloon, as those of skill will appreciate. In yet some other examples, the valve frame subcomponent 1200 is plastically deformable as well as elastically deformable. That is, in some examples, the valve frame subcomponent 1200 includes one or more elastically deformable components or features and one or more plastically deformable components or features. Thus, it should be appreciated that the examples of the valve frame subcomponent 1200 presented herein are not to be limited to a specific design or mode of expansion.

In accordance with some embodiments, the valve frame subcomponent 1200 comprises a shape memory material operable to flex under load and retain its original shape when the load is removed, thus allowing the valve frame subcomponent 1200 to self-expand from a compressed shape to a predetermined shape. The valve frame subcomponent 1200 and the anchor frame subcomponent 1100 may comprise the same or different materials. In accordance with an embodiment, the valve frame subcomponent 1200 is plastically deformable to be expanded by a balloon. In another embodiment the valve frame subcomponent 1200 is elastically deformable so as to be self-expanding.

Anchor Frame Subcomponent

Figure 3A:
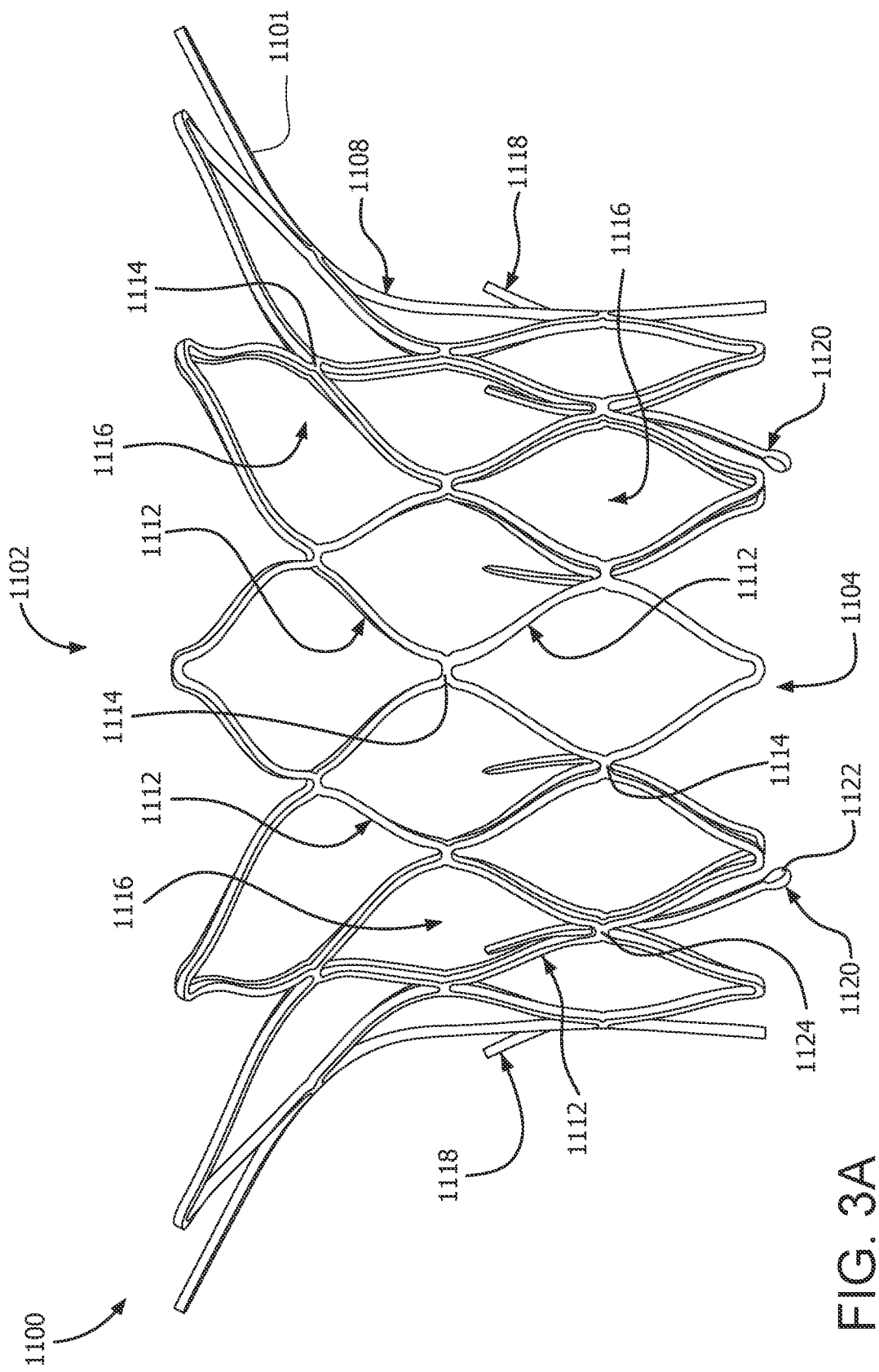
FIG. 3A is a side view of an anchor frame subcomponent of a medical device, according to some embodiments.
Figure 3B:
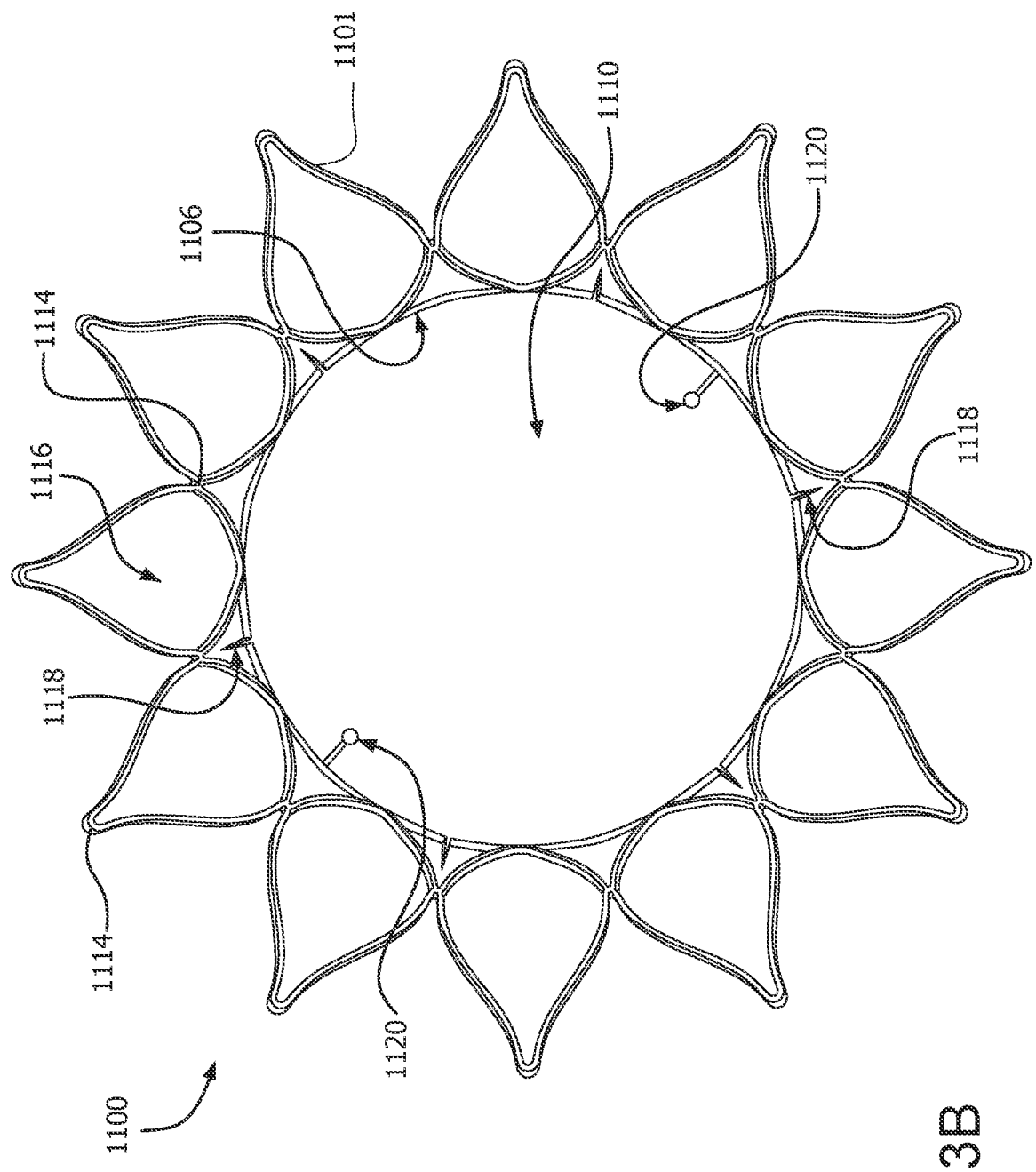
FIG. 3B is an axial view of the anchor frame subcomponent of the medical device of FIG. 3A, according to some embodiments.

FIG. 3A is a side view of the anchor frame 1101. FIG. 3B is an axial view of the anchor frame 1100. The anchor frame subcomponent 1100 includes an anchor frame 1101. The side of the anchor frame 1101 may be at least partially covered, such as with a film or fabric, not shown for clarity, suitable for a particular purpose, such as to restrict fluid from passing through the anchor frame 1101, or to encourage tissue ingrowth at the implant site. For illustrative purposes, the following examples are suitable especially for a transcatheter application, but are also suitable for a surgical application.

In accordance with some embodiments, the anchor frame subcomponent 1100 comprises a shape memory material operable to flex under load and retain its original shape when the load is removed, thus allowing the anchor frame subcomponent 1100 to self-expand from a compressed shape to a predetermined larger shape. The anchor frame subcomponent 1100 may comprise the same or different materials as the valve frame subcomponent 1200. In accordance with an embodiment, the anchor frame subcomponent 1100 is plastically deformable to be expanded by a balloon. In another embodiment the anchor frame subcomponent 1100 is elastically deformable so as to be self-expanding.

Interstage

Referring to FIG. 1A, the interstage 1300 includes a conduit 1302 that couples to an anchor frame distal end 1104 of the anchor frame 1100 at an interstage proximal end 1314 and couples to a leaflet frame proximal end 1202 at an interstage distal end 1316. The conduit 1302 may comprise any suitable material known in the art. By way of example, the conduit 1302 may be a film, fabric, among others. Although the term "film" is use throughout this disclosure, it is understood that the term includes film, fabric, and other suitable materials.

Figure 7A:
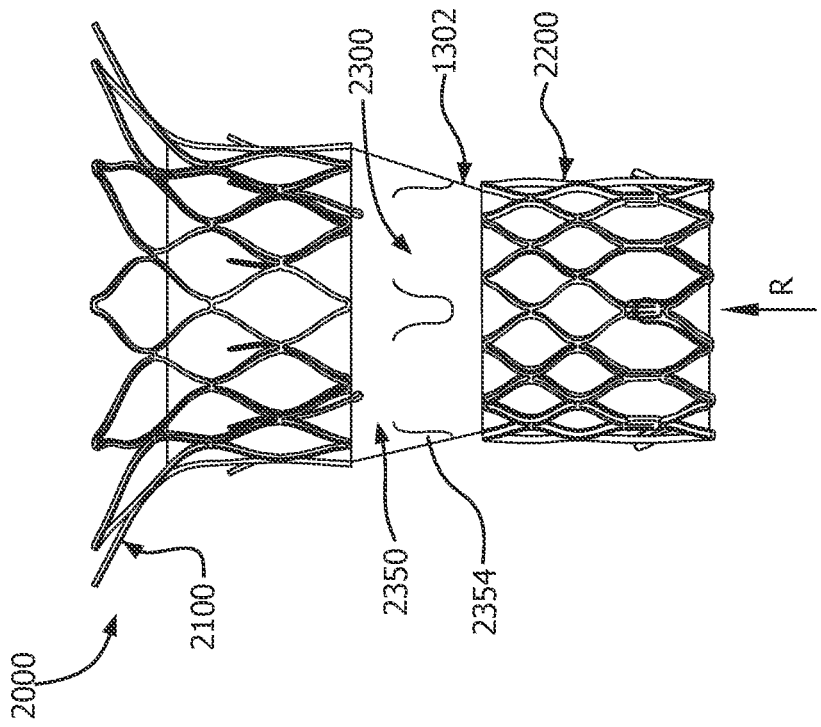
FIG. 7A is a front view of a prosthetic valve with flow enabling features in an open configuration, according to some embodiments.
Figure 7B:
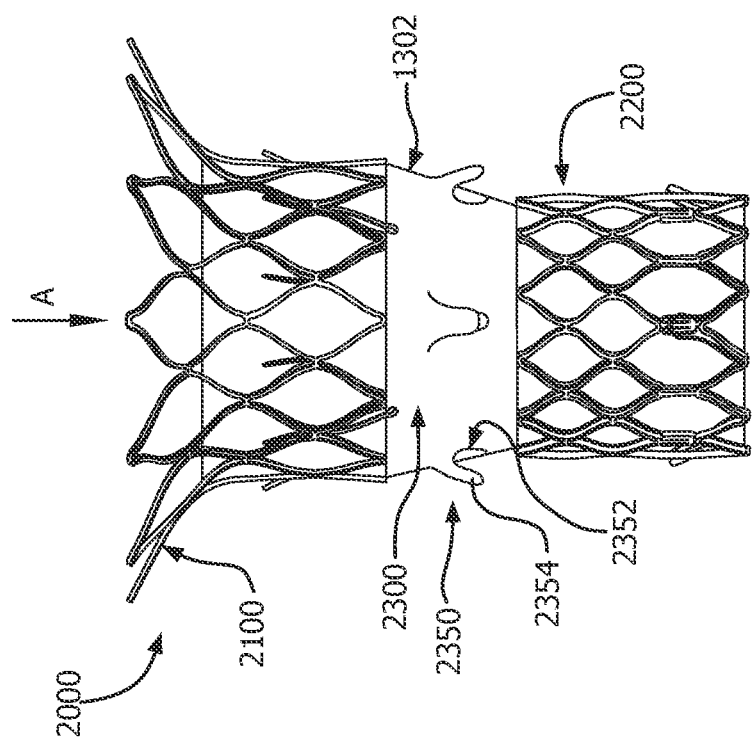
FIG. 7B is a front view of the prosthetic valve of FIG. 7A with the flow enabling features in a closed configuration, according to some embodiments.
Figure 7C:
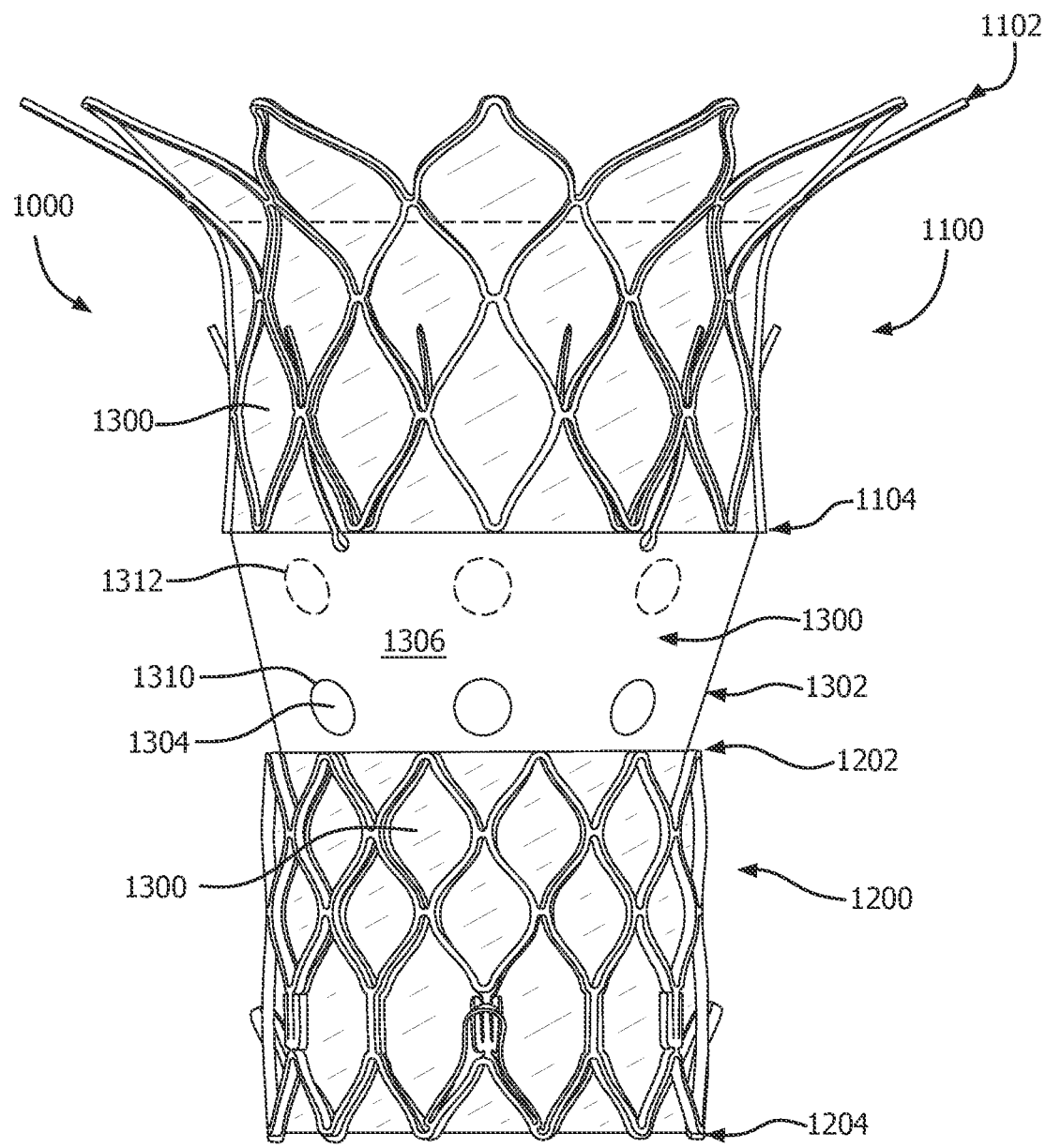
FIG. 7C is a front view of a prosthetic valve with flow enabling features, according to some embodiments.

In various examples, the interstage 1300 further comprises a nesting retention element 1330, such as shown in FIGS. 7C-7E, to be described below, that is operable to retain the valve frame subcomponent 1200 as nested in the anchor frame subcomponent 1100. Examples of nesting retention elements 1330 are provided below. In accordance with some examples, the nesting retention elements 1330 may be elongated elements that bias the interstage 1300 in the nesting position. In accordance with an embodiment, the nesting retention elements 1330 are caused to evert during the deployment process of translating the valve frame subcomponent 1200 into the anchor frame subcomponent 1100. The nesting retention elements 1330 are provided with a predetermined stiffness or other property sufficient to permit eversion during deployment but not under normal biological forces. In accordance with another embodiment, the nesting retention elements 1330 are sized such that, when the anchor frame subcomponent 1100 is expanded and the valve frame subcomponent is compressed, the nesting retention elements 1330 are able to rotate lengthwise from a forward facing orientation to a backward facing orientation. When the valve frame subcomponent 1200 is expanded, the nesting retention elements 1330 have a profile or length that prevents the nesting retention elements 1330 from rotating or flipping back to a forward facing orientation. In other words, the gap between the anchor frame subcomponent 1100 and the valve frame subcomponent 1200 is too narrow to allow end over end rotation of the nesting retention elements 1330. The nesting retention elements 1330 are provided with a predetermined stiffness or other property sufficient to prevent eversion of the nesting retention elements 1330 within the gap between the anchor frame subcomponent 1100 and the valve frame subcomponent 1200 under normal biological forces.

Figure 1C:
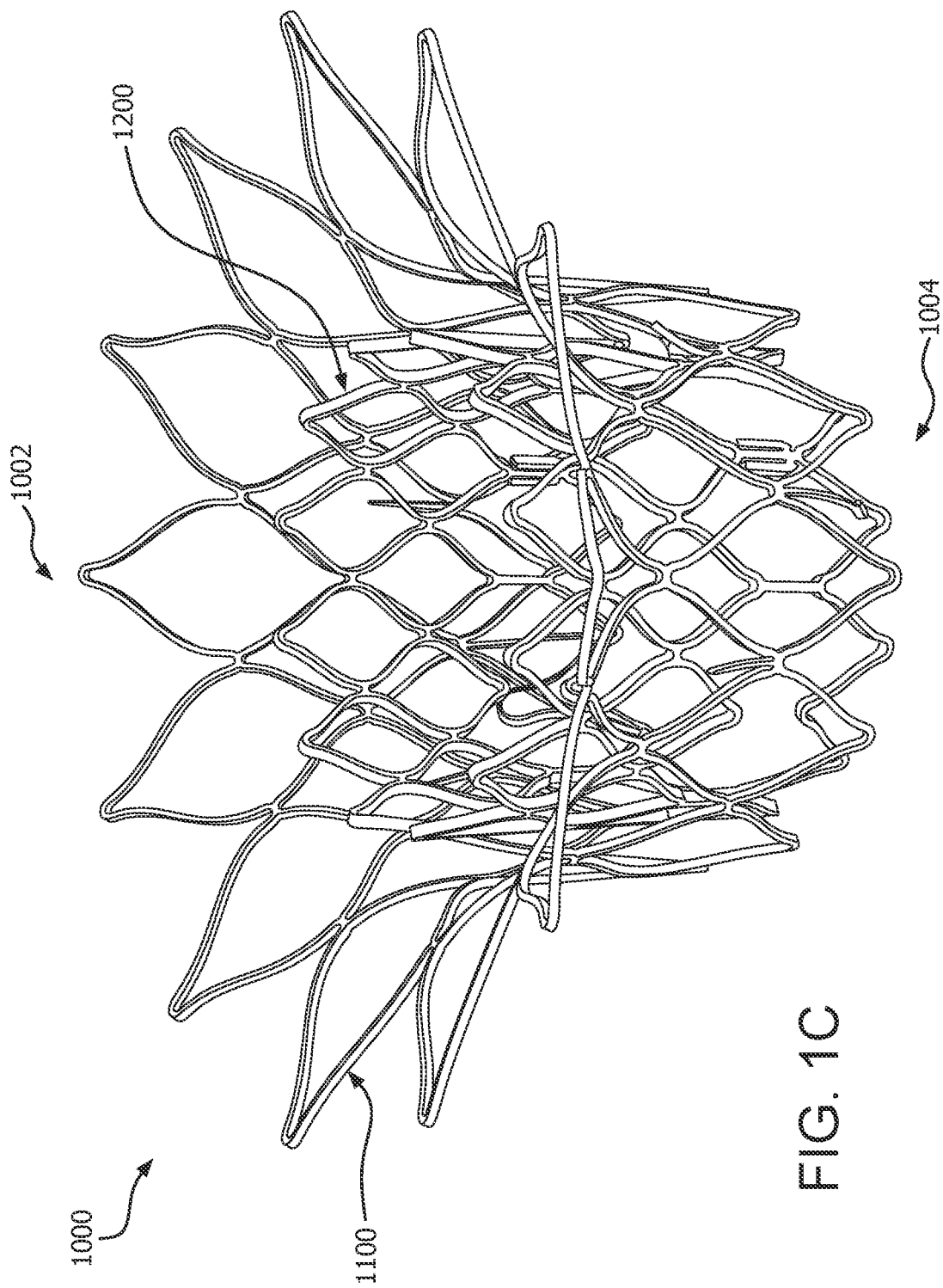
FIG. 1C is a perspective view of the prosthetic valve of FIG. 1A, according to some embodiments.
Figure 1D:
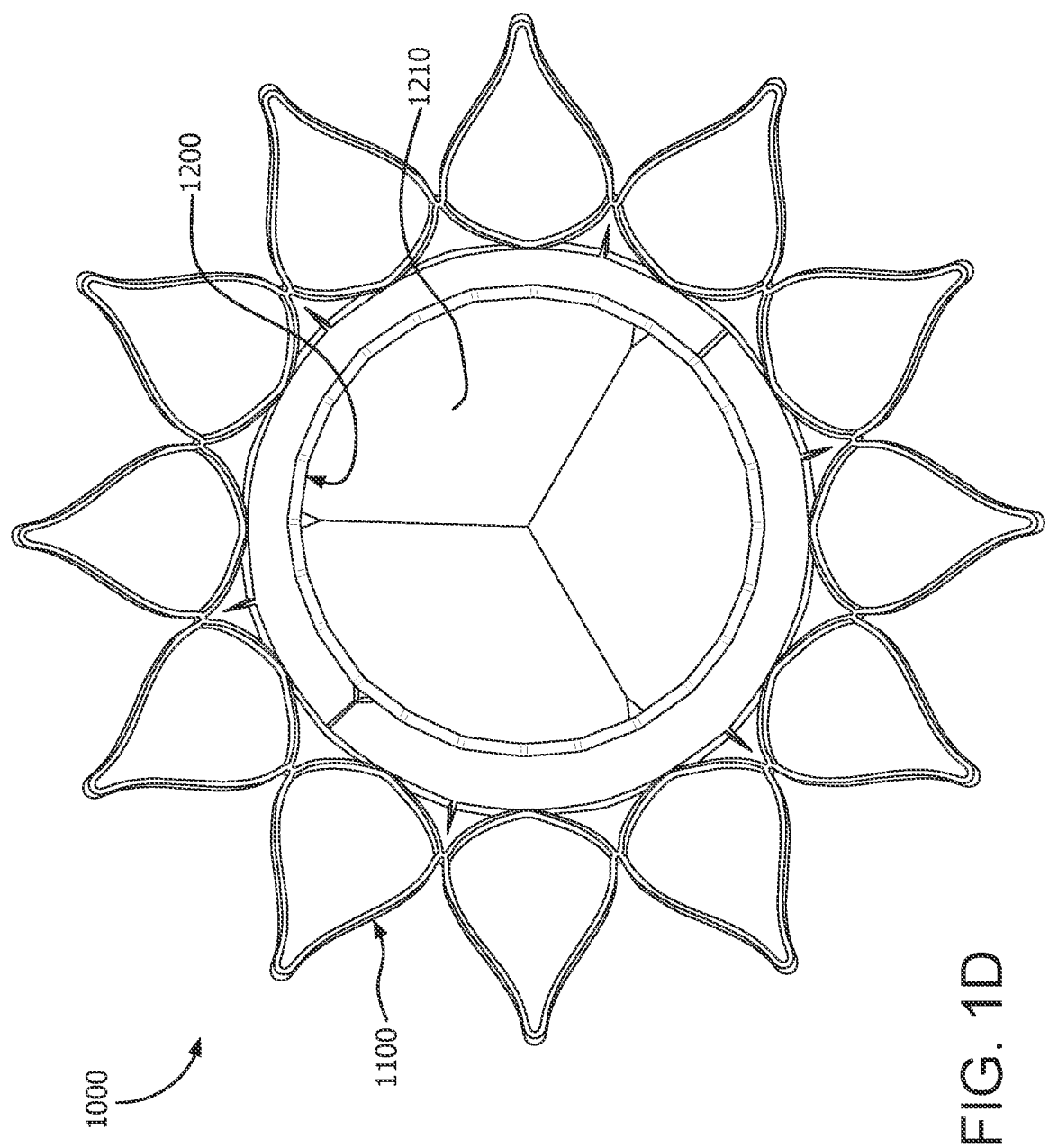
FIG. 1D is an axial view of the prosthetic valve of FIG. 1A, according to some embodiments.

FIG. 1C is a perspective view showing the valve frame subcomponent 1200 and an anchor frame subcomponent 1100 of a prosthetic valve 1000 in a nested configuration, also referred to as the deployed position, leaflets not shown for clarity. FIG. 1B is a front view of the valve frame subcomponent 1200 and the anchor frame subcomponent 1100 of the prosthetic valve 1000 of FIG. 1C. In both FIGS. 1B and 1C, the leaflets and any film, as will be discussed below, are not shown for clarity. FIG. 1D is an axial view of the valve frame subcomponent 1200 and the anchor frame subcomponent 1100 of the prosthetic valve 1000 of FIG. 1A, showing the leaflets 1210. In the axial view of FIG. 1D, three leaflets 1210 are shown coupled to the valve frame subcomponent 1200. It is in this deployed position that the prosthetic valve 1000 remains in the prosthetic valve orifice to function as a prosthetic valve. The anchor frame subcomponent 1100 and the valve frame subcomponent 1200 are longitudinally offset and generally coaxial relative to one another.

With continued reference to FIGS. 1A to 1D, a prosthetic valve 1000 includes an anchor frame 1102, and a valve frame 1202. In the deployed configuration, the valve frame subcomponent 1200, onto which leaflets 1020 are coupled, is positioned at least partially within the anchor frame subcomponent 1100. The prosthetic valve 1000 has a proximal end or proximal portion 1002 and a distal end or distal portion 1004. In various examples, when deployed within the body, the proximal portion 1002 of the prosthetic valve 1000 is positioned upstream or retrograde relative to the distal portion 1004 of the prosthetic valve 1000, which is positioned downstream or antegrade relative to the proximal portion 1002.

Figure 4:
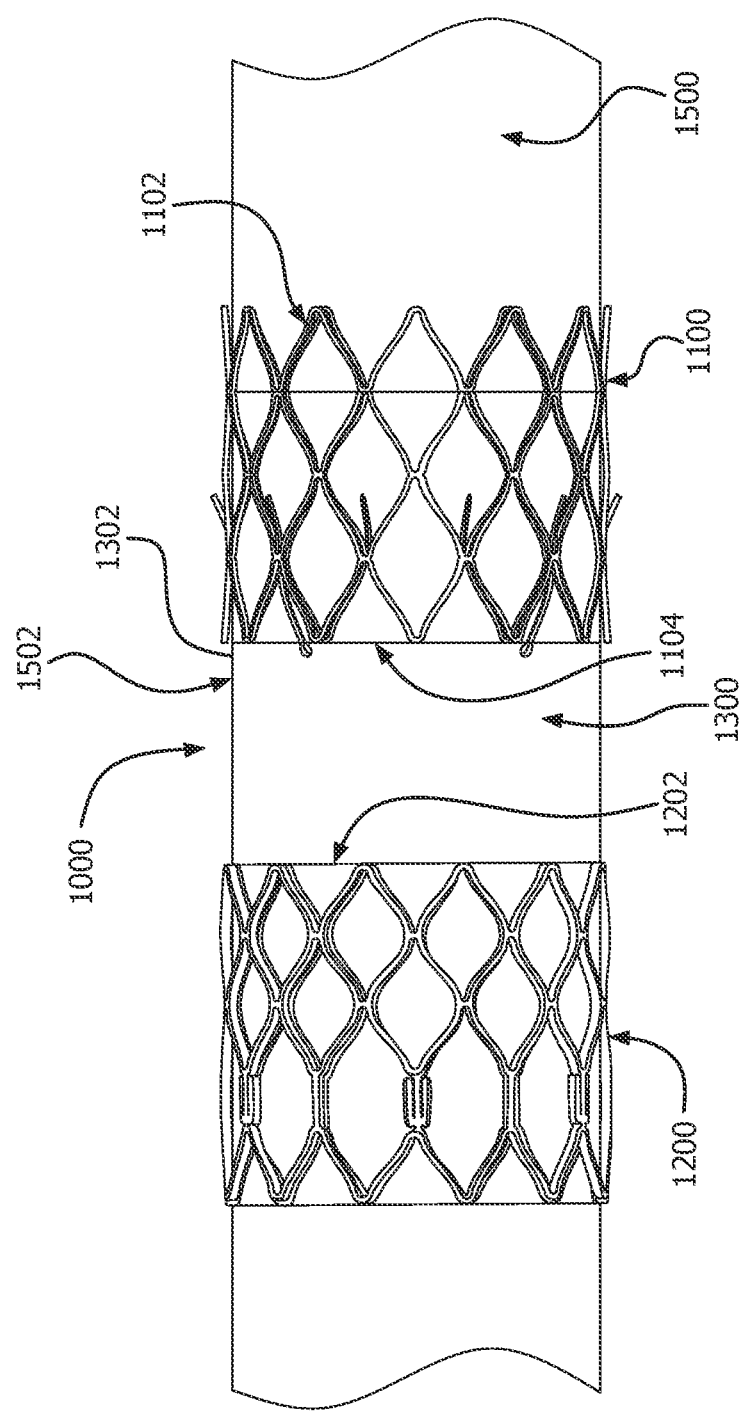
FIG. 4 is an illustration of a medical system, according to some embodiments.

In various embodiments, the anchor frame subcomponent 1100 and the valve frame subcomponent 1200 are coupled together. Referring to FIG. 4, showing a side view of the prosthetic valve in a pre-deployed configuration on a catheter, in some examples, a interstage 1300 is disposed within and/or about the anchor frame subcomponent 1100 and the valve frame subcomponent 1200. In some examples, the interstage 1300 is a contiguous film that at least extends between and operates to couple the anchor frame subcomponent 1100 and the valve frame subcomponent 1200 to one another. In some examples, the interstage 1300 extends not only between but also over or within either or both of the anchor frame subcomponent 1100 and the valve frame subcomponent 1200. The portion of the interstage 1300 that extends between and couples with the anchor frame subcomponent 1100 and the valve frame subcomponent 1200 is referred herein as the interstage portion 1302. In some examples, the interstage 1300 is formed from a generally tubular material and at least partially covers one or more of the anchor frame subcomponent 1100 and the valve frame subcomponent 1200. In some examples, the interstage 1300 is formed by wrapping a film over and around a cylindrical mandrel, with either or both of the anchor frame subcomponent 1100 and the valve frame subcomponent 1200 being slid over and bonded thereto to the inner surface of the frames. In some examples, the interstage 1300 is formed by wrapping the film over and around either or both of the anchor frame subcomponent 1100 and the valve frame subcomponent 1200 and bonded thereto to the outer surface of the frames.

In examples where the anchor frame subcomponent 1100 and the valve frame subcomponent 1200 are comprised of metal, there is a metal to polymer to metal interconnection, wherein there is no metal to metal contact between the two frames. Such configurations minimize the potential for metals of varying composition to react with one another or corrode.

The interstage 1300 is generally any sheet-like material that is biologically compatible and configured to couple to the anchor frame subcomponent 1100 and the valve frame subcomponent 1200. In various examples, the biocompatible material is a film that is not of a biological source and that is sufficiently flexible and strong for the particular purpose, such as a biocompatible polymer. In an embodiment, the film comprises a biocompatible polymer (e.g., ePTFE). In some examples, the film is a composite of two or more materials. The film may comprise one or more of a membrane, composite material, or laminate. In various examples, the construction of and materials used in the film are such that the interstage 1300 promotes cellular ingrowth, adhesion, and/or attachment. That is, in various examples, the interstage 1300 is constructed in a manner that promotes the ingrowth of tissue into one or more portions of the film. It will be appreciated that cellular ingrowth further increases sealing of the valve with the prosthetic valve orifice and helps minimize para-valvular leakage, that is, leakage between the prosthetic valve and the tissue into which it is coupled.

In various embodiments, the valve frame subcomponent 1200 additionally supports or otherwise includes a valve structure. In some examples, the valve structure includes one or more leaflets 1210 as shown in FIG. 1D. A variety of mechanical valve, biological leaflet, and synthetic leaflet designs are known in the medical technology arts, any of which may be incorporated into the valve frame subcomponent 1200 of the present disclosure. Examples of suitable leaflet constructions and methods of attachment to valve frame subcomponents are illustrated and described in U.S. patent application Ser. Nos. 13/833,650, 14/973,589, and 14/622,599, the contents of each of which are incorporated herein by reference. Further examples of suitable leaflet material are presented below.

In some examples, the valve or leaflets 1020 are coupled to the interior surface 1206 of the valve frame subcomponent 1200. In other examples, a film that comprises a leaflet is contained between the valve frame subcomponent 1200 and the anchor frame subcomponent 1100 and extends through a leaflet window defined by the valve frame subcomponent 1200. Such a configuration minimizes a potential for the leaflet to peel or delaminate, as compared to configurations where the leaflets are coupled to the interior surface 1206 of the valve frame subcomponent 1200. In some examples, one or more portions of the leaflets are wrapped about one or more portions of the valve frame subcomponent 1200. In some examples, the valve frame subcomponent 1200 includes one or more projections and the leaflets 1020 include one or more apertures that are configured to be disposed about the one or more projections.

In various embodiments, the valve frame subcomponent 1200 is nestable within the anchor frame subcomponent 1100. In particular, as shown, the anchor frame subcomponent 1100 and the valve frame subcomponent 1200 are sized and shaped in a manner that provides for the valve frame subcomponent 1200 being coaxially disposable or receivable at least partially within the anchor frame subcomponent 1100. Thus, in various examples, the anchor frame subcomponent 1100 is configured such that a portion of (or alternatively all of) the valve frame subcomponent 1200 can be received by or otherwise positioned within a space defined by the anchor frame subcomponent 1100. In some examples, the valve frame subcomponent 1200 is sized such that a diameter of the exterior surface of the valve frame subcomponent 1200 is less than a diameter of the interior surface of the anchor frame subcomponent 1100. In some examples, a diameter of the exterior surface of the valve frame subcomponent 1200 is in a range of between seventy five percent (75%) and ninety percent (90%) of a diameter of the interior surface of the anchor frame subcomponent 1100. In some examples, a diameter of the exterior surface of the valve frame subcomponent 1200 is seventy five percent (75%) or less than a diameter of the interior surface of the anchor frame subcomponent 1100. In various examples, such configurations also provide that the valve frame subcomponent 1200 can be received within the anchor frame subcomponent 1100. In various examples, such configurations provide that the anchor frame subcomponent 1100 can deform, such as, but not limited to being out of round or generally oval-shaped, to accommodate or otherwise conform to the prosthetic valve orifice without causing a deformation of the valve frame subcomponent 1200. The prosthetic valve 1000 provides a valve frame subcomponent 1200 that essentially floats within the anchor frame subcomponent 1100 and does not directly couple with a prosthetic valve orifice. The anchor frame subcomponent 1100 may conform to the shape of the prosthetic valve orifice whereas the valve frame subcomponent 1200 does not conform to the shape of the prosthetic valve orifice. The valve frame subcomponent 1200 remains cylindrical or at a preferred geometrical configuration so as to present the leaflets 1210 with a geometrically stable platform ensuring proper leaflet function, including coaptation and opening dynamics. It is appreciated that these benefits associated with the valve frame subcomponent 1200 not needing to conform to the prosthetic valve orifice may be realized in either transcatheter or surgical placement of the prosthetic valve 1000.

In various embodiments, as discussed in greater detail below, the prosthetic valve 1000 is configured such that the anchor frame subcomponent 1100 and the valve frame subcomponent 1200 can be nested in-situ after the anchor frame subcomponent 1100 and the valve frame subcomponent 1200 are deployed at a treatment site in a patient's anatomy. That is, in various embodiments, the prosthetic valve 1000 can be delivered to a treatment region within a patient's anatomy with the anchor frame subcomponent 1100 and the valve frame subcomponent 1200 longitudinally offset relative to one another and subsequently nested with one another at the treatment site. In various embodiments, the prosthetic valve 1000 is loaded onto a delivery catheter with the anchor frame subcomponent 1100 and the valve frame subcomponent 1200 longitudinally offset relative to one another which presents a lower profile or diameter than if the prosthetic valve 1000 were to be loaded onto the delivery catheter in the nested configuration. A lower delivery profile of a transcatheter delivered prosthetic valve has well recognized advantages, including easier advancement though vessels.

It is appreciated that these benefits associated with the valve frame subcomponent 1200 not being nested into the anchor frame subcomponent 1100 during implantation may also be realized in surgical placement of the prosthetic valve 1000. By way of example, but not limited thereto, the anchor frame subcomponent 1100 may be more easily sutured into the prosthetic valve orifice without the valve frame subcomponent 1200 being within the anchor frame subcomponent 1100 and in close proximity to the suturing procedure lessening the chance of needle damage to the leaflets.

In some embodiments, the anchor frame subcomponent 1100 and the valve frame subcomponent 1200 are operable to nest with one another by telescoping the anchor frame subcomponent 1100 and the valve frame subcomponent 1200 relative to one another in-situ. Thus, in various examples, the valve frame subcomponent 1200 and the anchor frame subcomponent 1100 are sized such that the valve frame subcomponent 1200 can be receive within the interior region 1110 of the anchor frame subcomponent 1100.

In various embodiments, in addition to or alternative to telescoping relative to one another, the anchor frame subcomponent 1100, the valve frame subcomponent 1200, and the film 1300 are each configured to be compressed or collapsed to a delivery profile and then reexpanded in-situ to provide for transcatheter delivery of the prosthetic valve 1000, as discussed in greater detail below.

FIGS. 2A and 2B are side and axial views, respectively, of the anchor frame subcomponent 1100, in accordance with an embodiment. The anchor frame subcomponent 1100 is a generally tubular member having a proximal end 1102, a distal end 1104, an interior surface 1106, and an exterior surface 1108. In various examples, the anchor frame subcomponent 1100 defines an interior region 1110. For example, the interior region 1110 is a generally cylindrical void defined between the proximal and distal ends 1102 and 1104, and the interior surface 1106 of the anchor frame subcomponent 1100. However, in-situ, the interior region 1110 may adopt an irregular cross section, depending on the geometry of the prosthetic valve orifice. In various examples, the anchor frame subcomponent 1100 is configured to couple to a native valve orifice. Accordingly, in various examples, a diameter of the anchor frame subcomponent 1100 (e.g., a diameter of an interior or exterior surface of the anchor frame subcomponent 1100) is sized in accordance with patient anatomy. It will be appreciated that nonlimiting examples of anchor frame subcomponents 1100 can be provided with a diameter (e.g., a diameter of an interior or exterior surface of the anchor frame subcomponent 1100) in a range of between twenty five (25) millimeters and fifty (50) millimeters, depending on a patient's anatomy. However, anchor frame subcomponents 1100 having diameters (e.g., a diameter of an interior or exterior surface of the anchor frame subcomponent 1100) in excess of fifty (50) millimeters are also envisioned and fall within the scope of the present disclosure, depending on patient anatomy.

In some embodiments, the anchor frame subcomponent 1100 defines a cylindrical or tubular mesh having a framework defining apertures. For example, as shown, the anchor frame subcomponent 1100 includes a plurality of frame members 1112 that are interconnected and arranged in one or more patterns. In some examples, these patterns repeat one or more times. In some such examples, the frame members 1112 are arranged and interconnected such that the anchor frame subcomponent 1100 includes a plurality of patterned rows. In various examples, the frame members 1112 are connected to one another at various joints 1114. In some examples, these joints 1114 operate as flex points so as to provide a preferential flexing location for the anchor frame subcomponent 1100 to flex when compressed to a smaller delivery diameter and when forces from the surrounding anatomy act to compress the anchor frame subcomponent 1100 during normal operation after delivery and deployment of the prosthetic valve 1000. In some examples, a flex point or joint 1114 comprises a site on the anchor frame subcomponent 1100 that undergoes a high degree of bending. In some examples, the joints 1114 may comprise a geometry, structural modification or material modification, among others, that biases the anchor frame subcomponent 1100 to bend at the flex point or joint 1114 when compressed.

In some embodiments, one or more closed cell apertures or voids 1116 are defined between the joints 1114 and the interconnected frame members 1112 of the anchor frame subcomponent 1100. In some examples, these apertures or voids 1116 extend from the exterior surface 1108 to the interior surface 1106 of the anchor frame subcomponent 1100. As illustrated in the embodiments of FIGS. 2A and 2B, one or more of the apertures or voids 1116 define a diamond shape when the anchor frame subcomponent 1100 is in a deployed configuration. Upon compression to a smaller diameter (e.g., a delivery diameter), one or more of the joints 1114 and the frame members 1112 deform such that the apertures or voids 1116 generally define an elongated diamond shape (e.g., as shown generally in FIG. 4A). Upon re-expanding the anchor frame subcomponent 1100 to a larger diameter during deployment at a treatment site, the apertures or voids 1116 re-expand to define the generally wider diamond shape.

In some embodiments, the anchor frame subcomponent 1100 defines a flange or a flared portion at its proximal end 1102 that flares or tapers radially outward when in the deployed configuration. For example, as shown in at least FIGS. 1B, 2A, and 5B-5E, the proximal end 1102 is flared or otherwise tapered radially outward when in the deployed configuration. That is, as shown, the proximal end 1102 of the anchor frame subcomponent 1100 has a larger deployed diameter than does the distal end 1104 of the anchor frame subcomponent 1100. In various examples, as discussed in greater detail below, such a configuration operates to minimize migration risks and helps facilitate abutment of the anchor frame subcomponent 1100 with native tissue at the treatment site.

It should be appreciated that while the frame members 1112 illustrated and described herein are interconnected and define apertures or voids 1116 having generally a diamond shape, the interconnected frame members 1112 may be arranged in a number of alternative patterns. For example, a framework of the anchor frame subcomponent 1100 can define any number of features, repeatable or otherwise, such as geometric shapes and/or linear or meandering series of sinusoids. Geometric shapes can comprise any shape that facilitates circumferential compressibility and expandability of the anchor frame subcomponent 1100. That is, a number of alternative patterns are envisioned where the arrangement of frame members 1112 is configured in such a manner as to provide for an anchor frame subcomponent 1100 that can be compressed to a smaller diameter for transcatheter delivery and subsequently expanded (or allowed to expand) to a larger diameter at a treatment site during deployment of the prosthetic valve 1000. Accordingly, the disclosure should not be read as being limited to arrangements of the frame members 1112 that define diamond-shaped apertures or voids 1116.

In various embodiments, the anchor frame subcomponent 1100 may comprise or otherwise be formed from a cut tube, or any other element suitable for the particular purpose of the anchor frame subcomponent 1100 as described herein. In some examples, the anchor frame subcomponent 1100 may be etched, cut, laser cut, or stamped into a tube or a sheet of material, with the sheet then formed into a substantially cylindrical structure. Alternatively, an elongated material, such as a wire, bendable strip, or a series thereof, can be bent or braided and formed into a substantially cylindrical structure wherein the walls of the cylinder comprise an open framework that is compressible to a smaller diameter in a generally uniform and circumferential manner and expandable to a larger diameter as illustrated and described herein.

The anchor frame subcomponent 1100 can comprise any metallic or polymeric biocompatible material. For example, the anchor frame subcomponent 1100 can comprise a material, such as, but not limited to nitinol, cobalt-nickel alloy, stainless steel, or polypropylene, acetyl homopolymer, acetyl copolymer, ePTFE, other alloys or polymers, or any other biocompatible material having adequate physical and mechanical properties to function as described herein.

In various examples, the anchor frame subcomponent 1100 is elastically deformable so as to be self-expanding under spring loads, as those of skill will appreciate. In some examples, the anchor frame subcomponent 1100 is plastically deformable so as to be mechanically expanded such as with a balloon, as those of skill will appreciate. In yet some other examples, the anchor frame subcomponent 1100 is plastically deformable as well as elastically deformable. That is, in some examples, the anchor frame subcomponent 1100 includes one or more elastically deformable components or features and one or more plastically deformable components or features. Thus, it should be appreciated that the examples of the anchor frame subcomponent 1100 presented herein are not to be limited to a specific design or mode of expansion.

In various embodiments, the anchor frame subcomponent 1100 is configured to provide positive engagement with an implant site to firmly anchor the prosthetic valve 1000 to the site. For instance, in various examples, the anchor frame subcomponent 1100 includes one or more tissue engagement features 1118 that are configured to engage one or more regions of tissue at the prosthetic valve orifice surrounding the prosthetic valve 1000. In various examples, the tissue engagement features 1118 comprise one or more barbs or tissue anchors.

In various examples, the one or more tissue engagement features 1118 project away from the interior and/or exterior surfaces 1106 and 1108 of the anchor frame subcomponent 1100, radially outward from a longitudinal axis of the anchor frame subcomponent 1100, and toward the tissue surrounding the prosthetic valve 1000. Generally, the tissue engagement features 1118 are operable to project away from the anchor frame subcomponent 1100 when the anchor frame subcomponent 1100 is deployed (e.g., when a constraining member is withdrawn or otherwise removed). In some examples, with the anchor frame subcomponent 1100 in the deployed configuration, the tissue engagement features 1118 are operable to engage the tissue proximate the anchor frame subcomponent 1100 such that the tissue engagement features 1118 secure the anchor frame subcomponent 1100 to the surrounding tissue, as will be discussed in greater detail below.

In some examples, in a deployed configuration, the tissue engagement features project away from an exterior surface of the anchor frame subcomponent in a range of between thirty (30) and sixty (60) degrees. In some such examples, the tissue engagement features project away from an exterior surface of the anchor frame subcomponent at an angle of approximately forty five (45) degrees, though other configurations are contemplated and fall within the scope of the present application. Generally, any angle of projection is suitable provided that the tissue engagement features operate for their intended purpose of engaging the tissue surrounding the anchor frame subcomponent and causing the anchor frame subcomponent to be secured to the surrounding tissue. Though the tissue engagement features may include a variety of different lengths (depending on the angle from which they project from the anchor frame subcomponent), it will be appreciated that the tissue engagement features are of a length suitable for engaging tissue and securing the anchor frame subcomponent to the surrounding tissue, but not so long as to risk detrimental damage to the prosthetic valve orifice. One nonlimiting example configuration includes tissue engagement features projecting from the anchor frame subcomponent in a range of between thirty (30) and sixty (60) degrees and having a length of between fifty (50) micron and two hundred (200) micron.

Generally, the tissue engagement features 1118 are positioned along the anchor frame subcomponent such that they are operable to engage tissue proximate the anchor frame subcomponent 1100 when the anchor frame subcomponent 1100 is expanded in-situ. The tissue engagement features 1118 may be arranged in one or more rows along a longitudinal axis of the anchor frame subcomponent 1100. That is, in various examples, anchor frame subcomponent may include a first set (or row) of anchors and a second set (or row) of anchors longitudinally offset relative to the first set of anchors. In one such example, the first set of anchors is more proximate the distal end 1104 of the anchor frame subcomponent 1100 than is the second set of anchors.

In various embodiments, the one or more tissue engagement features 1118 are circumferentially arranged about the anchor frame subcomponent 1100. In some examples, the one or more tissue engagement features 1118 are evenly dispersed about the circumference of the anchor frame subcomponent. For example, the tissue engagement features 1118 are dispersed about the frame and are offset from one another by ninety (90) degrees depending on the number of anchors. Alternatively, the tissue engagement features 1118 may be dispersed about the frame and offset from one another by sixty (60) degrees depending on the number of anchors. Generally, the angular offset between the anchors is a function of the number of anchors dispersed about the anchor frame subcomponent 1100, as those of skill will appreciate. In some examples, the angular offset between the anchors is additionally or alternatively based on an arrangement or pattern of the frame members 1112.

In various examples, while the tissue engagement features 1118 project away from the anchor frame subcomponent 1100 when the anchor frame subcomponent 1100 is in the deployed configuration, the tissue engagement features 1118 are stowed or do not otherwise project away from the anchor frame subcomponent 1100 when the anchor frame subcomponent 1100 is compressed in the delivery configuration. Thus, in various examples, the tissue engagement features 1118 are stowable during delivery and are configured to transition to a deployed configuration where they project away from the anchor frame subcomponent 1100. In some examples, a constraining member disposed about the anchor frame subcomponent 1100 during delivery facilitates stowing of the tissue engagement features 1118. In some examples, the tissue engagement features 1118 are stowed in associated apertures or voids 1116 of the anchor frame subcomponent 1100.

In various embodiments, the tissue engagement features 1118 are integral to the anchor frame subcomponent 1100. For example, one or more of the tissue engagement features 1118 are formed in conjunction with and from the same material as the frame members 1112. In other examples, one or more of the tissue engagement features 1118 are separate components additionally or alternatively coupled or attached to the anchor frame subcomponent 1100. For instance, some non-limiting examples include crimping and/or welding one or more tissue engagement features to the anchor frame subcomponent 1100.

Likewise, while the proximal end 1102 of the anchor frame subcomponent 1100 tapers or flares radially outward in a deployed configuration in certain examples, the flared or tapered portion of the anchor frame subcomponent 1100 is configured to deflect when the anchor frame subcomponent 1100 is in the delivery configuration. For example, as shown in FIG. 4A, the flared or tapered proximal end 1102 of the anchor frame subcomponent 1100 is deflected such that the anchor frame subcomponent 1100 has a substantially uniform delivery profile along its longitudinal axis. In various examples, one or more constraining members (not shown) are disposed about the anchor frame subcomponent 1100 in the delivery configuration. For example, a first constraining member is disposed about the proximal end 1102 of the anchor frame subcomponent 1100 and a second constraining member is disposed about the distal end 1104 of the anchor frame subcomponent 1100, as will be described in more detail when referring to FIGS. 9-16. Each constraining member may extend about an exterior surface 1108 of the anchor frame subcomponent 1100, or one or more of the constraining members may be woven through one or more portions of the film disposed about the anchor frame subcomponent 1100. That is, in some examples, one or more of the constraining members extending about the exterior surface 1108 may extend through a portion of the film, and extend along a portion of the interior surface 1106 of the anchor frame subcomponent 1100, and then extend back through the film to the exterior surface 1108 and extend therearound. In some examples, the one or more constraining members individually or collectively operate to constrain the anchor frame subcomponent 1100 in a delivery configuration. In various examples, this includes one or more constraining members individually or collectively constrains the flange or flared portion of the anchor frame subcomponent 1100 in a delivery configuration. Additionally or alternatively, in some examples, a removable constraining sheath is disposed about the flange or flared portion of the anchor frame subcomponent 1100 in a delivery configuration. In some examples, the delivery system may include one or more flange stops (see e.g., flange stop 1562 in FIG. 16). In some examples, the flange stops operate to constrain the anchor frame subcomponent 1100 from translating proximally as a constraining sheath (see, e.g., constraining sheath 1564 in FIG. 16) is withdrawn from one or more of the anchor frame subcomponent 1100 and the valve frame subcomponent 1200. In some examples, one or more constraining members individually or collectively constrain the tissue engagement features to a delivery (undeployed) configuration. Additionally or alternatively, in some examples, a removable constraining sheath is disposed about the tissue engagement features of the anchor frame subcomponent 1100. In some examples, the one or more constraining members are removed from the anchor frame subcomponent 1100 during deployment of the anchor frame subcomponent 1100. In some examples, the constraining members includes a fiber. In some examples, the constraining members includes a wire. In some examples, one or more lockwires engage a first end of the one or more constraining members at or proximate the anchor frame subcomponent 1100 such that tension can be applied to an opposing second end of the one or more constraining members. In various examples, tensioning the one or more constraining members operates to maintain the anchor frame subcomponent 1100 in the delivery configuration.

In various examples, one or more constraining members are disposed about the valve frame subcomponent 1200 in the delivery configuration, as will be described in more detail when referring to FIGS. 9-16. For example, a third constraining member is disposed about the proximal end 1202 of the valve frame subcomponent 1200 and a fourth constraining member is disposed about the distal end 1204 of the valve frame subcomponent 1200. Each constraining member may extend about an exterior surface 1208 of the valve frame subcomponent 1200. In some such examples, one or more of the constraining members may be woven through one or more portions of the film disposed about the valve frame subcomponent 1200. That is, in some examples, one or more of the constraining members extending about the exterior surface 1208 may extend through a portion of the film, and extend along a portion of the interior 1206 of the valve frame subcomponent 1200, and then extend back through the film to the exterior surface 1206 and extend therearound. In some examples, the one or more constraining members individually or collectively operate to constrain the valve frame subcomponent 1200 in a delivery configuration. In various examples, one or more constraining members individually or collectively constrain the tissue retention features to a delivery (undeployed) configuration. Additionally or alternatively, in some examples, a removable constraining sheath is disposed about the tissue engagement features of the valve frame subcomponent 1200. It will be appreciated that the removable constraining sheath may be disposed about both the valve frame subcomponent 1200 and the anchor frame subcomponent 1100 (see discussion above). In some examples, the one or more constraining members are removed from the valve frame subcomponent 1200 during deployment of the valve frame subcomponent 1200. In some examples, the constraining members includes a fiber. In some examples, the constraining members includes a wire. In some examples, one or more lockwires engage a first end of the one or more constraining members at or proximate the valve frame subcomponent 1200 such that tension can be applied to an opposing second end of the one or more constraining members. In various examples, tensioning the one or more constraining members operates to maintain the valve frame subcomponent 1200 in the delivery configuration.

In various embodiments, in addition to facilitating a positive engagement with an implant site to anchor the prosthetic valve 1000 to the surrounding tissue, the anchor frame subcomponent 1100 additionally or alternatively includes one or more mechanisms that facilitate a positive engagement with the valve frame subcomponent 1200 upon nesting the anchor frame subcomponent 1100 and the valve frame subcomponent 1200. Specifically, in various examples, the anchor frame subcomponent 1100 includes one or more interlock features 1120 that project into the interior region 1110 of the anchor frame subcomponent 1100. These interlock features 1120 are configured to engage the nested valve frame subcomponent 1200 and maintain a relative axial position (or at least minimize relative axial movement) between the anchor frame subcomponent 1100 and the valve frame subcomponent 1200.

In various examples, the interlock features 1120 are structures that project or otherwise extend away from the interior and exterior surfaces 1106 and 1108 of the anchor frame subcomponent 1100 and toward the interior region 1110 defined by the anchor frame subcomponent 1100. In some examples, the one or more interlock features 1120 are in the form of one or more tabs.

In some examples, the one or more interlock features 1120 have a free end 1122 and a base 1124. In some examples, the free end 1122 is an end that is not otherwise coupled to or mated with the anchor frame subcomponent 1100. The base 1124 is generally the portion of the interlock feature that couples to or is otherwise integral with the anchor frame subcomponent 1100. Generally, the free end 1122 is operable to move relative to the anchor frame subcomponent 1100, while the base 1124 is coupled to the anchor frame subcomponent 1100.

Though a variety of geometries are envisioned, the nonlimiting exemplary interlock features 1120 illustrated in FIGS. 2A and 2B are each elongate elements. In addition, the free end 1122 is illustrated as being a generally blunt or round end, though the free end 1122 or the interlock feature 1120, generally, may alternatively be pointed or possess other suitable geometry such as a curved shape (e.g., an s-shape). In other words, other geometries suitable for engaging the valve frame subcomponent 1200 when it is nested with the anchor frame subcomponent 1100 in the manner illustrated and described herein are envisioned and may be utilized without departing from the spirit or scope of the disclosure. In some examples, the free end 1122 of the interlock feature 1120 is shaped such that it is operable to slide along the exterior of the valve frame subcomponent 1200. As mentioned above, in some examples, a film (e.g., film 1300) covers one or more portions of the valve frame subcomponent 1200. Thus, in some examples, the free end 1122 of the interlock feature 1120 is shaped and sized in a manner that allows the interlock feature 1120 to slide along the exterior of the valve frame subcomponent 1200 without binding. In one nonlimiting example, the interlock feature 1120 is approximately six hundred micron in length and is angled at approximately forty five (45) degrees relative to the interior of the anchor frame subcomponent. It will be appreciated, however, that a number of angle and length configurations are contemplated and fall within the scope of the present application.

Similar to the tissue engagement features 1118, the interlock features 1120 may be arranged in one or more rows along a longitudinal axis of the anchor frame subcomponent 1100. That is, in various examples, anchor frame subcomponent 1100 may include a first set (e.g., a row) of interlock features and a second set (e.g., a row) of interlock features longitudinally offset relative to the first set of interlock features. In one such example, the first set of interlock features is more proximate the distal end 1104 of the anchor frame subcomponent 1100 than is the second set of interlock features. In various examples, while the interlock features 1120 are configured to project away from the anchor frame subcomponent 1100 when the anchor frame subcomponent 1100 is in the deployed configuration, the interlock features 1120 are stowed or do not otherwise project away from the anchor frame subcomponent 1100 when the anchor frame subcomponent 1100 is compressed in the delivery configuration. Thus, in various examples, the interlock features 1120 are configured to transition between a stowed or delivery configuration and a projecting or deployed configuration. Thus, in various examples, the interlock features 1120 are resilient members that are configured to deflect under certain conditions.

In various examples, as mentioned above, the interlock features 1120 are configured to engage the valve frame subcomponent 1200 as it is nested with the anchor frame subcomponent 1100 in-situ. In some examples, as discussed further below, the interlock features 1120 temporarily deflect from an engaged position to enable nesting of the valve frame subcomponent 1200 with the anchor frame subcomponent 1100, and subsequently return to the engaged position after the valve frame subcomponent 1200 is nested with the anchor frame subcomponent 1100. In various examples, the interlock features 1120 return to the engaged position upon the valve frame subcomponent 1200 being proximally advanced a suitable amount relative to the anchor frame subcomponent 1100. Put differently, in some examples, the interlock features 1120 of the anchor frame subcomponent 1100 are operable to adopt an engaged position where they engage the valve frame subcomponent 1200 and minimize relative axial translation between the valve frame subcomponent 1200 and the anchor frame subcomponent 1100 upon proximally advancing the valve frame subcomponent 1200 a designated amount relative to the anchor frame subcomponent 1100.

In some examples, a delivery catheter upon which the anchor frame subcomponent 1100 is loaded during delivery causes stowing of the interlock features 1120.

In various examples, the interlock features 1120 are integral to the anchor frame subcomponent 1100. For example, one or more of the interlock features 1120 are formed in conjunction with and from the same material as the frame members 1112. In other examples, one or more of the interlock features 1120 are additionally or alternatively coupled to the anchor frame subcomponent 1100. That is, in some examples, one or more interlock features 1120 are additionally or alternatively attached to the anchor frame subcomponent 1100. In various examples, the one or more interlock features 1120 are circumferentially arranged about the anchor frame subcomponent 1100. In some examples, the one or more interlock features 1120 are evenly dispersed about the circumference of the anchor frame subcomponent. In a manner similar to that discussed above with respect to the tissue engagement features 1118, the angular offset between the anchors is generally a function of one or more of the arrangement of the frame members 1112 and the number of anchors dispersed about the anchor frame subcomponent 1100, as those of skill will appreciate.

It should be appreciated that while the interlock features are illustrated and described herein as extending from the anchor frame subcomponent 1100, in various examples, one or more interlock features additionally or alternatively extend from the valve frame subcomponent 1200. For instance, in some examples, the valve frame subcomponent includes one or more interlock features (not shown) that extend from the exterior surface 1208 away from the interior surface 1206 of the valve frame subcomponent 1200 and that are operable to engage the anchor frame subcomponent 1100 upon nesting of the anchor frame subcomponent 1100 and the valve frame subcomponent 1200. In various examples, the interlock features of the valve frame subcomponent 1200 are positionable at a proximal end 1202, a distal end 1204, or some position between the proximal and distal ends 1202 and 1204 provided that the interlock features of the valve frame subcomponent are operable to engage the anchor frame subcomponent 1100 upon nesting of the anchor frame subcomponent 1100 and the valve frame subcomponent 1200. In various examples, the interlock features of the valve frame subcomponent are deflectable and stowable in a manner similar to the interlock features 1120 of the anchor frame subcomponent 1100, as previously described.

FIGS. 3A and 3B are side and axial views, respectively, of the valve frame subcomponent 1200, in accordance with an embodiment. The valve frame subcomponent 1200 is generally cylindrical or tubular member having a proximal end 1202, a distal end 1204, an interior surface 1206, and an exterior surface 1208. In various examples, the valve frame subcomponent 1200 defines an interior region 9999. For example, interior region is a generally cylindrical void defined between the proximal and distal ends 1202 and 1204, and the interior surface 1206 of the valve frame subcomponent 1200. Generally, the valve frame subcomponent 1200 is configured to be received within at least a portion of the anchor frame subcomponent 1100, as mentioned above. It will be appreciated that nonlimiting examples of valve frame subcomponents 1200 can be provided with a diameter (e.g., a diameter of an interior or exterior surface of the valve frame subcomponent 1200) in a range of between twenty (20) millimeters and thirty (30) millimeters, depending on a patient's anatomy.

Tissue Retention Features

In various examples, the valve frame subcomponent 1200 includes one or more features that operate to grab or otherwise interface with native valve tissue (e.g., native leaflet tissue) or tissue surrounding the native valve being replaced. Specifically, in various examples, and with continued reference to FIGS. 3A and 3B, the valve frame subcomponent 1200 includes one or more tissue retention features 1218 (also referred to herein as tissue graspers). The one or more tissue retention features 1218 are projections of the valve frame subcomponent 1200 that are configured to interface with the patient's native tissue associated with the native valve. In some examples, the one or more tissue retention features 1218 are configured to engage the native tissue and cause it to be secured between the anchor frame subcomponent 1100 and the valve frame subcomponent 1200 as the anchor frame subcomponent 1100 and the valve frame subcomponent are nested together in-situ, as discussed in greater detail below. Such a configuration provides that the native tissue does not interfere with or otherwise obstruct the flow of fluid (e.g., blood) downstream or antegrade to the prosthetic valve 1000 after the prosthetic valve 1000 has been deployed. In mitral valve repair/augmentation procedures for example, the capture and securement of at least the native anterior leaflet of the native mitral valve minimized that potential for the native anterior leaflet to deflect into the left ventricle and create a left ventricle outflow tract obstruction. Thus, in various embodiments, the one or more tissue retention features 1218 are configured to interface with one or more of the native leaflets associated with the native valve. Though mitral valve repair/augmentation procedures are discussed herein, it will be appreciated that the scope of the disclosure applies to repair/augmentation of the atrioventricular (AV) valves and the semilunar (SL) valves. The disclosure should therefore not be interpreted as being limited to mitral valve repair/augmentation.

In various examples, the tissue retention features 1218 are structures that project or otherwise extend away from the interior and exterior surfaces 1206 and 1208 of the valve frame subcomponent 1200 and toward the tissue surrounding the prosthetic valve 1000 (e.g., the native valve orifice). In some examples, the one or more tissue retention features 1218 are in the form of one or more tabs. In some examples, the one or more tissue retention features 1218 are looped features having an apex and two ends, wherein the two ends are coupled to, integral with, extend from, or otherwise terminate into one or more portions of the valve frame subcomponent 1200. In some such examples, the apex is a free end that is operable to deflect and project away from the valve frame subcomponent 1200, as mentioned below.

In some examples, the one or more tissue retention features 1218 have a free end 1220 and a base 1222. In some examples, the free end 1220 is an end that is not otherwise coupled to or mated with the valve frame subcomponent 1200. The base 1222 includes one or more portions of the tissue retention feature 1218 that couple to or are otherwise integral with the valve frame subcomponent 1200. Generally, the free end 1220 is operable to move relative to the valve frame subcomponent 1200, while the base 1222 is coupled to the valve frame subcomponent 1200.

Though a variety of geometries are envisioned, the nonlimiting exemplary tissue retention features 1218 illustrated in FIGS. 3A and 3B are each generally triangularly shaped and include a free end 1220 and a base 1222. The base 1222 includes a plurality of ends 1224 and 1226 that are each coupled to, integral with, extend from, or otherwise terminate into the valve frame subcomponent 1200. As shown, the plurality of ends 1224 and 1226 converge to form the free end 1220. In addition, while the free end 1220 is illustrated as being a generally blunt or round end, the free end 1220 may alternatively be pointed or possess other suitable geometry. In other words, other geometries suitable for engaging surrounding tissue in the manner illustrated and described herein are envisioned and may be utilized without departing from the spirit or scope of the disclosure. For instance, another non-limiting exemplary tissue retention feature includes an end coupled to or otherwise integral with the valve frame subcomponent 1200 and a plurality of free ends extending from the end coupled to the valve frame subcomponent 1200. Another non-limiting exemplary tissue retention feature includes a barb or similar feature having opposed single ends coupled to or otherwise integral with the valve frame subcomponent 1200. As discussed in greater detail below, the profile of the free end 1220 of the tissue retention feature 1218 is one generally well suited for penetrating tissue or penetrating between tissue of the surrounding anatomy.

In various examples, the tissue retention features 1218 have a first side 1228 and a second side 1230. As shown in FIGS. 3A and 3B, the first side 1228 faces the exterior surface 1208 of the valve frame subcomponent 1200, and the second side 1230 faces away from the exterior surface 1208 of the valve frame subcomponent. In some examples, a void or open space region is defined between the first side 1228 and the exterior surface 1208 of the valve frame subcomponent 1200. In various examples, as discussed below, this open space region between the first side 1228 and the exterior surface 1208 of the valve frame subcomponent 1200 is configured to accommodate a portion of native tissue (e.g., valve leaflets) from anatomy surrounding the prosthetic valve 1000.

Generally, the one or more tissue retention features 1218 of the valve frame subcomponent 1200 are situated along the valve frame subcomponent 1200 proximate a distal end 1204 thereof. In some examples, the base 1222 of the one or more tissue retention features 1218 forms part of the distal end of the valve frame subcomponent 1200. In other examples, the base 1222 of the one or more tissue retention features 1218 is situated proximal to the distal end 1204 of the valve frame subcomponent 1200. Thus, the one or more tissue retention features 1218 can be generally located at any position along the longitudinal axis of the valve frame subcomponent 1200 provided that the tissue retention features 1218 are appropriately sized and shaped for causing native tissue to be captured between the anchor frame subcomponent 1100 and the valve frame subcomponent 1200 upon nesting of the anchor frame subcomponent 1100 and the valve frame subcomponent 1200.

In various examples, the one or more tissue retention features 1218 are circumferentially arranged about the valve frame subcomponent 1200. In some examples, the one or more tissue retention features 1218 are evenly dispersed about the circumference of the anchor frame subcomponent. For example, the tissue retention features 1218 are dispersed about the frame and are offset from one another by ninety (90) degrees depending on the number of tissue retention features. Alternatively, the tissue retention features 1218 may be dispersed about the frame and offset from one another by sixty (60) degrees, or some other angular offset, depending on the number of tissue retention features. Generally, the angular offset between the anchors is a function of the number of tissue retention features dispersed about the valve frame subcomponent 1200, as those of skill will appreciate. In some examples, the angular offset between the tissue retention features is additionally or alternatively based on an arrangement or pattern of the frame members 1212. Such configurations provide for a prosthetic valve that is deployable in virtually any angular orientation about the longitudinal axis of the prosthetic valve 1000. That is, such configurations minimize the need for physicians to orient the prosthetic valve 1000 about a longitudinal axis of the prosthetic valve 1000 relative to the surrounding native tissue.

In some examples, the tissue retention features are dispersed about the valve frame subcomponent based on the anatomy of the native tissue surrounding the natural valve to be replaced by the prosthetic valve. For example, the mitral valve is comprised of two native leaflets. In exemplary embodiments including a prosthetic valve configured for implantation to repair or augment a damaged or faulty native mitral valve, the tissue retention features of the valve frame subcomponent may be more heavily distributed within certain angular regions to increase the number of tissue retention features in proximity to the native leaflets to capture the native leaflets.

In various examples, as mentioned above, the one or more tissue retention features 1218 project away from the valve frame subcomponent 1200 toward the surrounding tissue when the valve frame subcomponent 1200 is in the deployed configuration. In some examples, the one or more tissue retention features 1218 project away from the valve frame subcomponent 1200 such that the free end 1220 of the tissue retention feature 1218 is more radially offset from an axis of the valve frame subcomponent 1200 (e.g., extends more radially outwardly) than is the base 1222 of the tissue retention feature 1218. In other words, in various examples, one or more of the tissue retention feature 1218 are angled relative to a longitudinal axis of the valve frame subcomponent 1200 and/or the exterior surface 1208 of the valve frame subcomponent 1200 when the valve frame subcomponent 1200 is in the deployed configuration. Such a configuration provides that the open space region defined between the first side 1228 and the exterior surface 1208 of the valve frame subcomponent 1200 is tapered. In some examples, the open space region is wedge-shaped.

In various examples, a length and angle configuration of the tissue retention features 1218 is based on the relative sizes of the anchor frame subcomponent 1100 and the valve frame subcomponent 1200. For example, the length and angle configuration of the tissue retention features 1218 is such that the tissue retention features 1218 do not prevent or otherwise obstruct the valve frame subcomponent 1200 from telescoping or otherwise being nested with the anchor frame subcomponent 1100. Additionally, however, the length and angle configuration of the tissue retention features 1218 is one that provides for the tissue engagement features engaging one or more of the native leaflets of the patient's anatomy, as discussed herein. In some nonlimiting examples, the tissue retention features 1218 have a length of between six hundred (600) and one thousand (1000) micron and that project away from the valve frame subcomponent 1200 at an angle in a range of between thirty (30) and sixty (60) degrees. Accordingly, though a variety of other configurations are contemplated, one nonlimiting example configuration includes tissue engagement features having a length of approximately eight hundred (800) micron and that project away from the valve frame subcomponent 1200 in the deployed configuration at an angle of approximately forty five (45) degrees.

In various examples, the tissue retention feature 1218 is angled between fifteen (15) and forty five (45) degrees relative to the longitudinal axis of the valve frame subcomponent 1200. For instance, in some examples, when deployed, the tissue retention feature 1218 of the valve frame subcomponent 1200 is angled at approximately thirty (30) degrees relative to a longitudinal axis of the valve frame subcomponent 1200. Generally the tissue retention feature 1218 may be angled less than fifteen (15) or alternatively more than forty five (45) degrees relative to the longitudinal axis of the valve frame subcomponent 1200, though as the angle approaches zero (0) degrees and ninety (90) degrees, the ability of the tissue retention feature 1218 to engage and capture tissue diminishes.

In various examples, the tissue retention features 1218 of the valve frame subcomponent 1200 are generally oriented such that the free ends 1220 are situated proximal to the bases 1222 of the tissue retention features 1218. As discussed in greater detail below, such a configuration provides for a tissue retention feature that is operable to engage and capture native tissue as the valve frame subcomponent 1200 and the anchor frame subcomponent 1100 are nested in-situ and cause the native tissue to be captured between the nested frames.

In various examples, while the tissue retention features 1218 are configured to project away from the valve frame subcomponent 1200 when the valve frame subcomponent 1200 is in the deployed configuration, the tissue retention features 1218 are stowed or do not otherwise project away from the valve frame subcomponent 1200 when the valve frame subcomponent 1200 is compressed or collapsed in the delivery configuration. In some examples, a constraining member disposed about the valve frame subcomponent 1200 during delivery cases stowing of the tissue retention features 1218. In some examples, the tissue retention features 1218 are stowed in associated voids or apertures or voids 1216 of the valve frame subcomponent 1200. Thus, in various examples, the tissue retention features 1218 are configured to transition between a stowed or delivery configuration and a projecting or deployed configuration.

In some examples, the tissue retention features 1218 are resilient structures. In some examples, the tissue retention features 1218 are biased to project away from the valve frame subcomponent 1200. In other words, in various examples the tissue retention features 1218 naturally project away from the valve frame subcomponent 1200 upon the valve frame subcomponent 1200 expanding to the deployed configuration (or the constraining member otherwise being removed).

In various examples, the tissue retention features 1218 are integral to the valve frame subcomponent 1200. For example, one or more of the tissue retention features 1218 are formed in conjunction with and from the same material as the frame members 1212. In other examples, one or more of the tissue retention features 1218 are additionally or alternatively coupled to the valve frame subcomponent 1200. That is, in some examples, one or more tissue retention features 1218 are additionally or alternatively attached to the valve frame subcomponent 1200.

FIGS. 4A and 4B are side views of the prosthetic valve 1000 in a predeployed and a partially deployed configuration (e.g., prior to nesting the anchor frame subcomponent 1100 and the valve frame subcomponent 1200) with the interstage 1302 therebetween. FIG. 4A illustrates the prosthetic valve 1000 loaded on a delivery device or delivery device 1500 (e.g., a catheter) in a predeployed configuration with the anchor frame subcomponent 1100 and the valve frame subcomponent 1200 being longitudinally offset from one another (also referred to as being delivered in series) and coupled together with the interstage 1302 therebetween. FIG. 4B illustrates the prosthetic valve 1000 in a partially deployed configuration prior to nesting the anchor frame subcomponent 1100 and the valve frame subcomponent 1200 with the interstage 1302 everted therebetween. As shown, in both the predeployed and partially deployed configurations, the anchor frame subcomponent 1100 and the valve frame subcomponent 1200 are longitudinally offset relative to one another. In some examples, prior to nesting the anchor frame subcomponent 1100 and the valve frame subcomponent 1200, a proximal end 1202 of the valve frame subcomponent 1200 is positioned distal to the distal end 1104 of the anchor frame subcomponent 1100 with the interstage 1302 coupled thereto and positioned therebetween coupling them together.

With continued reference to the non-limiting illustrated example of FIG. 4A, in the predeployed configuration, the prosthetic valve 1000 is loaded on a delivery device 1500 such that the anchor frame subcomponent 1100 and the valve frame subcomponent 1200 are longitudinally offset from one another. Specifically, as shown, a proximal end 1202 of the valve frame subcomponent 1200 is positioned distal to the distal end 1104 of the anchor frame subcomponent 1100. Generally, a removable constraining member (not shown), such as a constraining sheath or a constraining tube is disposed about the prosthetic valve 1000 when the prosthetic valve 1000 is in the predeployed configuration, as those of skill in the art should appreciate. The constraining member has been removed in this illustrated example such that the underlying components of the prosthetic valve 1000 that would otherwise be masked or concealed by the constraining member are viewable.

In various examples, the longitudinal separation or offset of the anchor frame subcomponent 1100 and the valve frame subcomponent 1200 provides for a low profile delivery configuration that can be easily tracked through the vasculature of the patient. For instance, by longitudinally offsetting the anchor frame subcomponent 1100 and the valve frame subcomponent 1200, a profile of the delivery system can be minimized because, unlike conventional designs, the anchor frame subcomponent 1100, the valve frame subcomponent 1200, and the interstage 1302 do not overlap one another during delivery. In some examples, a maximum profile of the delivery device 1500 including the prosthetic valve 1000 and the constraining member (no shown) can be twenty four French (24F) or less.

Additionally, a region 1502 of the delivery device 1500 positioned between the anchor frame subcomponent 1100 and the valve frame subcomponent 1200 and adjacent to the interstage 1302 is operable to bend such that the anchor frame subcomponent 1100 and the valve frame subcomponent 1200 are temporarily misaligned with one another. In some examples, such a configuration is akin a rail cars navigating a curve. Such a configuration is beneficial in procedures where the prosthetic valve 1000 is delivered to a treatment region trans-septally, which may require a delivery device to bend ninety (90) degrees or more within the left atrium of the heart.

In various examples, upon removing a constraining member (not shown) in-situ, the prosthetic valve 1000 is operable to adopt a partially deployed configuration. In some examples, when in the partially deployed configuration, despite having expanded relative to the predeployed delivery profile, the anchor frame subcomponent 1100 and the valve frame subcomponent 1200 remain longitudinally offset relative to one another. For example, as shown in FIG. 4B, the anchor frame subcomponent 1100 and the valve frame subcomponent 1200 are longitudinally offset from one another such that the proximal end 1202 of the valve frame subcomponent 1200 is positioned distal to the distal end 1104 of the anchor frame subcomponent 1100 with the interstage 1302 therebetween.

In various examples, after deploying the prosthetic valve 1000 to the predeployed configuration, the anchor frame subcomponent 1100 and the valve frame subcomponent 1200 can be nested with one another, with the interstage 1302 being everted therebetween, in-situ. That is, in various examples, the prosthetic valve 1000 can be percutaneously delivered to a treatment region of a patient's anatomy with the anchor frame subcomponent 1100 and the valve frame subcomponent 1200 longitudinally offset relative to one another (e.g., a proximal end of the valve frame subcomponent 1200 being positioned distal to a distal end of the anchor frame subcomponent 1100), and subsequently nested with one another (e.g., a proximal end of the valve frame subcomponent 1200 being repositioned to a position proximal to a distal end of the anchor frame subcomponent 1100) in-situ.

Figure 5A:
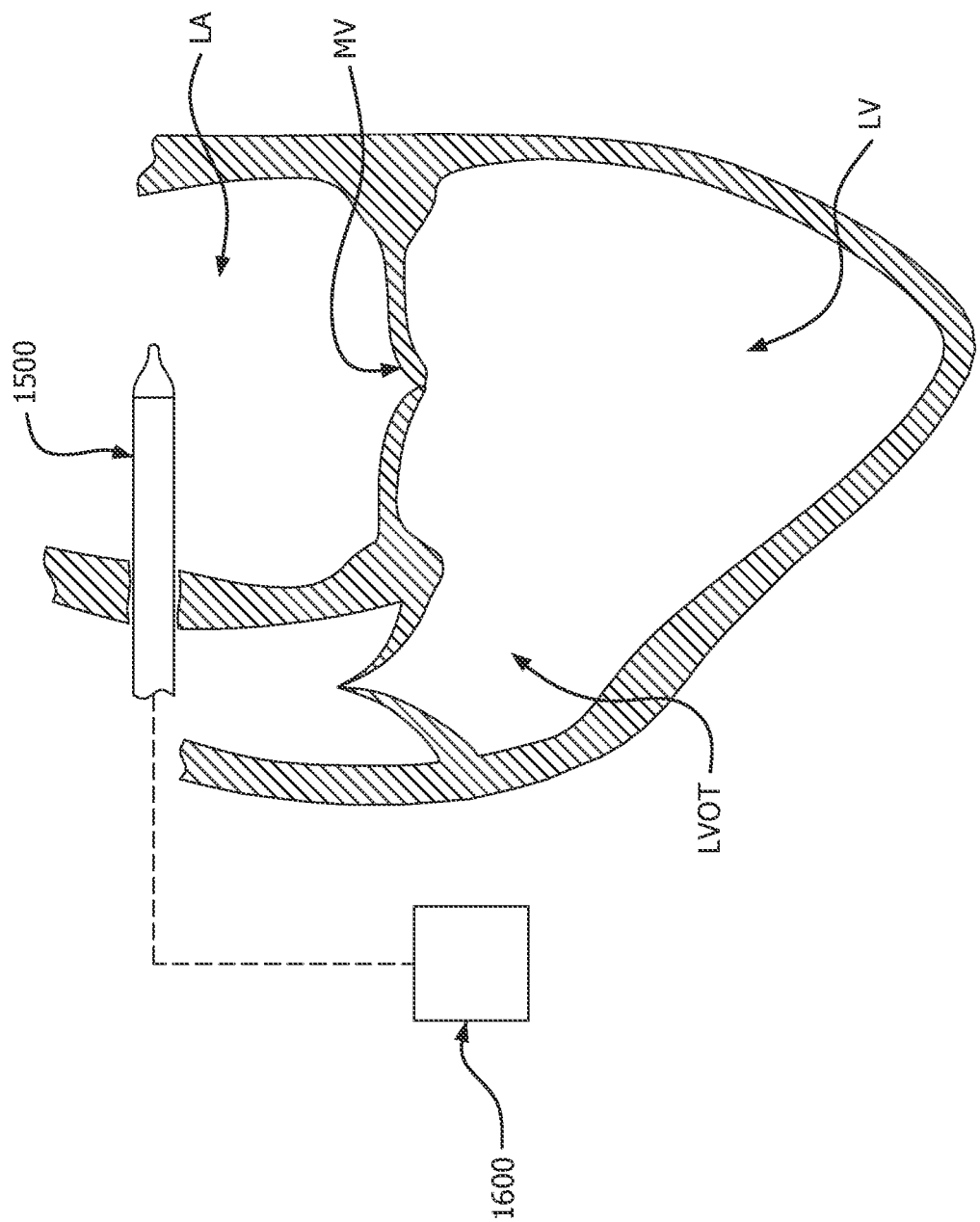
FIGS. 5A to 5E are cross-sectional views of a heart illustrating an exemplary medical device delivery procedure, according to some embodiments.
Figure 5B:
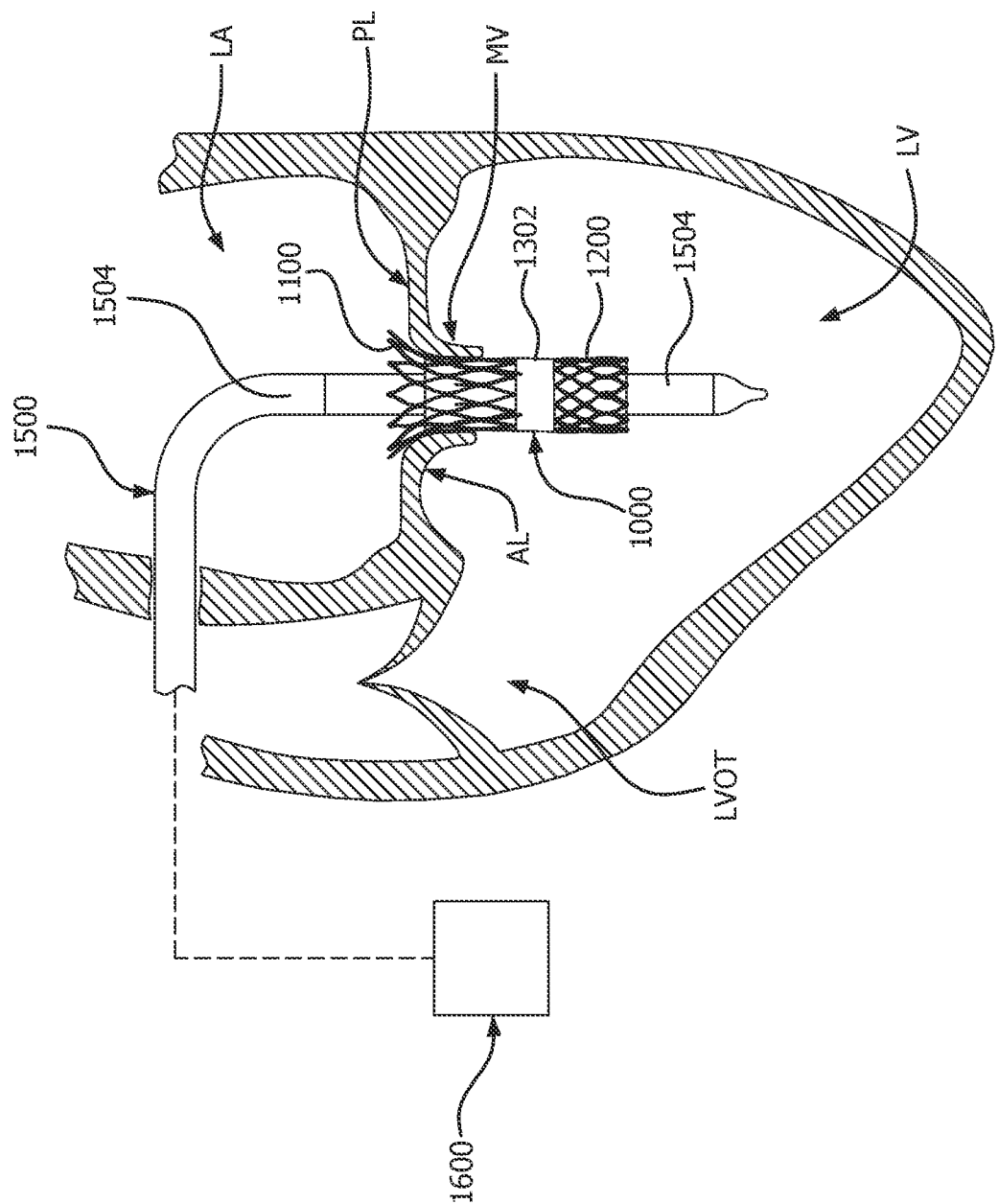

FIGS. 5A-5E illustrate a an non-limiting exemplary deployment sequence and nesting configuration of the prosthetic valve 1000 in-situ during a mitral valve ("MV") replacement procedure, with a cross-section of a portion of the heart for illustrative purposes. In FIG. 5A, the left atrium ("LA") is accessed trans-septally by a delivery device 1500. In various examples, the delivery device 1500 delivered percutaneously and is coupled to a control system 1600 outside of the body. Accessing the left atrium trans-septally can be done in accordance with techniques as known those of skill in the art. Upon gaining access to the left atrium trans-septally, the delivery device 1500 is positioned for deployment of the prosthetic valve 1000. For example, as shown in FIG. 5B, the delivery device 1500 is advanced through the mitral valve and into the left ventricle ("LV"). In some examples, advancement of the delivery device 1500 through the mitral valve causes the anterior leaflet ("AL") and the posterior leaflet ("PL") of the mitral valve to deflect into the left ventricle.

In various examples, the delivery device 1500 is positioned such that the prosthetic valve 1000 is properly oriented relative to the mitral valve. As shown in FIG. 5B, the delivery device 1500 is positioned such that the anchor frame subcomponent 1100 is adjacent a native mitral valve orifice and the native anterior and posterior leaflets. In various examples, once properly positioned, a constraining sheath 1504 of the delivery device 1500 is retracted relative to the prosthetic valve 1000, thereby exposing the prosthetic valve 1000. In various examples, the prosthetic valve is disposed about a core member 1506 of the delivery device 1500, as discussed in greater detail below.

In various examples, with the prosthetic valve 1000 exposed, the prosthetic valve 1000 expands or is otherwise expanded via the use of one or more expansion aids, including but not limited to one or more inflatable balloons. In some examples, expansion of the prosthetic valve 1000 includes the anchor frame subcomponent 1100 expanding relative to the native tissue of the mitral valve. In some examples, such expansion causes the anterior and/or posterior leaflets of the mitral valve to deflect further into the left ventricle and further obstruct the left ventricular outflow tract ("LVOT"). In various examples, as the anchor frame subcomponent 1100 expands or is expanded, the one or more tissue engagement features 1118 of the anchor frame subcomponent 1100 engage the native tissue surrounding the anchor frame subcomponent 1100 (e.g., the native mitral valve orifice) and secure the anchor frame subcomponent 1100 against dislodgement from the surrounding tissue, as those of skill in the art should appreciate.

Figure 5C:
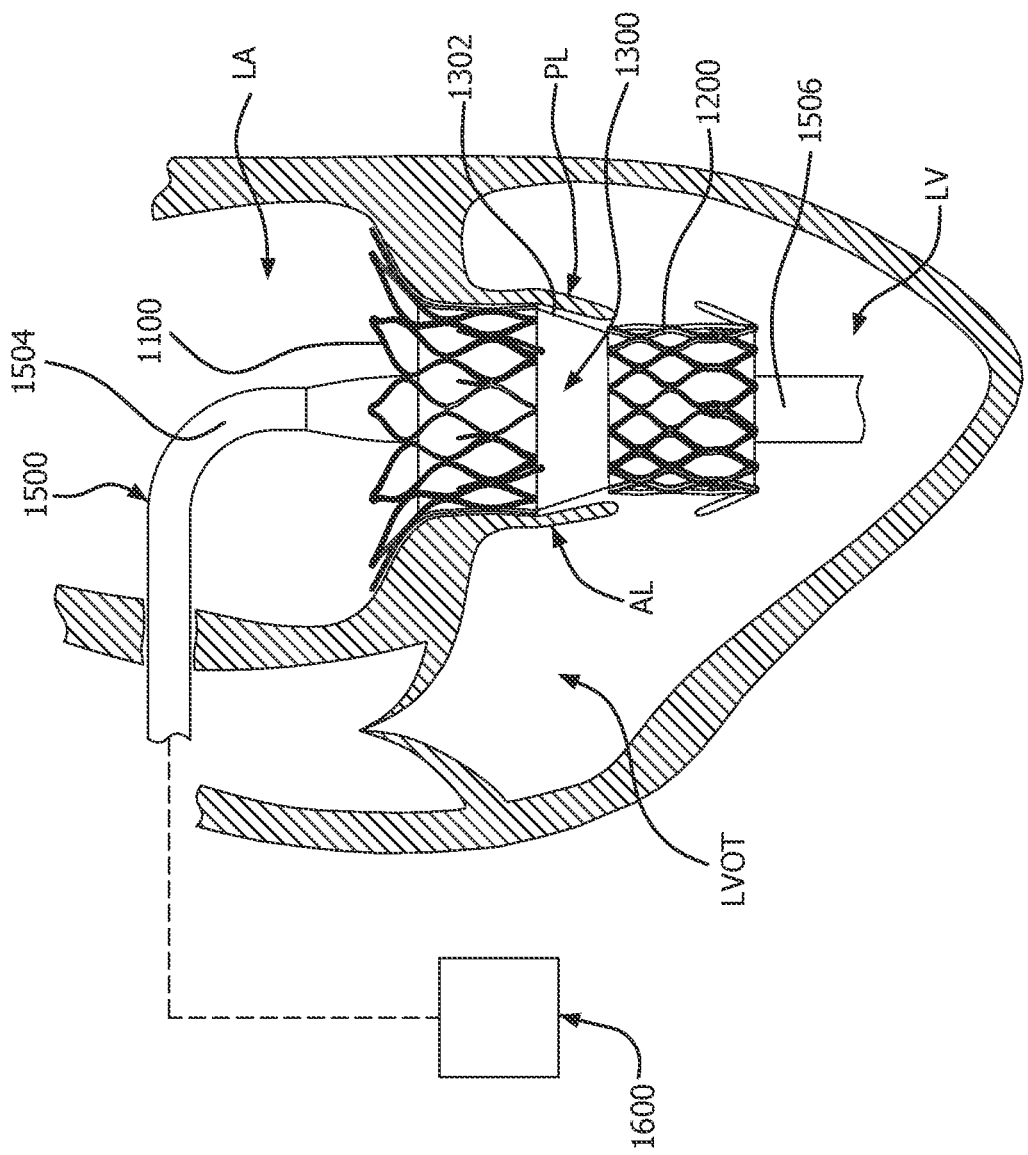
Figure 5D:
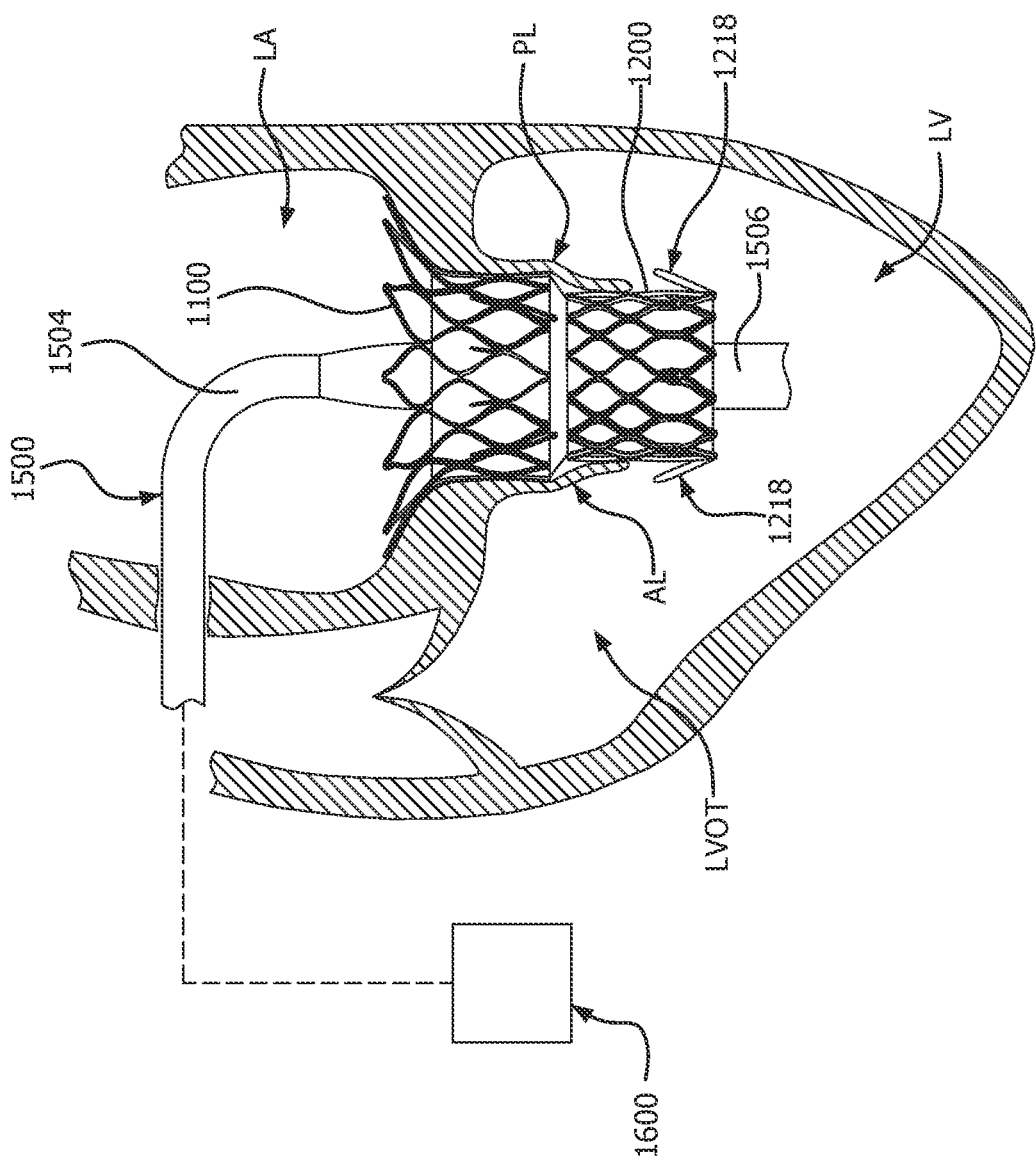

In various examples, after the anchor frame subcomponent 1100 is expanded and secured against dislodgment, the anchor frame subcomponent 1100 and the valve frame subcomponent 1200 are nested together. In various examples, nesting of the anchor frame subcomponent 1100 and the valve frame subcomponent 1200 in-situ involves proximally advancing the valve frame subcomponent 1200 relative to the anchor frame subcomponent 1100. FIG. 5D illustrates the valve frame subcomponent 1200 as it is proximally advanced relative to the anchor frame subcomponent 1100.

In various examples, the valve frame subcomponent 1200 is proximally advanced relative to the anchor frame subcomponent 1100 by way of proximally withdrawing the delivery device 1500. For instance, in some examples, the delivery device 1500 includes one or more of the constraining members referred to above. In various examples, the constraining members releasably couple the delivery device 1500 to the valve frame subcomponent 1200 such that the one or more of the constraining members are operable to transfer a proximal translation of the delivery device 1500 into a proximal translation of the valve frame subcomponent 1200. In some examples, these constraining members are configured to maintain a functional engagement between the delivery device 1500 and the valve frame subcomponent 1200 after deployment to facilitate in-situ nesting of the anchor frame subcomponent 1100 and the valve frame subcomponent 1200. In some such examples, these constraining members include one or more portions that pass between the interior surface 1206 and the exterior surface 1208 of the valve frame subcomponent 1200 by extending through the film disposed about the valve frame subcomponent 1200, as discussed above. In these examples, withdrawing the delivery device 1500 proximally causes the valve frame subcomponent 1200 to translate proximally relative to the anchor frame subcomponent 1100.

In some examples, the delivery device 1500 includes a plurality of independently movable components (e.g., a plurality of catheters) that can be longitudinally advanced and retracted relative to one another. For instance, in some examples, a first moveable component (e.g., a first catheter) can be proximally withdrawn relative to the anchor frame subcomponent 1100 while maintaining a position of a second movable component (e.g., a second catheter) relative to the anchor frame subcomponent 1100. In some such examples, the first moveable component (e.g., the first catheter) may be coupled to the valve frame subcomponent 1200 by way of one or more constraining members (as discussed herein) such that proximally withdrawing the first movable component relative to the anchor frame subcomponent 1100 and the second movable component (e.g., the second catheter) causes the valve frame subcomponent 1200 to be withdrawn into the anchor frame subcomponent 1100 such that the valve frame subcomponent 1200 can be nested with the anchor frame subcomponent 1100. In some examples, the second moveable component (e.g., the second catheter) may be coupled to the anchor frame subcomponent 1100 by way of one or more constraining members (as discussed herein) that maintaining a position of the second movable component relative to the anchor frame subcomponent 1100 as the first movable component (e.g., the first catheter) is proximally withdrawn relative to the second movable component the second movable component operates to maintain a position of anchor frame subcomponent 1100 such that the valve frame subcomponent 1200 can be nested therewith.

In some examples, one or more tethers extend between the valve frame subcomponent 1200 and the delivery device 1500. In some examples, the one or more tethers are coupled to the valve frame subcomponent 1200 such that as the delivery device 1500 is withdrawn, the valve frame subcomponent 1200 is proximally advanced relative to the anchor frame subcomponent 1100. In some examples, the one or more tethers are woven through or otherwise disposed about one or more portions of the valve frame subcomponent 1200. For instance, in some examples, a noose or similar feature is formed and disposed about a portion of the valve frame subcomponent 1200. In some examples, one or more lock wires releasably secure the one or more tethers to the valve frame subcomponent 1200.

In some examples, in addition to proximally withdrawing or advancing the valve frame subcomponent 1200, the anchor frame subcomponent 1100 is secured against longitudinal translation during the nesting procedure. In some examples, longitudinal movement of the anchor frame subcomponent 1100 is arrested by the tissue engagement features 1118 of the anchor frame subcomponent 1100 engaging the native tissue surrounding the prosthetic valve 1000. Additionally or alternatively, in some examples, the delivery device 1500 includes one or more arresting mechanisms that operate to minimize longitudinal movement of the anchor frame subcomponent 1100 during the nesting procedure. In some examples, the delivery device 1500 includes a pushing element that abuts one or more portions of the anchor frame subcomponent 1100 while the valve frame subcomponent is proximally advanced.

In various examples, as the valve frame subcomponent 1200 is proximally advanced relative to the anchor frame subcomponent 1100, the one or more tissue retention features 1218 of the valve frame subcomponent 1200 are advanced toward the native anterior and posterior leaflets of the native mitral valve and are configured to engage and capture the native anterior and/or posterior leaflets of the native mitral valve. As discussed above, the tissue retention features 1218 of the valve frame subcomponent 1200 are configured to engage and capture the native anterior and posterior leaflets of the native mitral valve between the anchor frame subcomponent 1100 and the valve frame subcomponent 1200 when the anchor frame subcomponent 1100 and the valve frame subcomponent 1200 are in a nested configuration.

Figure 5E:
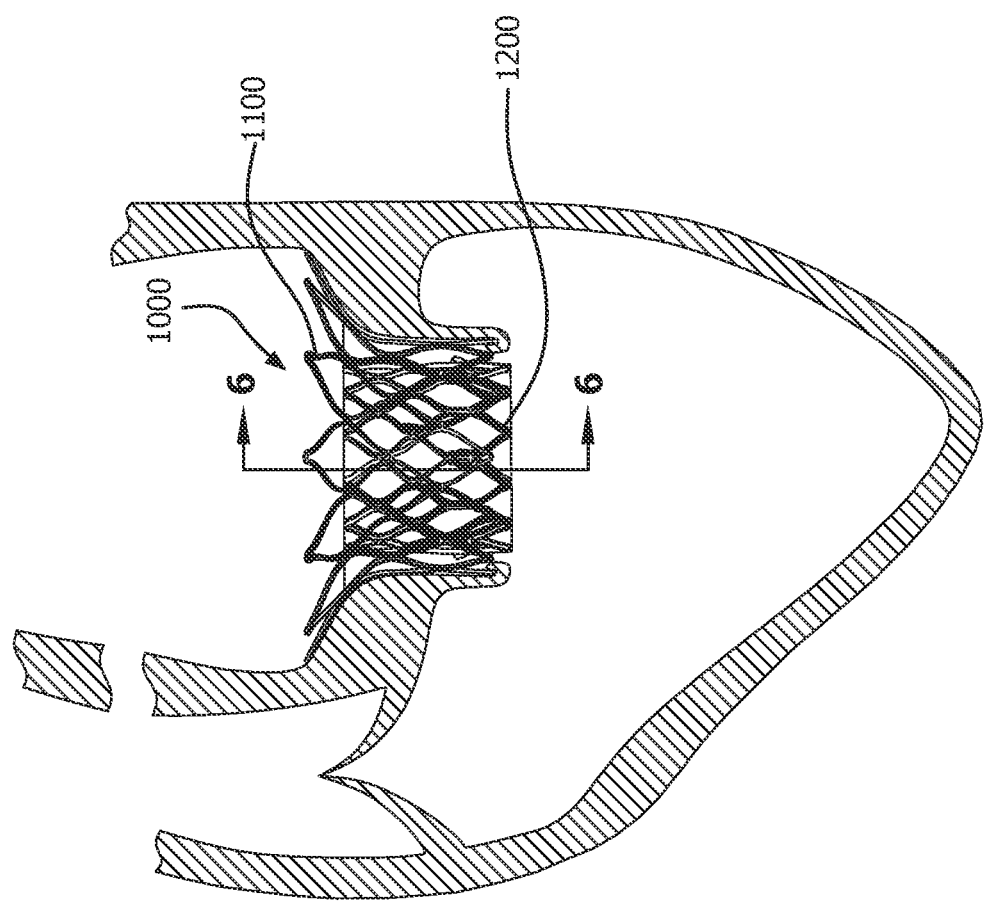

In various examples, the valve frame subcomponent 1200 is proximally advanced relative to the anchor frame subcomponent 1100 until the valve frame subcomponent 1200 becomes nested within the anchor frame subcomponent 1100. In various examples, unlike the predeployed and partially deployed configurations, in a nested configuration, the proximal end 1202 of the valve frame subcomponent 1200 is positioned proximal to the distal end 1104 of the anchor frame subcomponent 1100. FIG. 5E illustrates the valve frame subcomponent 1200 nested within the anchor frame subcomponent 1100 such the proximal end 1202 of the valve frame subcomponent 1200 is positioned proximal to the distal end 1104 of the anchor frame subcomponent 1100.

In various examples, with one or more of the native anterior and posterior leaflets of the native mitral valve engaged and/or captured by the tissue retention feature 1218 of the valve frame subcomponent 1200, the captured portions of the leaflets are proximally advanced away from the left ventricle (and the left ventricle outflow tract in particular) and toward the left atrium as the valve frame subcomponent 1200 is proximally advanced relative to the anchor frame subcomponent 1100. In various examples, this action of proximally advancing the captured portions of the native anterior and posterior leaflets of the native mitral valve operates to withdraw at least the native anterior leaflet of the mitral valve from obstructing or otherwise interfering with the left ventricular outflow tract. For example, as illustrated in FIGS. 5C and 5D, when the prosthetic valve 1000 is deployed, the native anterior leaflet of the native mitral valve is deflected toward the left ventricular outflow tract. In various examples, if not captured and retained as illustrated and described herein, the deflected native anterior leaflet of the native mitral valve extends into the left ventricle and causes a narrowing of, a restriction of, and/or an obstruction of the left ventricular outflow tract. This narrowing, restriction, and/or obstruction of the left ventricular outflow tract can lead to a number of health risks and complications as those of skill in the art will appreciate. By providing a prosthetic valve and method of implanting the same that operates to withdraw at least the native anterior leaflet of the mitral valve from obstructing or otherwise interfering with the left ventricular outflow tract, the prosthetic valve 1000 of the present application operates to minimize or eliminate the risks associated with a narrowing, restriction, and/or obstruction of the left ventricular outflow tract.

Figure 6:
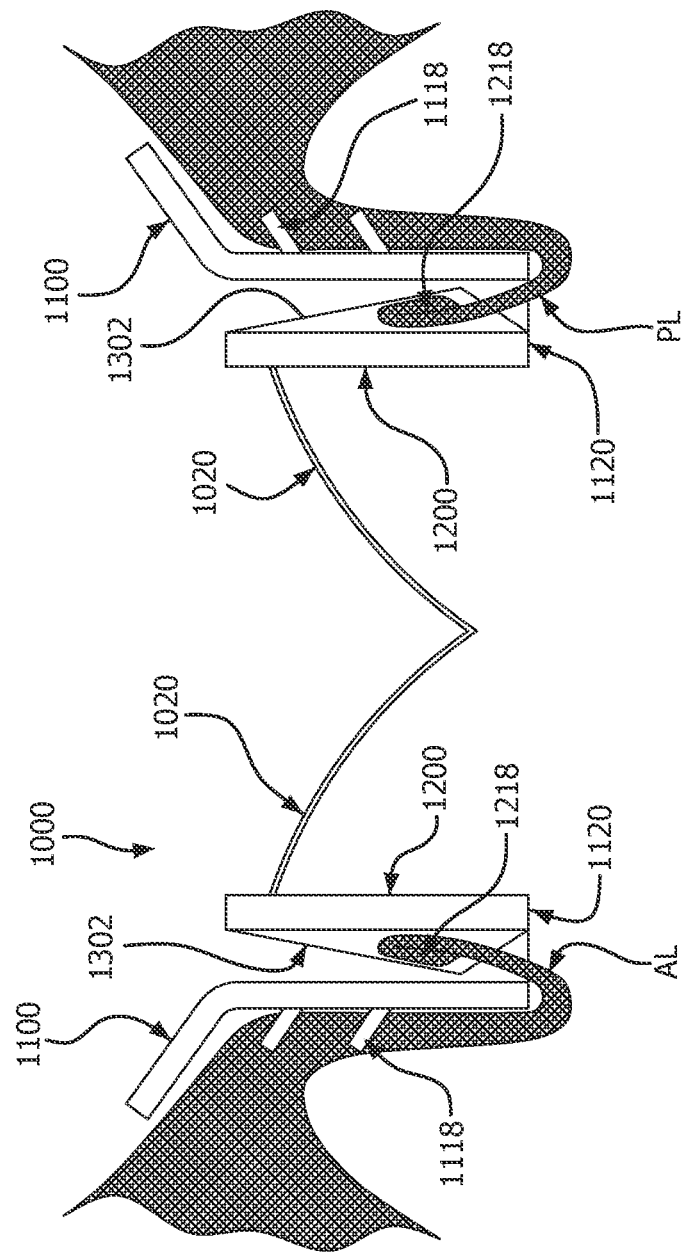
FIG. 6 is cross-sectional view of a medical device deployed in an anatomy, according to some embodiments.

FIG. 5E is an illustration of the prosthetic valve 1000 in a fully deployed configuration wherein the anchor frame subcomponent 1100 and the valve frame subcomponent 1200 are nested and at least the native anterior leaflet of the native mitral valve is captured and retained between the anchor frame subcomponent 1100 and the valve frame subcomponent 1200. In some examples, the prosthetic valve 1000 is fully deployed and operational upon the interlock features 1120 coupling together the anchor frame subcomponent 1100 and the valve frame subcomponent 1200. As discussed above, the interlock features 1120 are operable to adopt an engaged configuration wherein they engage the valve frame subcomponent 1200 and minimize relative axial translation between the anchor frame subcomponent 1100 and the valve frame subcomponent 1200 upon the valve frame subcomponent 1200 being proximally advanced a designated amount relative to the anchor frame subcomponent 1100. FIG. 6 is a cross-sectional view of FIG. 5E and illustrated the arrangement and orientation of the various components of the prosthetic valve 1000 in the fully deployed and operational configuration.

Though not illustrated, those of skill will appreciate that the native posterior and anterior leaflets of the native valve are coupled to papillary muscles within the left ventricle via the chordae tendineae. Generally, the chordae tendineae are inelastic tendons attached at one end to papillary muscles in the left ventricle, and at the other to the valve cusps of the posterior and anterior leaflets. As mentioned above, the tissue retention features 1218 generally include a free end 1220 that projects away from a base 1222 and the valve frame subcomponent 1200. This free end is configured to penetrate between the chordae tendineae to capture the anterior and posterior leaflets between the tissue retention features 1218 and the exterior surface 1208 of the valve frame subcomponent 1200.

As shown in FIG. 6, the anchor frame subcomponent 1100 and the valve frame subcomponent 1200 are nested together such that the valve frame subcomponent 1200 is coaxially received within the interior region 1110 (FIG. 2B) of the anchor frame subcomponent 1100. As shown, the native anterior and posterior leaflets of the native mitral valve are captured and secured between the valve frame subcomponent 1200 and the anchor frame subcomponent 1100. In particular, the native anterior and posterior leaflets of the native mitral valve are captured and secured in an annular space defined between the exterior surface 1208 of the valve frame subcomponent 1200 and the interior surface 1106 of the anchor frame subcomponent 1100. In some examples, the annular space is defined between overlapping portions of the exterior surface 1208 of the valve frame subcomponent 1200 and the interior surface 1106 of the anchor frame subcomponent 1100. As shown in FIG. 6, the interstage 1302 extends between and couples the anchor frame subcomponent 1100 with the valve frame subcomponent 1200 in the nested configuration. Here, the interstage 1302 is situated between the interior surface 1106 of the anchor frame subcomponent 1100 and the native anterior and posterior leaflets of the native mitral valve. In some examples, the tissue retention features 1218 of the valve frame subcomponent 1200 operate to maintain and secure the native anterior and posterior leaflets between the anchor frame subcomponent 1100 and the valve frame subcomponent 1200.

As mentioned above, in various examples, the interstage 1302 extends between the anchor frame subcomponent 1100 and the valve frame subcomponent 1200 in the nested configuration (e.g., as shown in FIG. 6). In various examples, in addition to coupling the anchor frame subcomponent 1100 with the valve frame subcomponent 1200, the interstage 1302 operates to obstruct undesirable retrograde flow through the prosthetic valve 1000. In particular, the film extending between the anchor frame subcomponent 1100 and the valve frame subcomponent 1200 in the nested configuration operates to prevent retrograde flow through the annular region defined between the anchor frame subcomponent 1100 and the valve frame subcomponent 1200. Thus, while the leaflets of the prosthetic valve 1000 are configured to close and prevent retrograde flow through the prosthetic valve 1000 (and an interior region of the valve frame subcomponent in particular), the interstage 1302 extending between the anchor frame subcomponent 1100 and the valve frame subcomponent 1200 also operates to minimize or prevent unintended retrograde flow through the prosthetic valve 1000.

Additionally, as shown in FIG. 6, the interlock features 1120 of the anchor frame subcomponent 1100 engage the valve frame subcomponent 1200 and operate to maintain a relative position of the valve frame subcomponent 1200 with the anchor frame subcomponent 1100. In various examples, the interlock features 1120 of the anchor frame subcomponent 1100 operated to minimize the potential for the valve frame subcomponent 1200 to dislodge distally from its nested position within the anchor frame subcomponent 1100. In various examples, the interlock features 1120 extend from the anchor frame subcomponent 1100 to a position distal to one or more of the distal end 1204 of the valve frame subcomponent 1200 and the proximal end 1202 of the valve frame subcomponent 1200. That is, in some examples, the interlock features 1120 extend to and engage a portion of the valve frame subcomponent 1200 between the proximal and distal ends 1202 and 1204 thereof. In other examples, in the nested configuration, the interlock features 1120 extend to a position distal to the distal end 1204 of the valve frame subcomponent 1200.

Additionally, as shown in FIG. 6, the tissue engagement features 1118 of the anchor frame subcomponent 1100 extend away from the anchor frame subcomponent 1100 and engage the tissue of the native valve orifice surrounding the prosthetic valve 1000. In some examples, the tissue engagement features 1118 are configured to penetrate the tissue or otherwise embed within the tissue. In various examples, this interaction of the tissue engagement features 1118 of the anchor frame subcomponent 1100 with the native tissue surrounding the prosthetic valve 1000 operates to secure the anchor frame subcomponent 1100 (and thus the valve frame subcomponent 1200) to the native tissue (e.g., the native valve orifice).

The proximal end 1102 of the anchor frame subcomponent 1100 illustrated in FIG. 6 is flared radially outward and is situated adjacent to and in abutment with the native valve orifice, as shown. In some examples, such a configuration provides that the proximal end 1102 of the anchor frame subcomponent 1100 obstructs or otherwise limits the extent to which the anchor frame subcomponent 1100 is operable to extend through the native valve. For instance, in the case of a mitral valve replacement, such a flared proximal end 1102 limits the extent to which the anchor frame subcomponent 1100 can be advanced through the natural mitral valve orifice and into the left ventricle. In some examples, such flared proximal end 1202 additionally operates to minimize the potential for the anchor frame subcomponent 1100 to migrate distally.

While the embodiments and examples illustrated and described above pertain to trans-septal delivery, it should be appreciated that a variety of additional well-known delivery procedures can be utilized without departing from the spirit or scope of the present application. Additional non-limiting delivery procedures include trans-apical, left atriotomy, and trans-aortic. Generally, regardless of the particular delivery procedure, those of skill should appreciate that after deploying the prosthetic valve 1000, the valve frame subcomponent 1200 and the anchor frame subcomponent 1100 are nested by proximally advancing the valve frame subcomponent 1200 relative to the anchor frame subcomponent 1100.

In various examples, a prosthetic valve and its associated delivery system is configured to enable continued valve functionality during the deployment procedure. In various examples, during a prosthetic valve deployment procedure to replace a damaged native valve, the native valve and native valve orifice are temporarily obstructed by the prosthetic valve and the delivery device. In some instances, such obstructions occur prior to the prosthetic valve being deployed and becoming operational (e.g., prior to nesting the anchor frame subcomponent and the valve frame subcomponent). Accordingly, in various examples, the prosthetic valves of the present disclosure may additionally include one or more features that are configured to permit fluid to flow through or around the prosthetic valve during the implantation procedure, prior to the prosthetic valve becoming fully operational (e.g., prior to nesting the anchor frame subcomponent and the valve frame subcomponent). For example, and with reference to FIGS. 7A and 7B, a prosthetic valve 2000 includes one or more flow enabling features 2350 formed in the interstage 1302 extending between the anchor frame subcomponent 2100 and the valve frame subcomponent 2200. FIG. 7A is a side view of the prosthetic valve 2000 with the flow enabling features 2350 in an open configuration where antegrade flow (denoted by arrow "A") is permitted. FIG. 7B is a side view of the prosthetic valve 2000 with the flow enabling features 2350 in a closed configuration where retrograde (denoted by arrow "R") flow is obstructed. In some examples, the one or more flow enabling feature 2350 include one or more perforations or apertures.

In some examples, the one or more flow enabling features 2350 additionally or alternatively include one or more mechanisms that facilitate unidirectional flow. For instance, in some examples, the flow enabling features are configured as one-way valves. In some examples, one-way valves include an aperture or perforation and a flap or element of material that overlays and is slightly larger than the aperture or perforation. In some examples, the one-way valve is oriented to permit antegrade flow through the prosthetic valve, while minimizing or preventing retrograde flow through the prosthetic valve.

Figure 5F:
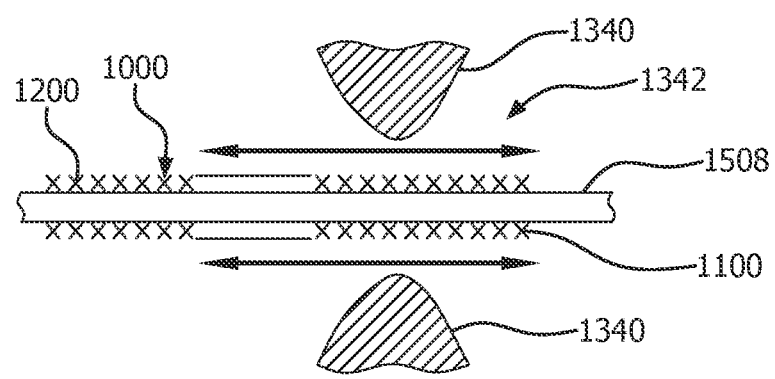
FIG. 5F is a cross-sectional view of the prosthetic valve constrained onto a delivery catheter and placed within a prosthetic valve orifice, in accordance with an embodiment.
Figure 5G:
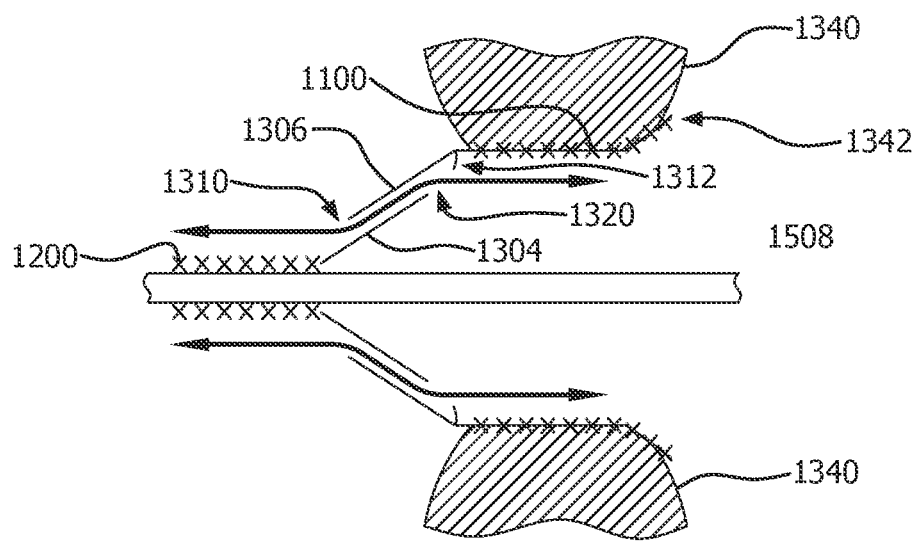
FIG. 5G is a cross-sectional view of the prosthetic valve partially deployed from the delivery catheter of FIG. 7E within the valve orifice of FIG. 5F, in accordance with an embodiment.
Figure 5H:
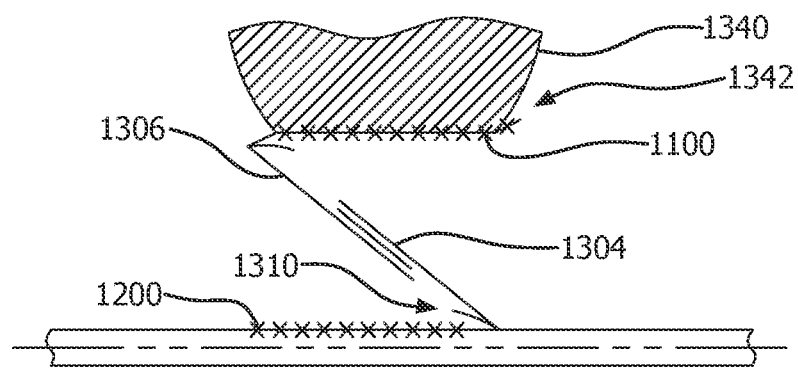
FIG. 5H is a cross-sectional view of the prosthetic valve partially deployed within the prosthetic valve orifice of FIG. 5F, in accordance with an embodiment.
Figure 5I:
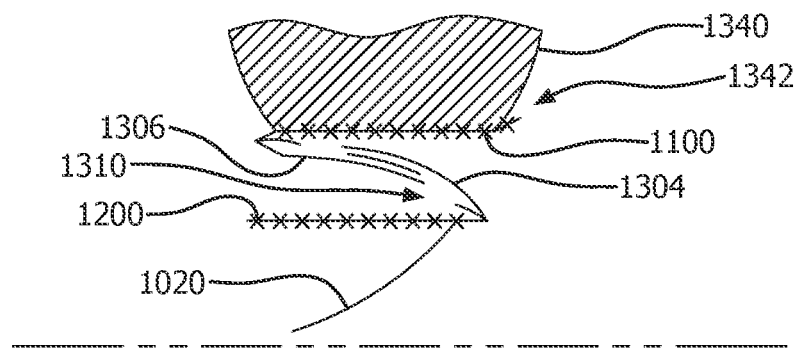
FIG. 5I is a cross-sectional view of the prosthetic valve deployed within the prosthetic valve orifice of FIG. 5F.

As shown in FIGS. 7A and 7B, the flow enabling features 2350 include an aperture 2352 and a flap 2354 that operate to enable antegrade flow through the prosthetic valve 2000 prior to the anchor frame subcomponent 2100 and the valve frame subcomponent 2200 being nested together (i.e., while the anchor frame subcomponent 2100 and the valve frame subcomponent 2200 are longitudinally offset as illustrated and described herein). The flap 1354 is oversized relative to the aperture 2352 to restrict or minimize retrograde flow through the flow enabling feature 2350 while permitting antegrade flow FIG. 7C is another embodiment of the interstage 1302 as shown coupled to the valve frame subcomponent 1200 and anchor frame subcomponent 1100. In accordance with this embodiment, the interstage 1302 is a double layer of film 1300, an inner film layer 1304 that defines an inner surface of the interstage 1302 and an outer film layer 1306 that defines an outer surface of the interstage 1300 as viewed in the partially deployed position. The inner film layer 1304 and the outer film layer 1306 are coupled together at least at the proximal end 1202 of the valve frame subcomponent 1200 and the distal end 1104 of the anchor frame subcomponent 1100. The inner film layer 1304 defines at least one inner aperture 1312 therethrough adjacent the anchor frame subcomponent 1100 and the outer film layer 1306 defines at least one outer aperture 1310 therethrough adjacent the valve frame subcomponent 1200. The inner film layer 1304 and the outer film layer 1306 are not coupled at least between one of the inner apertures 1312 and one of the outer apertures 1310 so as to define a flow space 1320 therebetween. FIG. 5F shows the prosthetic valve in a constrained state on a delivery catheter 1508, with the anchor frame subcomponent 1100 positioned within the prosthetic valve orifice 1342. As shown in FIG. 5F, when the prosthetic valve 1000 is constrained onto a delivery catheter 1508, blood flow is able to pass between the device and the tissue 1340. As shown in FIG. 5G, when the anchor frame subcomponent 1100 is deployed against the prosthetic valve orifice 1342, blood is permitted to flow through an inner aperture 1312, the flow space 1320, and an outer aperture 1310, in between the inner film layer 1304 and outer film layer 1306, in the forward flow direction but is prevented from flowing back in a retrograde direction. When the valve frame subcomponent 1200 is unconstrained and expands to the deployed diameter, the blood may continue to flow through the inner aperture 1312, the flow space 1320, and the outer aperture 1310 as before. As shown in FIG. 5H, the valve frame subcomponent 1200 is translated into the anchor frame subcomponent 1100, and as shown in FIG. 5I with the valve frame subcomponent 1200 expanded into its final deployed configuration, whereby everting or folding/rotating the interstage 1302, the inner film layer 1304 and the outer film layer 1306 are caused to come together under fluid pressure narrowing the flow space 1320 and closing the one or more inner apertures 1312 against the outer film layer 1306 and closing the one or more outer apertures 1310 against the inner film layer 1304, preventing flow therethrough. In this example, blood profusion may be maintained during substantially the entire deployment process.

Figure 8A:
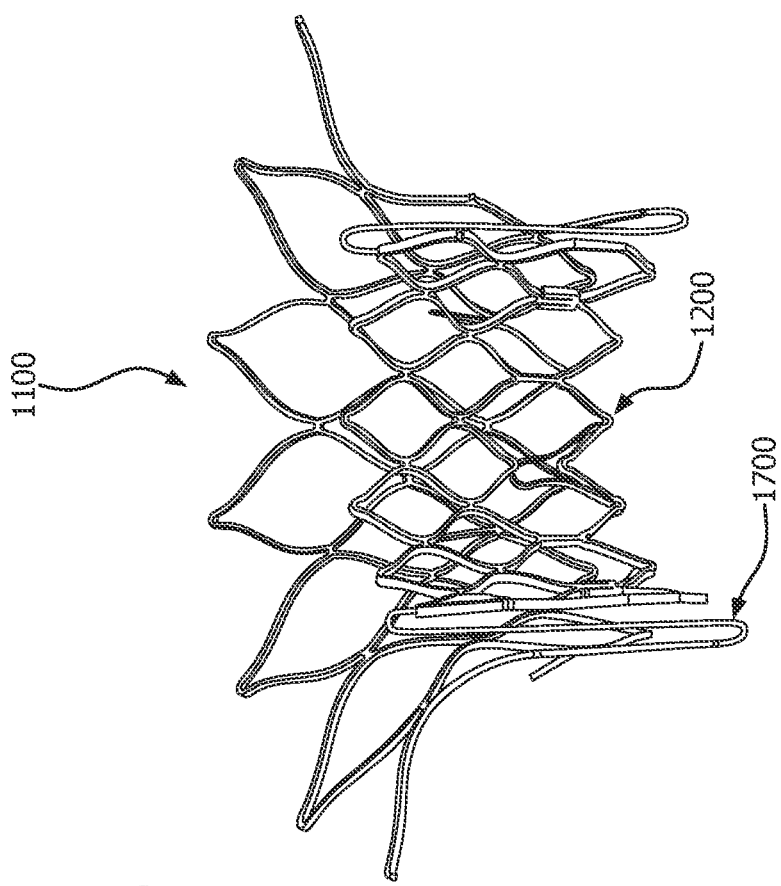
FIG. 8A is a side view of a prosthetic valve in a delivery configuration, according to some embodiments.
Figure 8B:
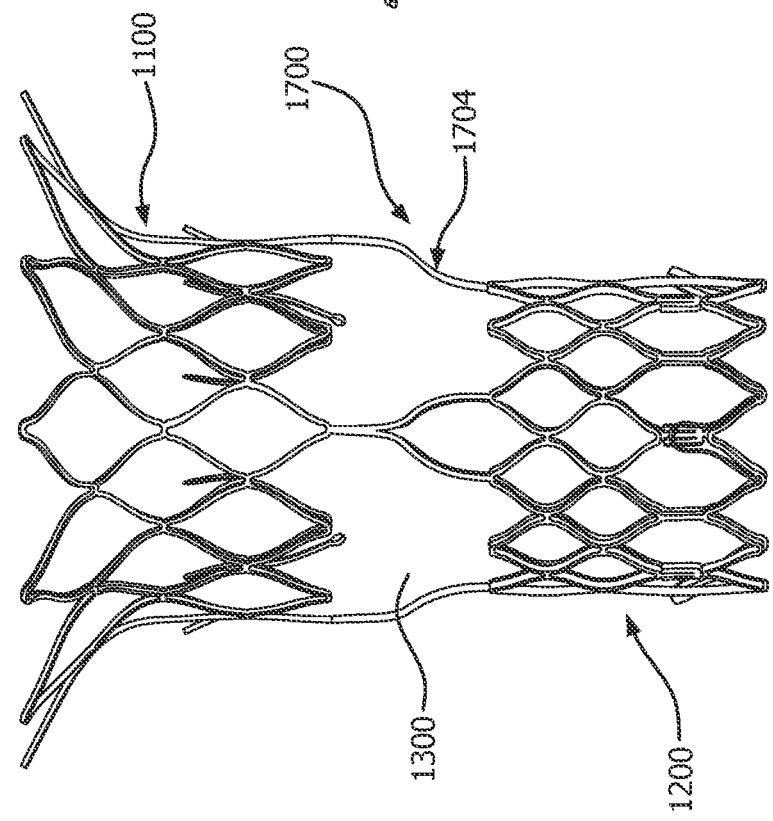
FIG. 8B is a perspective view of the prosthetic valve of FIG. 8A in a deployed configuration, according to some embodiments.

As mentioned above, in various examples, the prosthetic valve 1000 includes one or more nest interlock features 1120 that operate to maintain a coupling between the valve frame subcomponent 1200 and the anchor frame subcomponent 1100. In some examples, the prosthetic valve 1000 additionally or alternatively includes one or more features that extend between the anchor frame subcomponent 1100 and the valve frame subcomponent 1200. For example, as shown in FIGS. 8A and 8B, the prosthetic valve 1000 includes a plurality of interconnecting struts 1700 that extend between the anchor frame subcomponent 1100 and the valve frame subcomponent 1200. FIG. 8A shows the prosthetic valve 1000 prior to telescoping or nesting of the anchor frame subcomponent 1100 and the valve frame subcomponent 1200. FIG. 8B shows the prosthetic valve 1000 with the anchor frame subcomponent 1100 and the valve frame subcomponent 1200 in a nested configuration. As shown in FIGS. 8A and 8B, the interconnecting struts 1700 are configured to evert along with the interstage 1302 as the valve frame subcomponent 1200 is telescoped or nested with the anchor frame subcomponent 1100. In various examples, the interconnecting struts 1700 are elongate elements that are curved or s-shaped. It will be appreciated that such a configuration provides that the interconnecting struts 1700 can be temporarily bent or folded upon themselves as the anchor frame subcomponent 1100 an the valve frame subcomponent 1200 are nested. The interconnecting struts 1700 provides stiffening bias such that it takes a predetermined amount of force to nest the valve frame subcomponent 1200 into the anchor frame subcomponent 1100 and a corresponding predetermined amount of force to resist the movement of the valve frame subcomponent 1200 from the nested position, especially considering an interstage 1302 that does not provide sufficient resistance from movement of the valve frame subcomponent 1200 from the nested position. The interconnecting struts 1700 also provides a predetermined amount of lateral and radial stiffness to facilitate handling and deployment dynamics, especially considering an interstage 1302 that does not provide sufficient stiffness to facilitate from handling and deployment dynamics. In various examples, the interstage 1302 is very thin and thus provides little to no radial or lateral stiffness to resist the movement of the valve frame subcomponent 1200 from the nested position and/or to facilitate handling and deployment dynamics. In accordance with various examples, the interconnecting struts 1700 may be coupled to the interstage 1302, either on an inner surface, an outer surface or, in the examples having interstage 1302 that is a double layer of film 1300, contained between the inner film layer 1304 and the outer film layer 1306.

In various examples, the everted interconnecting struts 1700 operate to maintain the nested configuration of the anchor frame subcomponent 1100 and the valve frame subcomponent 1200. In some examples, with the anchor frame subcomponent 1100 and the valve frame subcomponent 1200 in the nested configuration and the interconnecting struts 1700 everted, a column strength of the interconnecting struts 1700 operates to resist compressive loads that would otherwise cause the valve frame subcomponent 1200 to de-nest or telescope out of and away from the anchor frame subcomponent 1100.

Figure 8D:
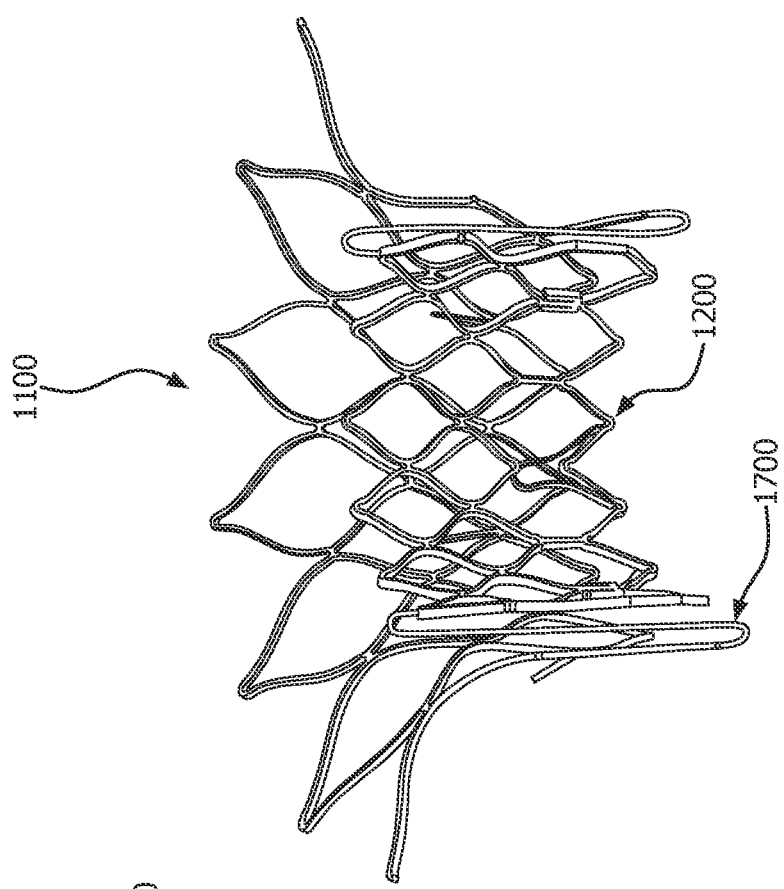
FIG. 8D is a perspective view of the prosthetic valve of FIG. 8C in a deployed configuration, according to some embodiments.
Figure 8C:
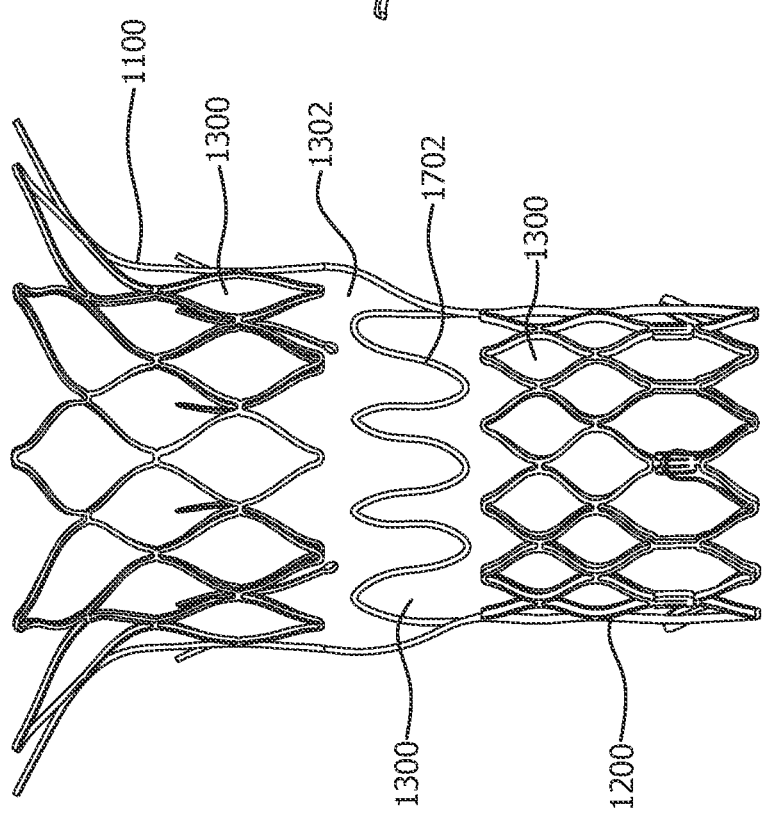
FIG. 8C is a side view of a prosthetic valve in a delivery configuration, according to some embodiments.
Figure 8E:
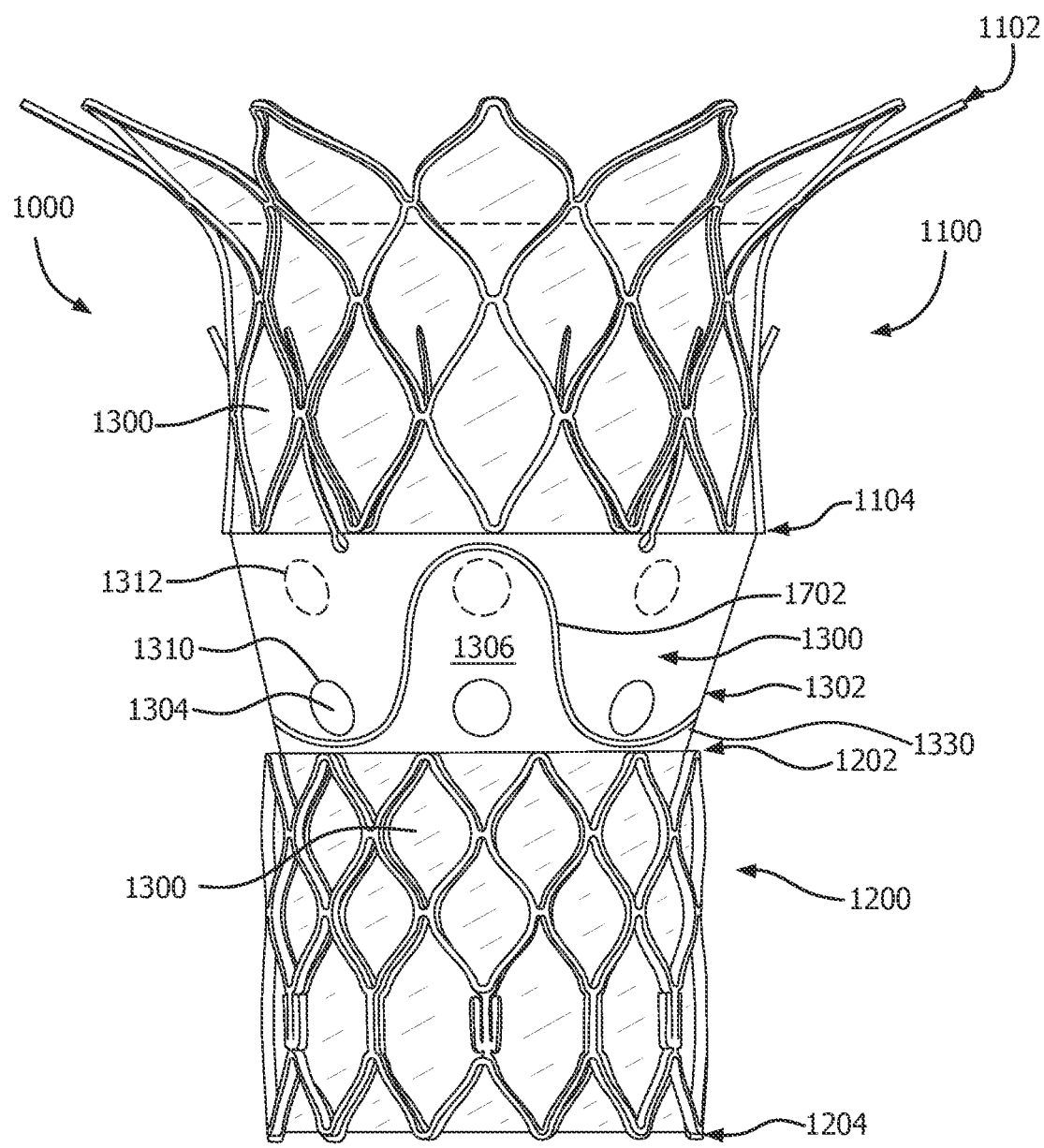
FIG. 8E is a side view of a prosthetic valve in a delivery configuration, according to some embodiments.
Figure 8F:
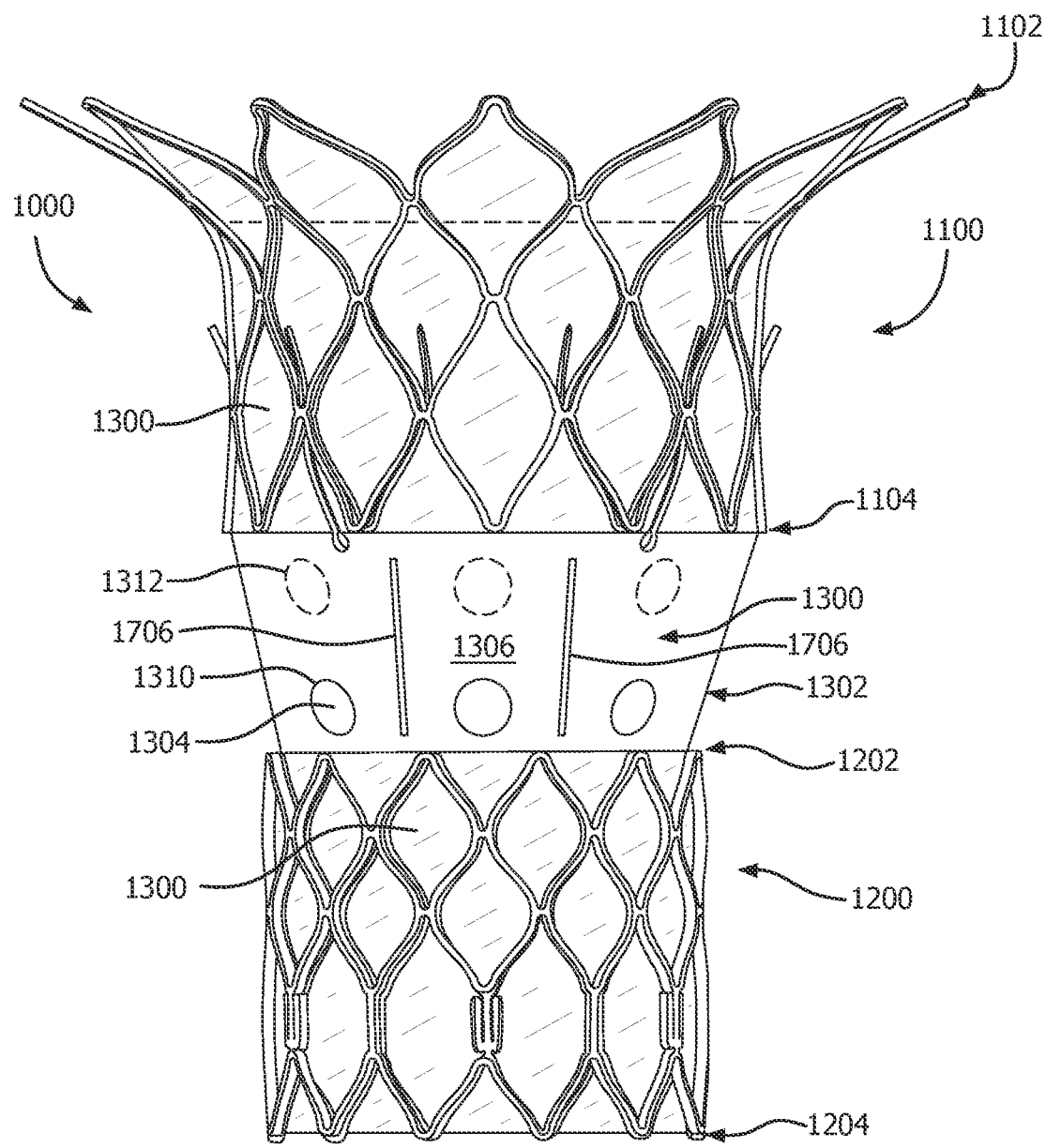
FIG. 8F is a side view of a prosthetic valve in a delivery configuration, according to some embodiments.

In accordance with other examples, as shown in FIGS. 8C and 8D, the prosthetic valve 1000 includes a nesting retention element 9999 in the form of a continuous sinuous element 1702 that extends between the anchor frame subcomponent 1100 and the valve frame subcomponent 1200 but does not couple directly therewith. The sinuous element 1702 provides stiffening bias to the interstage 1302. FIG. 8C shows the prosthetic valve 1000 prior to telescoping or nesting of the anchor frame subcomponent 1100 and the valve frame subcomponent 1200. FIG. 8D shows the prosthetic valve 1000 with the anchor frame subcomponent 1100 and the valve frame subcomponent 1200 in a nested configuration. As shown in FIGS. 8C and 8D, the sinuous element 1702 is configured to evert along with the interstage 1302 as the valve frame subcomponent 1200 is telescoped or nested with the anchor frame subcomponent 1100. In various examples, the sinuous element 1702 is an elongate element that is curved or s-shaped. It will be appreciated that such a configuration provides that the sinuous element 1702 can be temporarily elastically bent or folded upon itself as the anchor frame subcomponent 1100 an the valve frame subcomponent 1200 are nested. The sinuous element 1702 provides stiffening bias such that it takes a predetermined amount of force to nest the valve frame subcomponent 1200 into the anchor frame subcomponent 1100 and a corresponding predetermined amount of force to resist the movement of the valve frame subcomponent 1200 from the nested position, especially considering an interstage 1302 that does not provide sufficient resistance from movement of the valve frame subcomponent 1200 from the nested position. The sinuous element 1702 also provides a predetermined amount of lateral and radial stiffness to facilitate handling and deployment dynamics, especially considering an interstage 1302 that does not provide sufficient stiffness to facilitate from handling and deployment dynamics. In various examples, the interstage 1302 is very thin and thus provides little to no radial or lateral stiffness to resist the movement of the valve frame subcomponent 1200 from the nested position and/or to facilitate handling and deployment dynamics. In accordance with various examples, the sinuous element 1702 may be coupled to the interstage 1302, either on an inner surface, an outer surface or, in the examples having interstage 1302 that is a double layer of film 1300, contained between the inner film layer 1304 and the outer film layer 1306.

In various examples, the everted sinuous element 1702 operates to maintain the nested configuration of the anchor frame subcomponent 1100 and the valve frame subcomponent 1200. In some examples, with the anchor frame subcomponent 1100 and the valve frame subcomponent 1200 in the nested configuration, a column strength of the sinuous element 1702 operates to resist compressive loads that would otherwise cause the valve frame subcomponent 1200 to de-nest or telescope out of and away from the anchor frame subcomponent 1100.

the interstage 1300 further comprises a nesting retention element 1330, such as shown in FIGS. 7C-7E, to be described below, that is operable to retain the valve frame subcomponent 1200 as nested in the anchor frame subcomponent 1100. Examples of nesting retention elements 1330 are provided below. In accordance with some examples, the nesting retention elements 1330 may be elongated elements that bias the interstage 1300 in the nesting position. In accordance with an embodiment, the nesting retention elements 1330 are caused to evert during the deployment process of translating the valve frame subcomponent 1200 into the anchor frame subcomponent 1100. The nesting retention elements 1330 are provided with a predetermined stiffness or other property sufficient to permit eversion during deployment but not under normal biological forces. In accordance with another embodiment, the nesting retention elements 1330 are sized such that, when the anchor frame subcomponent 1100 is expanded and the valve frame subcomponent is compressed, the nesting retention elements 1330 are able to rotate lengthwise from a forward facing orientation to a backward facing orientation.

When the valve frame subcomponent 1200 is expanded, the nesting retention elements 1330 have a profile or length that prevents the nesting retention elements 1330 from rotating or flipping back to a forward facing orientation. In other words, the gap between the anchor frame subcomponent 1100 and the valve frame subcomponent 1200 is too narrow to allow end over end rotation of the nesting retention elements 1330. The nesting retention elements 1330 are provided with a predetermined stiffness or other property sufficient to prevent eversion of the nesting retention elements 1330 within the gap between the anchor frame subcomponent 1100 and the valve frame subcomponent 1200 under normal biological forces.

Leaflet Materials

In various examples, the leaflet 1020 is formed of a biocompatible, synthetic material (e.g., including ePTFE and ePTFE composites, or other materials as desired). In other examples, the leaflet 1020 is formed of a natural material, such as repurposed tissue, including bovine tissue, porcine tissue, or the like.

Some examples of suitable leaflet materials may be found in U.S. Pat. No. 8,961,599 to Bruchman et al. ("Durable High Strength Polymer Composite Suitable for Implant and Articles Produced Therefrom"); U.S. Pat. No. 8,945,212 to Bruchman et al. ("Durable Multi-Layer High Strength Polymer Composite Suitable for Implant and Articles Produced Therefrom"); U.S. Pat. No. 9,554,900 to Bruchman et al. ("Durable High Strength Polymer Composites Suitable for Implant and Articles Produced Therefrom"); and U.S. Pat. App. Pub. 2015/0224231 to Bruchman et al. ("Coherent Single Layer High Strength Synthetic Polymer Composites for Prosthetic Valves").

As used herein, the term "elastomer" refers to a polymer or a mixture of polymers that has the ability to be stretched to at least 1.3 times its original length and to retract rapidly to approximately its original length when released. The term "elastomeric material" refers to a polymer or a mixture of polymers that displays stretch and recovery properties similar to an elastomer, although not necessarily to the same degree of stretch and/or recovery. The term "non-elastomeric material" refers to a polymer or a mixture of polymers that displays stretch and recovery properties not similar to either an elastomer or elastomeric material, that is, considered not an elastomer or elastomeric material.

In accordance with embodiments herein, the leaflet 1020 comprises a composite material having at least one porous synthetic polymer membrane layer having a plurality of pores and/or spaces and an elastomer and/or an elastomeric material and/or a non-elastomeric material filling the pores and/or spaces of the at least one synthetic polymer membrane layer. In accordance with other examples, the leaflet 1020 further comprises a layer of an elastomer and/or an elastomeric material and/or a non-elastomeric material on the composite material. In accordance with examples, the composite material comprises porous synthetic polymer membrane by weight in a range of about 10% to 90%.

An example of a porous synthetic polymer membrane includes expanded fluoropolymer membrane having a node and fibril structure defining the pores and/or spaces. In some examples, the expanded fluoropolymer membrane is expanded polytetrafluoroethylene (ePTFE) membrane. Another example of porous synthetic polymer membrane includes microporous polyethylene membrane.

Examples of an elastomer and/or an elastomeric material and/or a non-elastomeric material include, but are not limited to, copolymers of tetrafluoroethylene and perfluoromethyl vinyl ether (TFE/PMVE copolymer), (per)fluoroalkyl-vinylethers (PAVE), urethanes, silicones (organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing. In some examples, the TFE/PMVE copolymer is an elastomer comprising between 60 and 20 weight percent tetrafluoroethylene and respectively between 40 and 80 weight percent perfluoromethyl vinyl ether. In some examples, the TFE/PMVE copolymer is an elastomeric material comprising between 67 and 61 weight percent tetrafluoroethylene and respectively between 33 and 39 weight percent perfluoromethyl vinyl ether. In some examples, the TFE/PMVE copolymer is a non-elastomeric material comprising between 73 and 68 weight percent tetrafluoroethylene and respectively between 27 and 32 weight percent perfluorom ethyl vinyl ether. The TFE and PMVE components of the TFE-PMVE copolymer are presented in wt %. For reference, the wt % of PMVE of about 40, 33-39, and 27-32 corresponds to a mol % of about 29, 23-28, and 18-22, respectively.

In some examples, the TFE-PMVE copolymer exhibits elastomer, elastomeric, and/or non-elastomeric properties.

In some examples, the composite material further comprises a layer or coating of TFE-PMVE copolymer comprising from about 73 to about 68 weight percent tetrafluoroethylene and respectively from about 27 to about 32 weight percent perfluorom ethyl vinyl ether.

In some examples, the leaflet 1020 is an expanded polytetrafluoroethylene (ePTFE) membrane having been imbibed with TFE-PMVE copolymer comprising from about 60 to about 20 weight percent tetrafluoroethylene and respectively from about 40 to about 80 weight percent perfluoromethyl vinyl ether, the leaflet 1020 further including a coating of TFE-PMVE copolymer comprising from about 73 to about 68 weight percent tetrafluoroethylene and respectively about 27 to about 32 weight percent perfluoromethyl vinyl ether on the blood-contacting surfaces.

As discussed above, the elastomer and/or an elastomeric material and/or a non-elastomeric material may be combined with the expanded fluoropolymer membrane such that the elastomer and/or the elastomeric material and/or the non-elastomeric material occupies substantially all of the void space or pores within the expanded fluoropolymer membrane.

Although some examples of suitable leaflet materials have been provided, the foregoing examples are not meant to be read in a limiting sense, and additional or alternative materials are contemplated.

In some examples, the film 1300 and/or interstage 1302 may comprise the leaflet material as described above.

Delivery Device

As discussed above, in various examples, the prosthetic valve 1000 is loaded on a delivery device 1500 in a pre-deployed configuration with the anchor frame subcomponent 1100 and the valve frame subcomponent 1200 being longitudinally offset from one another (e.g., arranged in series). In various examples, as mentioned above, one or more constraining members releasably and independently couple the valve frame subcomponent 1200 and the anchor frame subcomponent 1100 to the delivery device 1500. In various examples, as discussed in greater detail below, the one or more constraining members can be selectively released from the valve frame subcomponent 1200 and the anchor frame subcomponent 1100 to facilitate in-situ nesting of the anchor frame subcomponent 1100 and the valve frame subcomponent 1200. In some examples, one or more of the constraining members include one or more portions that may be woven through the film(s) disposed about the valve frame subcomponent 1200 and the anchor frame subcomponent 1100, such that a longitudinal actuation of the delivery device 1500 is transferrable to one or more of the valve frame subcomponent 1200 and the anchor frame subcomponent 1100 via the one or more constraining members.

Figure 9:
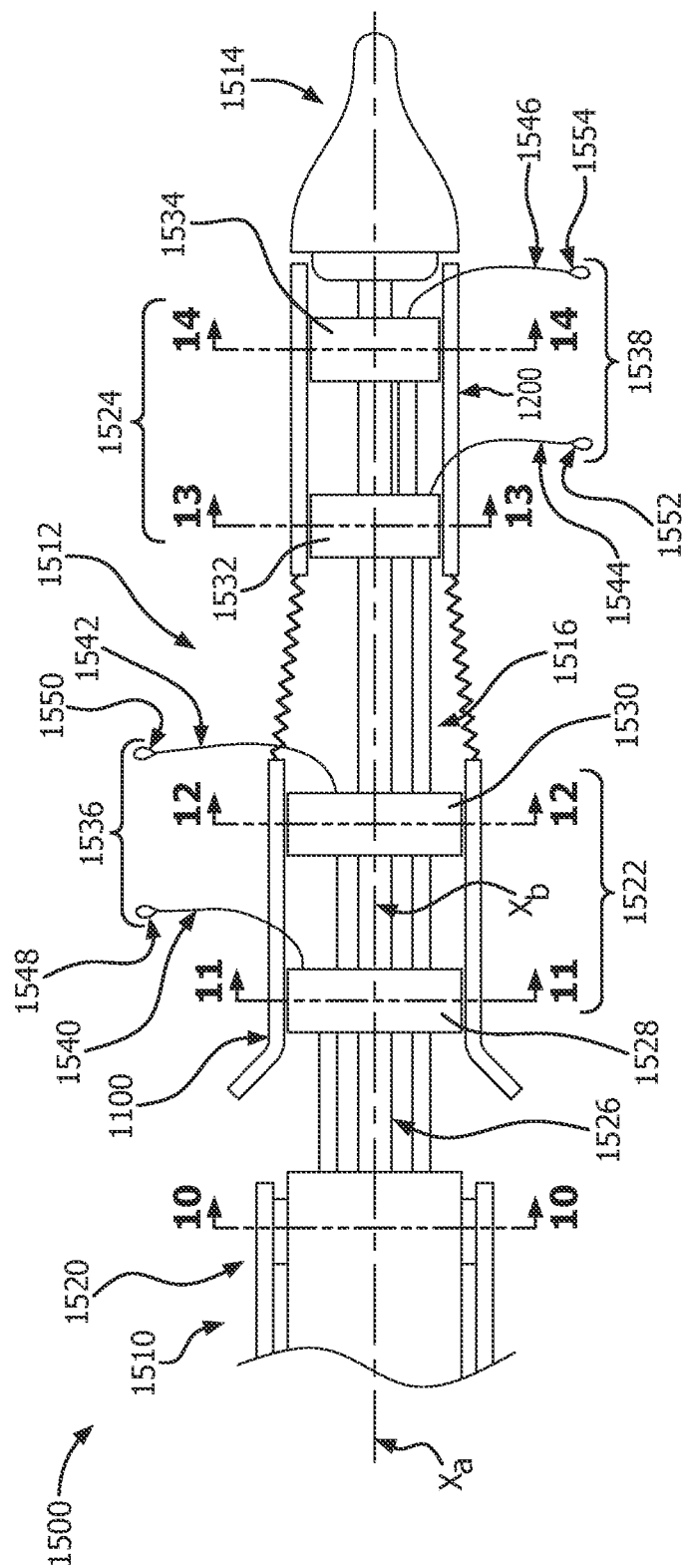
FIG. 9 is a side view of a delivery system, according to some embodiments.

FIG. 9 is a side view of a delivery device 1500, according to some embodiments. As shown, the delivery device 1500 includes a body portion 1510, a support portion 1512, a tip portion 1514, a plurality of constraints 1516. In various examples, the delivery device 1500 further includes a plurality of locking members 1518 (see, e.g., FIG. 15).

The body portion 1510 defines a central longitudinal axis Xa and has a proximal section (not shown) and a distal section 1520. The body portion 1510 is of suitable length for a user (not shown) to manipulate the delivery device 1500 from a location outside the body of a patient into which the prosthetic valve 1000 is being implanted. Generally, the body portion 1510 is of sufficient flexibility, length, and column strength such that it is suitable for traversing the vasculature or other bodily lumens and conduits within a patient (not shown).

FIG. 10 is a sectional view taken along line 10-10 in FIG. 9, according to some embodiments. As shown in FIG. 10, the body portion 1510 has a plurality of lumens 1511 extending within the body portion 1510, which can also be described as passages or channels. In various examples, the plurality of lumens 1511 extend the length of the body portion 1510 through the proximal and distal sections. In some embodiments, the plurality of lumens 1511 include a plurality of locking member lumens, such as first locking member lumen 1513 and second locking member lumen 1515. Additionally, in some embodiments the plurality of lumens 1511 include a first constraint lumen 1517, a second constraint lumen 1519, a third constraint lumen 1521, and a fourth constraint lumen 1523, although a number of additional lumens (e.g., eight, ten, twelve, etc.), are contemplated. In some embodiments, the plurality of lumens 1511 further includes a central lumen 1525. In various examples, the first and second locking member lumens 1513 and 1515, as well as the first constraint lumen 1517, the second constraint lumen 1519, the third constraint lumen 1521, and the fourth constraint lumen 1523 are each optionally located at a desired angular position about the central longitudinal axis Xa of the body portion 1510.

As shown, the first locking member lumen 1513 is at a position corresponding to 12 o'clock or 0 degrees, the second locking member lumen 1515 is at a position corresponding to 2 o'clock, or 60 degrees, the first constraint lumen 1517 is at a position corresponding to 4 o'clock or 120 degrees, the second constraint lumen 1519 is at a position corresponding to 6 o'clock or 180 degrees, the third constraint lumen 1521 is at a position corresponding to 8 o'clock or 240 degrees, and the fourth constraint lumen 1523 is at a position corresponding to 10 o'clock, or 270 degrees. Though some examples of angular positions are provided, any number of positions can be employed as desired. As shown, the central lumen 1525 may be positioned coaxially with the longitudinal axis Xa of the body portion 1510, although, again, any number of positions can be employed as desired.

The distal section 1520 of the body portion 1510 is coupled to the support portion 1512 and optionally includes one or more features for assisting with passing the distal section 1520 into, out of, and/or through a constraining sheath. For example, the distal section may include a flare, flange, or taper, to provide an increased diametric profile to the distal section 1520 adjacent the support portion 1512. This increased diametric profile, also described as an outer transverse profile, has a relatively smooth transition to reduce snagging or mechanical friction between a constraining sheath and the distal section 1520 when the distal section 1520 is slid through, extended from, and/or retracted into such a constraining sheath and through the vasculature or other conduits within a patient (not shown).

The support portion 1512 is generally configured to be received in the prosthetic valve 1000 and to support the prosthetic valve 1000 through delivery to, and deployment at a desired treatment location in a body of a patient (not shown). As shown, the support portion 1512 extends from the distal section 1520 of the body portion 1510 and has a central longitudinal axis Xb. In various examples, the central longitudinal axis Xb of the support portion 1512 is parallel with the central longitudinal axis Xa of the body portion 1510. In some examples, the central longitudinal axis Xb is coaxial with the central longitudinal axis Xa. The support portion 1512 includes a shaft 1526. In some examples, the shaft 1526 supports the one or more constraints of the plurality of constraints 1516. In various embodiments, the shaft 1526 is a flexible elongate element and may optionally include a central lumen, such as for receiving a guidewire, as those of skill will appreciate.

In various examples, the support portion 1512 further includes a first pair of guide elements 1522 and a second pair of guide elements 1524, as discussed further below.

In various embodiments, the shaft 1526 is formed as a hollow tube (e.g., hypotube), for example using nitinol, stainless steel, or other metallic or polymeric materials. In various examples, the shaft 1526 is configured to receive a guidewire (not shown) for guiding the delivery device 1500 to a desired treatment location within the patient's anatomy. If desired, however, the shaft 1526 may also be formed as a solid member without any internal lumen. The shaft 1526 is optionally coupled to the tip portion 1514 (e.g., inserted into and press-fit or bonded to the tip portion 1514), extends a length of the support portion 1512, and is coupled to the body portion 1510 (e.g., extending through the central lumen 1525 and out of the proximal end of the body portion 1510). The shaft 1526 is optionally a single, unitary member, though separate connected components are also contemplated.

In various examples, each pair of guide elements 1522 and 1524 is adapted and arranged to interface with one or more of the constraints 1516. The first pair of guide elements 1522 generally includes a proximal guide element 1528 and a distal guide element 1530. It will be appreciated that the first pair of guide elements 1522 may additionally include an intermediate guide element situated between the proximal and distal guide elements 1528 and 1530, as desired, though one is not illustrated. In some examples, the second pair of guide elements 1524 generally includes a proximal guide element 1532 and a distal guide element 1534. It will be appreciated that the second pair of guide element may likewise additionally include an intermediate guide element situated between the proximal and distal guide elements 1532 and 1534, as desired, though one is not illustrated.

As shown in FIGS. 11 and 12, the proximal and distal guide elements 1528 and 1530 of the first pair of guide elements 1522 are generally cylindrical overall, having transverse outer profiles that are cylindrical, which also corresponds to a transverse outer profile that is circular in transverse cross-section. It will be appreciated that although cylindrical profiles are contemplated, any of a variety of tapers, steps, chamfers and other features is also contemplated. In some examples the proximal and distal guide elements 1528 and 1530 are configured to support the valve frame subcomponent 1200

In various examples, each of the proximal and distal guide elements 1528 and 1530 of the first pair of guide elements 1522 defines a central longitudinal axis (not separately labeled) that is coaxial with the central longitudinal axis Xa of the support portion 1512 and by transitive theory, the central longitudinal axis of the shaft 1526, according to some examples.

As shown in FIG. 11, in some embodiments, the proximal guide element 1528 includes a central lumen 1527 through which the shaft 1526 is received, for coupling the proximal guide element 1528 to the shaft 1526. As shown, the proximal guide element 1528 also includes a plurality of passages 1529, also described as channels or lumens. In various examples, the plurality of passages 1529 include a plurality of locking member passages, such as first locking member passage 1533 and second locking member passage 1535. Additionally, in some embodiments the plurality of passages 1529 include a first constraint passage 1537, a second constraint passage 1539, a third constraint passage 1541, and a fourth constraint passage 1543, although a number of additional passages (e.g., eight, ten, twelve, etc.), are contemplated. In various examples, the first and second locking member passages 1533 and 1535, as well as the first constraint passage 1537, the second constraint passage 1539, the third constraint passage 1541, and the fourth constraint passage 1543 are each optionally located at a desired angular position about the central longitudinal axis Xb of the support portion 1512.

As shown, the locking member passages and the constraint member passages correspond in angle and in offset with the locking member lumens and the constraint member lumens of the body portion 1510, discussed above. For example, the first locking member passage 1533 corresponds with the first locking member lumen 1513 in that the first locking member passage 1533 is at an angular position corresponding to 12 o'clock or 0 degrees.

As seen with reference between FIGS. 11 and 12, the distal guide element 1530 is substantially similar to the proximal guide element 1528. In some examples, the distal guide element 1530 is also cylindrical overall, having a transverse outer profile that is cylindrical, which also corresponds to a transverse outer profile that is circular in transverse cross-section, although any of a variety of tapers, steps, chamfers and other features are also contemplated, as mentioned above.

The distal guide element 1530 also defines a central longitudinal axis (not separately labeled) that is coaxial with the central longitudinal axis Xa of the support portion 1512 and by transitive theory, the central longitudinal axis of the shaft 1526 (as well as the proximal guide element 1528), according to some examples.

As shown in FIG. 12, in some embodiments, the distal guide element 1530 includes a central lumen 1545 through which the shaft 1526 is received, for coupling the distal guide element 1530 to the shaft 1526. As shown, the distal guide element 1530 also includes a plurality of passages 1547, also described as channels or lumens. In various examples, the plurality of passages 1547 include a plurality of locking member passages, such as first locking member passage 1553 and second locking member passage 1555. Additionally, in some embodiments the plurality of passages 1547 include a first constraint passage 1557, a second constraint passage 1559, a third constraint passage 1561, and a fourth constraint passage 1563, although a number of additional passages (e.g., eight, ten, twelve, etc.), are contemplated. In various examples, the first and second locking member passages 1553 and 1555, as well as the first constraint passage 1557, the second constraint passage 1559, the third constraint passage 1561, and the fourth constraint passage 1563 are each optionally located at a desired angular position about the central longitudinal axis Xb of the support portion 1512.

As shown, the locking member passages and the constraint member passages correspond in angle and in offset with the locking member lumens and the constraint member passages of the proximal guide element 1528, discussed above. For example, the first locking member passage 1553 corresponds with the first locking member passage 1533 in that the first locking member passage 1553 is at an angular position corresponding to 12 o'clock or 0 degrees.

In various embodiments, each of the plurality of passages 1529 of the proximal guide element 1528 is aligned with a correspond passage of the plurality of passages 1547 of the distal guide element 1530. In other words, the first locking member passage 1533 is angularly aligned with the first locking member passage 1553, and the first constraint passage 1537 with the first constraint passage 1557, etc., as mentioned above. It will be appreciated, however, that one or more of the plurality of passages 1529 and the plurality of passages 1547 may be angularly misaligned, or out of alignment with one another without departing from the spirit or scope of the present disclosure. Moreover, it should be readily appreciated that the distal guide element 1530 need not have the same number of passages as the proximal guide element 1528, as discussed below.

As shown in FIGS. 13 and 14, the proximal and distal guide elements 1532 and 1534 of the second pair of guide elements 1524 are generally cylindrical overall, having transverse outer profiles that are cylindrical, which also corresponds to a transverse outer profile that is circular in transverse cross-section. It will be appreciated that although cylindrical profiles are contemplated, any of a variety of tapers, steps, chamfers and other features is also contemplated. In some examples, a diameter of the proximal and distal guide elements 1532 and 1534 of the second pair of guide elements 1524 is generally less than a diameter of the proximal and distal guide elements 1528 and 1530 of the second pair of guide elements 1524. In some examples such a configuration provides that the valve frame subcomponent 1200 can be proximally retracted (e.g., telescoped) into an interior region defined by the anchor frame subcomponent 1100. That is, by providing proximal and distal guide elements 1532 and 1534 that have a smaller diameter, the valve frame subcomponent 1200 can be reduced to a smaller cross sections suitable for being received within the anchor frame subcomponent 1100. In some examples the proximal and distal guide elements 1532 and 1534 are configured to support the valve frame subcomponent 1200.

In various examples, each of the proximal and distal guide elements 1532 and 1534 of the second pair of guide elements 1524 defines a central longitudinal axis (not separately labeled) that is coaxial with the central longitudinal axis Xa of the support portion 1512 and by transitive theory, the central longitudinal axis of the shaft 1526, according to some examples.

As shown in FIG. 13, in some embodiments, the proximal guide element 1532 includes a central lumen 1565 through which the shaft 1526 is received, for coupling the proximal guide element 1532 to the shaft 1526. As shown, the proximal guide element 1532 also includes a plurality of passages 1567, also described as channels or lumens. In various examples, the plurality of passages 1567 include second locking member passage 1575, a first constraint passage 1577, and a second constraint passage 1579, although a number of additional passages (e.g., eight, ten, twelve, etc.), are contemplated. In various examples, the second locking member passage 1575, as well as the first constraint passage 1577 and the second constraint passage 1579, are each optionally located at a desired angular position about the central longitudinal axis Xb of the support portion 1512.

As shown, the locking member passage and the constraint member passages correspond in angle and in offset with the locking member passages and the constraint member passages of the distal guide element 1530, discussed above. For example, the second locking member passage 1575 corresponds with the second locking member passage 1555 in that the second locking member passage 1575 is at an angular position corresponding to 2 o'clock or 60 degrees.

As seen with reference between FIGS. 13 and 14, the distal guide element 1534 is substantially similar to the proximal guide element 1532. In some examples, the distal guide element 1534 is also cylindrical overall, having a transverse outer profile that is cylindrical, which also corresponds to a transverse outer profile that is circular in transverse cross-section, although any of a variety of tapers, steps, chamfers and other features are also contemplated, as mentioned above.

The distal guide element 1534 also defines a central longitudinal axis (not separately labeled) that is coaxial with the central longitudinal axis Xa of the support portion 1512 and by transitive theory, the central longitudinal axis of the shaft 1526 (as well as the proximal guide element 1532), according to some examples.

As shown in FIG. 14, in some embodiments, the distal guide element 1534 includes a central lumen 1581 through which the shaft 1526 is received, for coupling the distal guide element 1534 to the shaft 1526. As shown, the distal guide element 1534 also includes a plurality of passages 1583, also described as channels or lumens. In various examples, the plurality of passages 1583 include second locking member passage 1585, a first constraint passage 1587, and a second constraint passage 1589, although a number of additional passages (e.g., eight, ten, twelve, etc.), are contemplated. In various examples, the second locking member passage 1585, as well as the first constraint passage 1587 and the second constraint passage 1589, are each optionally located at a desired angular position about the central longitudinal axis Xb of the support portion 1512.

As shown, the locking member passage and the constraint member passages correspond in angle and in offset with the locking member passages and the constraint member passages of the proximal guide element 1532, discussed above. For example, the second locking member passage 1585 corresponds with the second locking member passage 1575 in that the second locking member passage 1585 is at an angular position corresponding to 2 o'clock or 60 degrees.

As shown in FIG. 9, the plurality of constraints 1516 comprise a first pair of constraints 1536 and a second pair of constraints 1538, wherein the first pair of constraints 1536 are associated with the first pair of guide elements 1522 and wherein the second pair of constraints 1538 are associated with the second pair of guide elements 1524. In various examples, each pair of constraints is adapted and arranged to interface with a respective one of the anchor frame subcomponent 1100 and the valve frame subcomponent 1200. The first pair of constraints 1536 generally includes a proximal constraint 1540 and a distal constraint 1542. It will be appreciated that the first pair of constraints 1536 may additionally include an intermediate constraint situated between the proximal and distal constraints 1540 and 1542, as desired, though one is not illustrated. The second pair of constraints 1538 generally includes a proximal constraint 1544 and a distal constraint 1546. It will be appreciated that the second pair of constraints 1538 may likewise additionally include an intermediate constraint situated between the proximal and distal constraints 1544 and 1546, as desired, though one is not illustrated.

In some embodiments, each of the plurality of constraints 1516 is formed as a fiber, strand, wire, combinations thereof or the like, and may be braided, wound, extruded, or otherwise formed of metallic or polymeric materials. For example, each of the constraints 1516 may be formed from braided strands of material, such as UHMWPE or ePTFE. Although three are shown, any number of constraints 28 (e.g., one, two, four, nine, etc.) are contemplated. In some embodiments, the proximal constraint 1540 includes a catch 1548 in the form of a terminal, closed loop or eyelet, for example. The catch 1548 is optionally formed using braiding methods (e.g., by twisting the braid into itself or through a continuous braiding method that forks a single strand into two separates strands and then rebraids them into a single strand to form an eyelet). The distal constraint 1542 similarly includes a catch 1550, as does the proximal constraint 1544, which includes catch 1552. Distal constraint 1546 includes a catch 1554.

Figure 15:
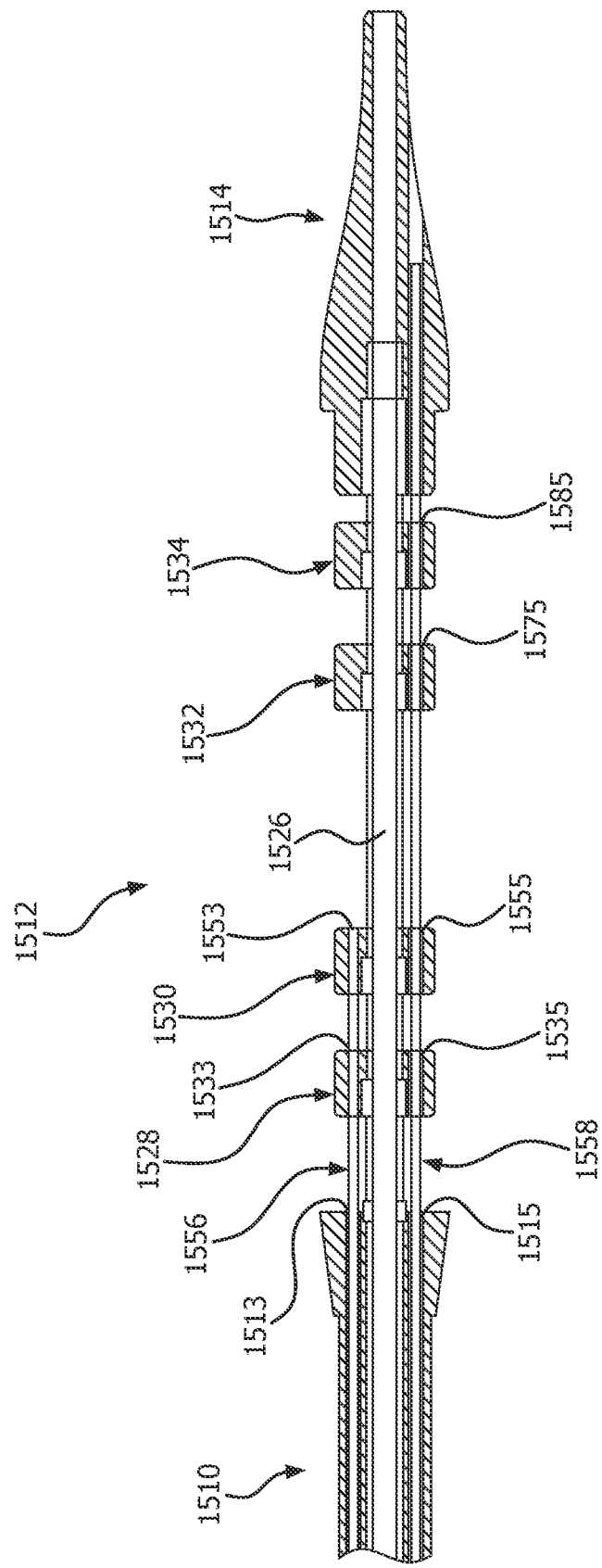
FIG. 15 is a side view of a delivery system, according to some embodiments.

In various examples, the plurality of locking members 1518 include a first locking member 1556 and a second locking member 1558. The first locking member 1556 is generally associated with securing or otherwise engaging with the first pair of constraints 1536 and the first pair of guide elements 1522, while the second locking member 1558 is generally associated with securing or otherwise engaging with the second pair of constraints 1538 and the second pair of guide elements 1524. For example, as shown in FIG. 15, the first locking member 1556 extends through first locking member lumen 1513 of the body portion 1510 and into the first locking member passages 1533 and 1553 of the proximal and distal guide elements 1528 and 1530 of the first pair of guide elements 1522. Likewise, as shown in FIG. 15, the second locking member 1558 extends through second locking member lumen 1515 of the body portion 1510, through the second locking member passages 1535 and 1555 of the proximal and distal guide elements 1528 and 1530 of the first pair of guide elements 1522, and into the second locking member passages 1575 and 1585 of the proximal and distal guide elements 1532 and 1534 of the second pair of guide elements 1524. It will be appreciated that the second locking element lumens and passages are shown in FIG. 15 as rotated approximately 120 degrees for clarity.

In various examples, the first and second locking members 1556 and 1558 are each formed as a wire, strand, fiber or the like, and may be braided, wound, extruded, or otherwise formed of metallic or polymeric materials. In some examples, the first and second locking members 1556 and 1558 are wires formed of stainless steel, nitinol, or other material. It should be appreciated that while the second locking member 1558 is illustrated as extending into the tip portion 1514, the second locking member 1558 may terminate proximal to the tip portion 1514. In some such examples, the second locking member 1558 terminates in the distal guide element 1534 of the second pair of guide elements 1524. In various examples, each of the first and second locking members 1556 and 1558 is slidably received in the respective locking member lumens and passages discussed above such that the first and second locking members 1556 and 1558 are retractable from the respective guide elements into and/or through which they extend.

In various embodiments, the first and second locking members 1556 and 1558 and the plurality of constraints 1516 extend through the body portion 1510 to the support portion 1512. In some examples, the first and second locking members 1556 and 1558 and the plurality of constraints 1516 extend from an actuation portion (not shown) coupled to the proximal end of the body portion 1510. In various examples, the actuation portion includes a handle (not shown) that is operable to manipulate the first and second locking members 1556 and 1558 and the plurality of constraints 1516. In some examples, the handle includes one or more spindles or other mechanisms that are each able to be rotated to proximally retracted or distally advance the respective constraint or locking member. In some examples, one or more of the spindles may be optionally rotationally coupled to one another and/or are independently rotatable as desired. Term "coupled" should be read in a broad sense to refer to direct or indirect attachment and to include both fixed and translatable attachment. Additionally, various forms of clutches, gears, or other means for controlling relative rotational speed, timing, or other interactions between the spindles are contemplated. The spindles may be configured to be used to wind up, or tension, and let out, or de-tension, the various constraints 1516 and locking members (e.g., 1556 and 1558).

Additionally, those of skill should appreciate that the actuation portion is operable to actuate (e.g., proximally retract and/or distally advance) the first and second locking members 1556 and 1558 independent of one another. Similarly, it should be appreciated that the actuation portion is operable to actuate one or more of the constraints of the plurality of constraints 1516 independent of each of the other constraints of the plurality of constraints. That is, in some examples each of the constraints can be independently actuated. Alternatively, in some examples, two or more constraints of the plurality of constraints 1516 may be operated in conjunction with one another, as those of skill will appreciate.

In some examples, the plurality of constraints 1516 and the first and second locking members 1556 and 1558 extend through body portion. In some examples the plurality of constraints 1516 and the first and second locking members 1556 and 1558 then extend through one or more of the guide elements of the first and/or second pairs of guide elements 1522 and 1524. For example, the plurality of constraints 1516 and the first and second locking members 1556 and 1558 extend through the respective constraint passages and locking member passages, respectively, of the proximal guide element 1528 discussed above.

Figure 16:
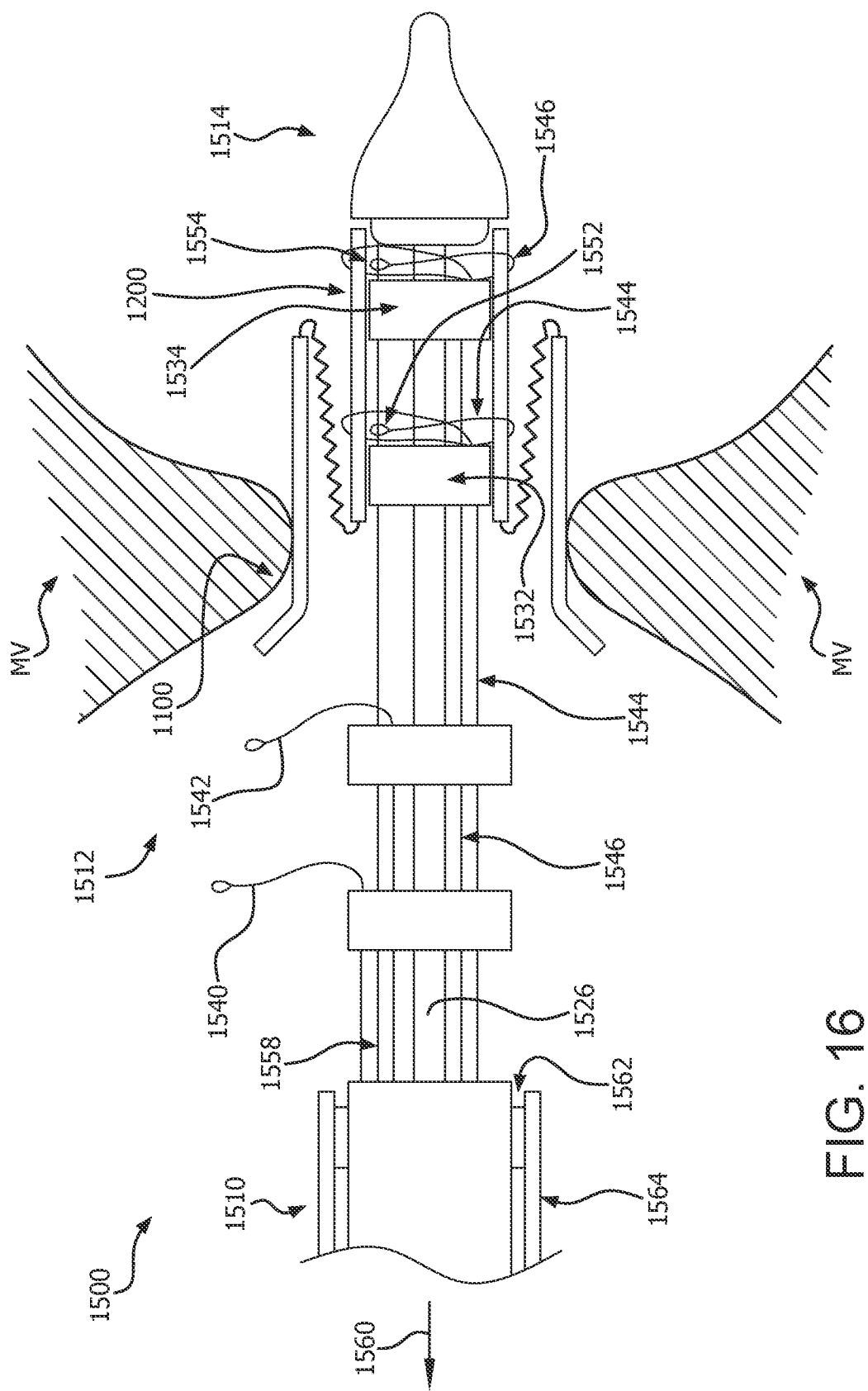
FIG. 16 is a side view of a delivery system, according to some embodiments.

In various embodiments, that the plurality of constraints 1516 are operable to extend distally out of a respective one of the plurality of passages and then radially away from the central longitudinal axis Xa of the support portion 1512. In various embodiments, each constraint (e.g., 1540, 1542, 1544, 1546) is then routed around a respective portion (e.g., valve frame subcomponent 1200 or anchor frame subcomponent 1100) of the prosthetic valve 100. In various examples, the constraint is secured to the one of the first and second locking members 1556 and 1558. In particular, the proximal and distal constraints 1540 and 1542 of the first pair of constraints 1536 are secured by the first locking member 1556, while the proximal and distal constraints 1544 and 1546 of the second pair of constraints 1538 are secured by the second locking member 1558, as discussed herein. In some examples, the constraint is routed such that the constraint forms loop and crosses back over itself (see, e.g., FIG. 16) before being secured to a respective locking member. In various examples, and as shown in FIG. 16, the constraints are secured to a respective one of the first and second locking members 1556 and 1558 by receiving the respective locking member through the catch of the constraint. As shown in FIG. 16, each of the proximal and distal constraints 1544 and 1546 are looped around the valve frame subcomponent 1200 and secured to the second locking element 1558, wherein the second locking element 1558 is received by catches 1552 and 1554 of the proximal and distal constraints 1544 and 1546, respectively.

As mentioned above, in some examples, the constraints are looped around the prosthetic valve 1000 (e.g., around a respective one of the valve frame subcomponent 1200 or the anchor frame subcomponent 1100). In various examples, one or more of the constraints 1516 is operable to be woven through one or more apertures formed in one or the other of the valve frame subcomponent 1200 and the anchor frame subcomponent 1100. For instance, it will be appreciated that the proximal and distal constraints 1544 and 1546 are operable to be woven through one or more apertures of the valve frame subcomponent 1200, while the proximal and distal constraints 1540 and 1542 are operable to be woven through one or more apertures of the anchor frame subcomponent 1100, as mentioned above. In some examples, the apertures are formed in a film, membrane, or other construct covering the valve frame subcomponent 1200 and the anchor frame subcomponent 1100. In some examples, the constraints pass exterior to the frame members 1212 of the valve frame subcomponent 1200 and exterior to the frame members 1112 of the anchor frame subcomponent 1100. It will be appreciated that with the constraints woven through the apertures of the respective frames (e.g., the valve frame subcomponent 1200 or the anchor frame subcomponent 1100), the constraints can operate to retain the valve frame subcomponent 1200 and the anchor frame subcomponent in a compacted delivery profile. Additionally, with the constraints woven through the apertures of the respective frames (e.g., the valve frame subcomponent 1200 or the anchor frame subcomponent 1100), the constraints can operate to transfer translational movement of the delivery device 1500 to the valve frame subcomponent 1200 and/or the anchor frame subcomponent 1100. Such a configuration provides that the delivery device 1500 and the valve frame subcomponent 1200 can be proximally retracted relative to the anchor frame subcomponent 1100—after the anchor frame subcomponent 1100 is deployed from the delivery system— as discussed above.

Moreover, it will be appreciated that such a configuration provides that proximally tensioning the constraints 1516 causes the constraints to constrict, thereby operating to reduce a diameter (or at least maintain a diameter) of the looped portion of the constraints, which results in looped portion of the constraint being operable to deliver a collapsing or constraining force to the prosthetic valve for example. Conversely, release of the tension permits has the opposing effect (e.g., expanding the diameter of the looped portion of the constraints 1516).

Examples of suitable attachment methods and constraining methods similar to those described above can be found in "TRANSCATHETER DEPLOYMENT SYSTEMS AND ASSOCIATED METHODS," filed by Applicant hereof on even date herewith.

Turing now to FIG. 16, a nonlimiting delivery operation in accordance with the above discussed examples and embodiments is illustrated and described. As shown, the first pair of constraints 1536 (e.g., proximal and distal constraints 1540 and 1542) has been released from the first locking member 1556 such that the anchor frame subcomponent 1100 is operable to expand and engage a valve annulus of a mitral valve, for example. However, as shown, proximal and distal constraints 1544 and 1546 remain coupled with second locking member 1558 and the valve frame subcomponent 1200.

Though not illustrated as such in FIG. 16, it will be understood that in actuality, each of the proximal and distal constraints 1544 and 1546 are woven through one or more portions of the valve frame subcomponent 1200 as discussed above. It should also be appreciated that the valve frame subcomponent 1200 is illustrated without the tissue retention features 1218 shown so that the interaction between the second pair of constraints 1538 can be visualized. Thus, though not illustrated as such, it should be appreciated that, in some examples, the distal constraint 1546 operates to maintain the tissue retention features 1218 in the stowed or delivery configuration discussed above.

Accordingly, with the anchor frame subcomponent 1100 unconstrained and the valve frame subcomponent 1200 at least partially constrained by one or more of the proximal and distal constraints 1544 and 1546, the delivery device 1500 can be proximally withdrawn in the direction of arrow 1560 (e.g., proximally translated) relative to the valve annulus and the anchor frame subcomponent 1100 such that the valve frame subcomponent 1200 is proximally withdrawn into the interior region defined by the anchor frame subcomponent 1100, as discussed herein. In various examples, the delivery device 1500 is proximally withdrawn until the valve frame subcomponent 1200 becomes nested within the anchor frame subcomponent 1100, as discussed herein.

In some examples, after releasing the first pair of constraints 1536 from the first locking member 1556 and the anchor frame subcomponent 1100, and before proximally withdrawing the delivery device 1500 and the valve frame subcomponent 1200, a tension in one or more of the proximal and distal constraints 1544 and 1546 may be reduced, thereby enabling one or more of the valve frame subcomponent 1200 and the tissue retention features 1218 to partially deploy. Thus, in such examples, the delivery device 1500 is operable to partially deploy the valve frame subcomponent 1200 prior to proximally withdrawing the delivery device 1500 and the valve frame subcomponent 1200. Such a configuration provides that the tissue retention features 1218 are allowed to expand away from the valve frame subcomponent exterior surface 1208 to a position wherein the tissue retention features 1218 are operable to engage one or more of the native leaflets of the anatomy as discussed above.

It should be appreciated that while the above discussed examples and embodiments include a delivery system including a plurality of locking members, the delivery system may be operable with a single locking member. For instance, in some examples the locking member may engage and retain each of a first constraint extending about the anchor frame subcomponent 1100 and a second constraint extending about the valve frame subcomponent 1200. In such examples the locking member is generally routed through one or more guide elements such that proximally retracting proximal end of the locking element results in a distal end of the locking element advancing at least initially distally along the support portion of the delivery system such that the constraint extending about the anchor frame subcomponent 1100 can be released prior to releasing the constraint extending about the valve frame subcomponent 1200.

The scope of the concepts addressed in this disclosure has been described above both generically and with regard to specific examples. It will be apparent to those skilled in the art that various modifications and variations can be made in the examples without departing from the scope of the disclosure. Likewise, the various components discussed in the examples discussed herein are combinable. Thus, it is intended that the examples cover the modifications and variations of the scope.

What is claimed is:

1. A prosthetic valve for replacing a native valve of a patient's anatomy, comprising:
    an anchor frame subcomponent;
    a valve frame subcomponent nestable within the anchor frame subcomponent;
    a film disposed about one or more portions of the valve frame subcomponent and the anchor frame subcomponent such that the anchor frame subcomponent is coupled to the valve frame subcomponent at least in part by a contiguous portion of the film, wherein a portion of the contiguous portion of the film is contained between the valve frame subcomponent and anchor frame subcomponent when the valve frame subcomponent is nested within the anchor frame subcomponent; and
    a tissue retention feature configured to engage tissue associated with the native valve and to secure the tissue of the native valve between the valve frame subcomponent and the anchor frame subcomponent, wherein the tissue retention feature is positioned between the valve frame subcomponent and the film when the valve frame subcomponent is nested with the anchor frame subcomponent.

2. The prosthetic valve of claim 1, wherein one or more portions of the anchor frame subcomponent and the valve frame subcomponent overlap one another such that an annular space is defined between the overlapping portions of the valve frame subcomponent and the anchor frame subcomponent when the valve frame subcomponent is nested with the anchor frame subcomponent.

3. The prosthetic valve of claim 2, wherein the tissue retention feature is configured to secure the tissue associated with the native valve within the annular space.

4. The prosthetic valve of claim 3, wherein the tissue associated with the native valve includes a leaflet of the native valve.

5. The prosthetic valve of claim 2, wherein a portion of the tissue retention feature extends radially outwardly from the valve frame subcomponent into the annular space defined between the valve frame subcomponent and the anchor frame subcomponent when the valve frame subcomponent is nested with the anchor frame subcomponent.

6. The prosthetic valve of claim 1, wherein the tissue retention feature is integral with the valve frame subcomponent.

7. The prosthetic valve of claim 1, wherein the tissue retention feature is distinct from and coupled to the valve frame subcomponent.

8. The prosthetic valve of claim 1, wherein the prosthetic valve is transitionable between a compressed configuration for transcatheter delivery and an expanded configuration wherein the prosthetic valve is operable to replace a native valve of a patient's anatomy.

\* \* \* \* \*